US012741961B2

(12) United States Patent
Tada et al.

(10) Patent No.: US 12,741,961 B2

(45) Date of Patent: Sep. 22, 2026

(54) ORGANIC ELECTROLUMINESCENT ELEMENT

(71) Applicant: NIPPON STEEL Chemical & Material Co., Ltd., Tokyo (JP)

(72) Inventors: Masashi Tada, Tokyo (JP); Munetomo Inoue, Tokyo (JP); Satoshi Ukigai, Tokyo (JP); Ayaka Terada, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 1127 days.

(21) Appl. No.: 17/775,465

(22) PCT Filed: Dec. 10, 2020

(86) PCT No.: PCT/JP2020/046173

§ 371 (c)(1),
(2) Date: May 9, 2022

(87) PCT Pub. No.: WO2021/131766

PCT Pub. Date: Jul. 1, 2021

(65) Prior Publication Data

US 2023/0023388 A1 Jan. 26, 2023

(30) Foreign Application Priority Data

Dec. 25, 2019 (JP) ................................ 2019-234729

(51) Int. Cl.
*C07D 403/14* (2006.01)
*C09K 11/06* (2006.01)
(Continued)

(52) U.S. Cl.
CPC ............ *C07D 403/14* (2013.01); *C09K 11/06* (2013.01); *H10K 85/654* (2023.02);
(Continued)

(58) Field of Classification Search
CPC .... C07D 403/14; C09K 11/06; H10K 85/658; H10K 2101/20; H10K 2101/90
See application file for complete search history.

(56) References Cited

U.S. PATENT DOCUMENTS 10,056,561 B2 8/2018 Yen
10,510,806 B2 * 12/2019 Yamaoka .............. H10K 59/32
(Continued)

FOREIGN PATENT DOCUMENTS

CN 109411634 A 3/2019
WO WO 2010/134350 A1 11/2010
(Continued)

*Primary Examiner* — Michael M Dollinger

(74) *Attorney, Agent, or Firm* — Birch, Stewart, Kolasch & Birch, LLP

(57) ABSTRACT

Provided is a blue light emitting organic EL device having high emission efficiency and a long lifetime.
An organic electroluminescent device comprising one or more light emitting layers between an anode and a cathode opposite to each other, wherein at least one of the light emitting layers contains an organic emission material having a difference between excited singlet energy (S1) and excited triplet energy (T1) (ΔEST) of 0.20 eV or less as a light emitting dopant, a first host selected from the compounds represented by the following general formula (1), and a second host selected from the compounds represented by the following general formula (2).

(Continued)

(1)

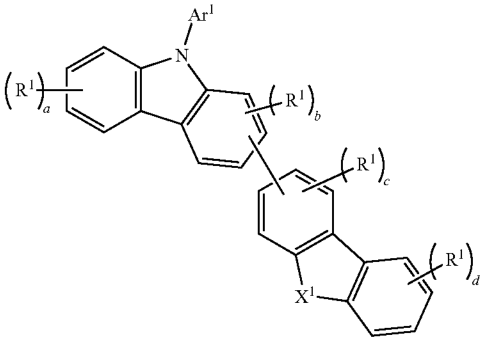

(2)

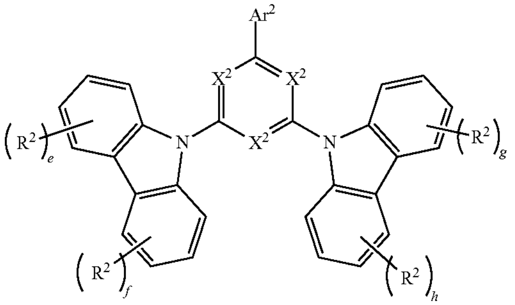

10 Claims, 1 Drawing Sheet

(51) Int. Cl.
*H10K 85/60* (2023.01)
*H10K 50/11* (2023.01)
*H10K 101/20* (2023.01)

(52) U.S. Cl.
CPC ....... *H10K 85/6572* (2023.02); *H10K 85/658* (2023.02); *C09K 2211/1007* (2013.01); *H10K 50/11* (2023.02); *H10K 2101/20* (2023.02)

(56) References Cited

U.S. PATENT DOCUMENTS

| | | | | |
|---|---|---|---|---|
| 11,539,003 | B2 * | 12/2022 | Hatakeyama | C09K 11/06 |
| 2010/0295444 | A1 | 11/2010 | Kuma et al. | |
| 2011/0260138 | A1 * | 10/2011 | Xia | H10K 85/6572 548/440 |
| 2015/0166886 | A1 | 6/2015 | Endo et al. | |
| 2015/0236274 | A1 * | 8/2015 | Hatakeyama | H10K 85/631 548/405 |
| 2016/0087227 | A1 | 3/2016 | Kim et al. | |
| 2016/0190470 | A1 * | 6/2016 | Yen | C07D 403/14 548/440 |
| 2018/0151630 | A1 * | 5/2018 | Yamaoka | H10K 59/876 |
| 2018/0337361 | A1 * | 11/2018 | Lee | H10K 85/631 |
| 2020/0144515 | A1 | 5/2020 | Hatakeyama et al. | |
| 2020/0190115 | A1 | 6/2020 | Hatakeyama et al. | |
| 2020/0203652 | A1 | 6/2020 | Duan et al. | |
| 2021/0119144 | A1 | 4/2021 | Sagara et al. | |

FOREIGN PATENT DOCUMENTS

| | | | |
|---|---|---|---|
| WO | WO 2011/070963 | A1 | 6/2011 |
| WO | WO 2015/102118 | A1 | 7/2015 |
| WO | WO 2018/212169 | A1 | 11/2018 |
| WO | WO 2019/176605 | A1 | 9/2019 |

* cited by examiner

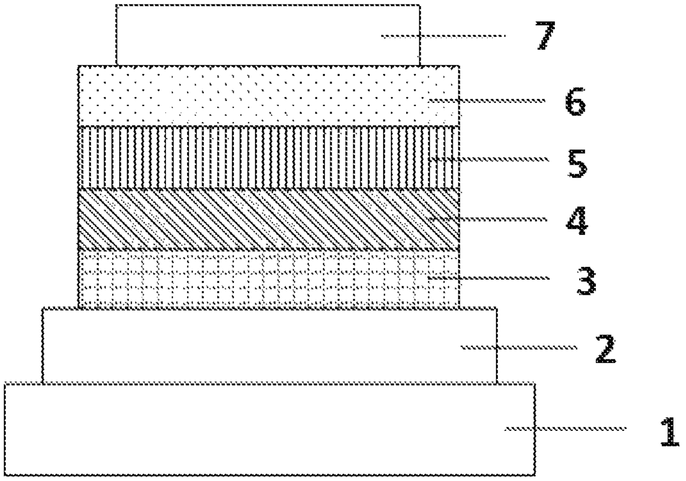
7
6
5
4
3
2
1

ORGANIC ELECTROLUMINESCENT ELEMENT

TECHNICAL FIELD

The present invention relates to an organic electroluminescent device or element (also referred to as an organic EL device or element).

BACKGROUND ART

When a voltage is applied to an organic EL device, holes and electrons are injected from the anode and the cathode, respectively, into the light emitting layer. Then, the injected holes and electrons are recombined in the light emitting layer to thereby generate excitons. At this time, according to the electron spin statistics theory, singlet excitons and triplet excitons are generated at a ratio of 1:3. In the fluorescent organic EL device that uses emission caused by singlet excitons, the limit of the internal quantum efficiency is said to be 25%. On the other hand, it has been known that, in the phosphorescent organic EL device that uses emission caused by triplet excitons, the internal quantum efficiency can be enhanced up to 100% when intersystem crossing efficiently occurs from singlet excitons.

However, the blue phosphorescent organic EL device has a technical problem of extending the lifetime.

Further, a highly efficient organic EL device utilizing delayed fluorescence has been developed, in recent years. For example, Patent Literature 1 discloses an organic EL device utilizing the Triplet-Triplet Fusion (TTF) mechanism, which is one of the mechanisms of delayed fluorescence. The TTF mechanism utilizes a phenomenon in which a singlet exciton is generated by the collision of two triplet excitons, and it is believed that the internal quantum efficiency can be enhanced up to 40%, in theory. However, its efficiency is low as compared with the efficiency of the phosphorescent organic EL device, and thus further improvement in efficiency is desired.

On the other hand, Patent Literature 2 discloses an organic EL device utilizing the Thermally Activated Delayed Fluorescence (TADF) mechanism. The TADF mechanism utilizes a phenomenon in which reverse intersystem crossing occurs from the triplet exciton to the singlet exciton in a material having a small energy difference between the singlet level and the triplet level, and it is believed that the internal quantum efficiency can be enhanced up to 100%, in theory. However, further improvement in lifetime characteristics is desired as in the phosphorescent device.

CITATION LIST

Patent Literature

Patent Literature 1: WO2010/134350
Patent Literature 2: WO2011/070963
Patent Literature 3: WO2015/102118
Patent Literature 4: WO2018/212169

Patent Literature 3 and Patent Literature 4 each discloses an organic EL device that uses a TADF material composed of a polycyclic aromatic compound typified by the following compounds as a light emitting dopant.

[Formula 1]

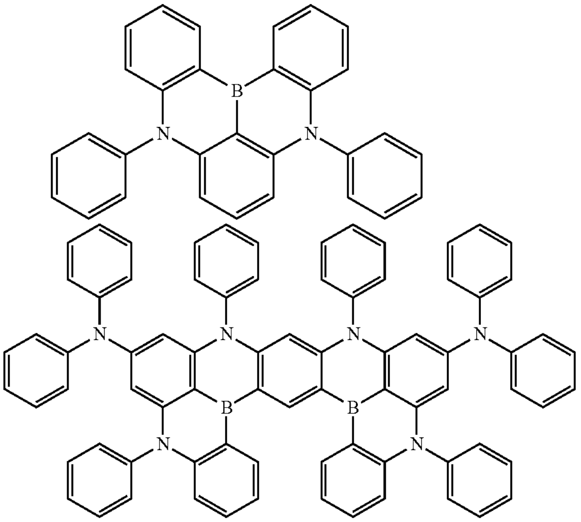

SUMMARY OF INVENTION

In order to apply an organic EL device to a display device such as a flat panel display and a light source, it is necessary to improve the emission efficiency of the device and sufficiently ensure the stability of the device at the time of driving, at the same time. An object of the present invention is to provide a practically useful organic EL device having high efficiency and high driving stability while having a low driving voltage.

The present invention relates to an organic electroluminescent device comprising one or more light emitting layers between an anode and a cathode opposite to each other, wherein at least one of the light emitting layers contains an organic emission material having a difference between excited singlet energy (S1) and excited triplet energy (T1) (REST) of 0.20 eV or less as a light emitting dopant, a first host selected from the compounds represented by the following general formula (1), and a second host selected from the compounds represented by the following general formula (2).

[Formula 2]

(1)

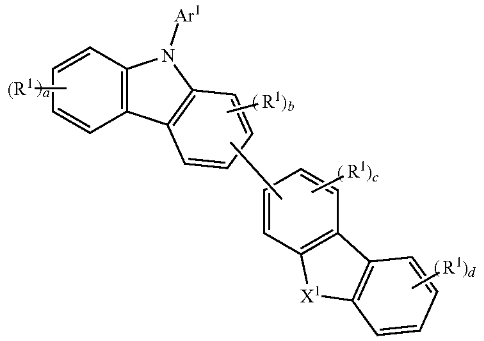

In the formula, $X^1$ represents O, S, or N-$Ar^1$. $Ar^1$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof. $R^1$ independently represents deuterium, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. a and d represent an integer of 0 to 4, and b and c represent an integer of 0 to 3.

[Formula 3]

(2)

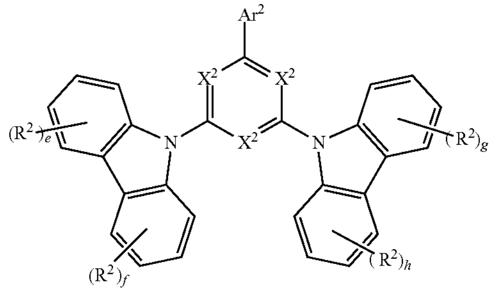

In the formula, $X^2$ independently represents N or C—H, and at least two $X^2$ represent N. Are represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof. $R^2$ independently represents deuterium, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. e, f, g, and h represent an integer of 0 to 4.

A preferred mode of the organic emission material is a boron-containing polycyclic aromatic compound represented by the following general formula (3) or (4), and a compound represented by the following general formula (4) is more preferred.

[Formula 4]

(3)

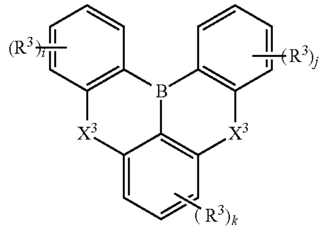

In the formula, $X^3$ represents N-$Ar^3$, O, or S, and at least one $X^3$ represents N-$Ar^3$. $Ar^3$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof. $R^3$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. i and j represent an integer of 0 to 4, and k represents an integer of 0 to 3.

[Formula 5]

(4)

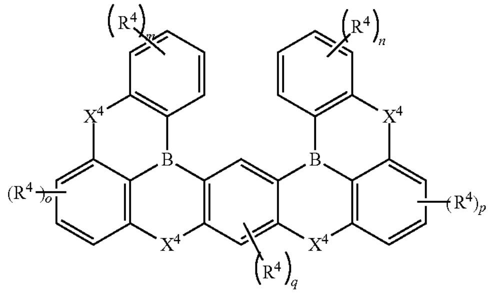

In the formula, $X^4$ represents N-$Ar^4$, O, or S, and at least one $X^4$ represents N-$Ar^4$. $Ar^4$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof. $R^4$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. m and n represent an integer of 0 to 4, o and p represent an integer of 0 to 3, and q represents an integer of 0 to 2.

$X^4$ in the general formula (4) is preferably N-$Ar^4$.

$X^1$ in the general formula (1) is preferably N-$Ar^1$.

A preferred aspect of the compound represented by the general formula (1) is a compound represented by the general formula (5).

[Formula 6]

(5)

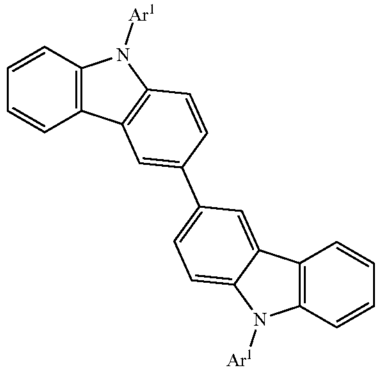

In the formula, $Ar^1$ has the same meaning as $Ar^1$ in the general formula (1).

The ΔEST of the organic emission material is preferably 0.10 eV or less.

It is preferred that 99.1 to 90 wt % of the hosts and 0.1 to 10 wt % of the light emitting dopant be contained, and that the first host and the second host be contained in an amount of 10 to 90 wt % and an amount of 90 to 10 wt %, respectively, based on the hosts.

Since the organic EL device of the present invention contains a specific light emitting dopant and a plurality of specific host materials in the light emitting layer, the organic EL device of the present invention can be an organic EL device having a low driving voltage, high emission efficiency, and a long lifetime.

BRIEF DESCRIPTION OF DRAWING

FIG. 1 shows a cross-sectional view of one example of the organic EL device.

DESCRIPTION OF EMBODIMENTS

The organic EL device of the present invention has one or more light emitting layers between an anode and a cathode opposite to each other, and at least one of the light emitting layers contains an organic emission material having a difference between excited singlet energy (S1) and excited triplet energy (T1) (ΔEST) of 0.20 eV or less as a light emitting dopant, a first host selected from the compounds represented by the following general formula (1), and a second host selected from the compounds represented by the following general formula (2).

The organic emission material used in the organic EL device of the present invention as the light emitting dopant has ΔEST of 0.20 eV or less. ΔEST is preferably 0.15 eV or less, and more preferably 0.10 eV.

ΔEST represents the difference between excited singlet energy (S1) and excited triplet energy (T1). Here, S1 and T1 are measured as follows.

A sample compound is deposited on a quartz substrate by a vacuum deposition method under conditions of a degree of vacuum of $10^{-4}$ Pa or less to form a deposition film having a thickness of 100 nm. For S1, the emission spectrum of this deposition film is measured, a tangent is drawn to the rise of the emission spectrum on the short-wavelength side, and the wavelength value λedge [nm] of the point of intersection of the tangent and the horizontal axis is substituted into the following equation (i) to calculate S1.

$$S1\ [\text{eV}]=1239.85/\lambda\text{edge} \qquad \text{(i)}$$

For T1, the phosphorescence spectrum of the above deposition film is measured, a tangent is drawn to the rise of the phosphorescence spectrum on the short-wavelength side, and the wavelength value λedge [nm] of the point of intersection of the tangent and the horizontal axis is substituted into the following equation (ii) to calculate T1.

$$T1\ [\text{eV}]=1239.85/\lambda\text{edge} \qquad \text{(ii)}$$

The above compound represented by the general formula (1) used in the present invention as the first host will be described.

$X^1$ represents O, S, or N-$Ar^1$. $X^1$ preferably represents O or N-$Ar^1$, and more preferably N-$Ar^1$.

Examples of a preferred mode of the general formula (1) include the general formula (5). In the general formulas (1) and (5), common symbols have the same meaning.

$Ar^1$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof. $Ar^1$ is preferably a substituted or unsubstituted aromatic hydrocarbon group having 6 to 12 carbon atoms, or a substituted or unsubstituted linked aromatic group formed by linking 2 to 4 of these groups. $Ar^1$ is more preferably a phenyl group, a biphenyl group, or a terphenyl group.

Specific examples of the unsubstituted $Ar^1$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 8 of these compounds. Preferred examples thereof include a group produced by removing one hydrogen atom from benzene, naphthalene, acenaphthene, acenaphthylene, azulene, and a compound formed by linking 2 to 4 of these compounds. More preferred examples thereof include a group produced by removing one hydrogen atom from benzene and a compound formed by linking 2 to 3 of these compounds.

Each of these aromatic hydrocarbon groups, aromatic heterocyclic groups, and linked aromatic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino. Preferred examples thereof include cyano, methyl, ethyl, propyl, butyl, pentyl, hexyl, heptyl, octyl, diphenylamino, naphthylphenylamino, and dinaphthylamino.

$R^1$ independently represents deuterium, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. Preferably, $R^1$ is an aliphatic hydrocarbon group having 1 to 8 carbon atoms, a substituted or unsubstituted aromatic hydrocarbon group having 6 to 12 carbon atoms, or a substituted or unsubstituted aromatic heterocyclic group having 3 to 15 carbon atoms. More preferably, $R^1$ is a substituted or unsubstituted aromatic hydrocarbon group having 6 to 10 carbon atoms, or a substituted or unsubstituted aromatic heterocyclic group having 3 to 12 carbon atoms.

a and d represent an integer of 0 to 4, and b and c represent an integer of 0 to 3.

When $R^1$ is an aliphatic hydrocarbon group having 1 to 10 carbon atoms, specific examples of $R^1$ include methyl, ethyl, propyl, butyl, pentyl, hexyl, heptyl, octyl, and nonyl. Preferred examples thereof include methyl, ethyl, propyl, butyl, pentyl, hexyl, heptyl, and octyl.

When $R^1$ is an unsubstituted aromatic hydrocarbon group having 6 to 18 carbon atoms or an unsubstituted aromatic heterocyclic group having 3 to 17 carbon atoms, specific examples of $R^1$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

Preferred examples thereof include a group produced by removing one hydrogen atom from benzene, naphthalene, acenaphthene, acenaphthylene, azulene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

More preferred examples thereof include a group produced by removing one hydrogen atom from benzene, naphthalene, azulene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

Each of these aromatic hydrocarbon groups and aromatic heterocyclic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, and diphenanthrenylamino, dipyrenylamino.

Preferred examples thereof include cyano, methyl, ethyl, propyl, butyl, pentyl, hexyl, heptyl, octyl, diphenylamino, naphthylphenylamino, and dinaphthylamino.

Specific examples of the compounds represented by the general formula (1) are shown below, but the compounds are not limited to these exemplified compounds.

[Formula 7]

1-1

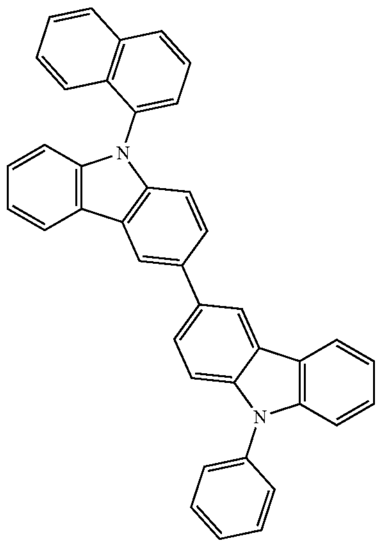

1-2

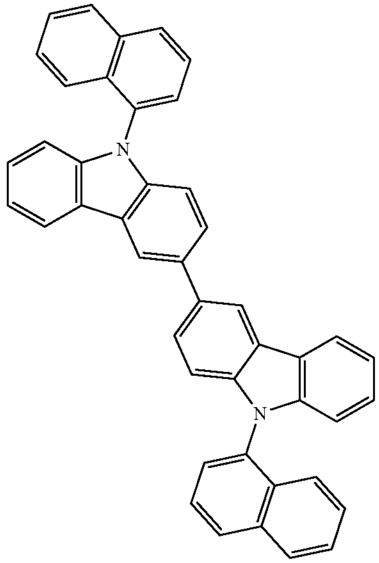

-continued
1-3
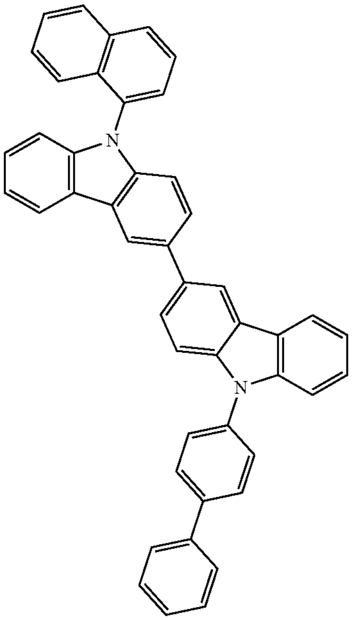
1-4
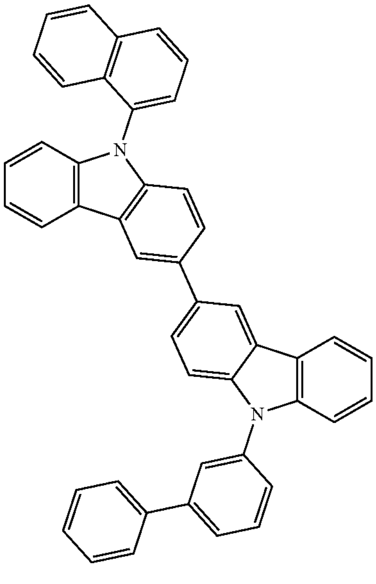
-continued
1-5
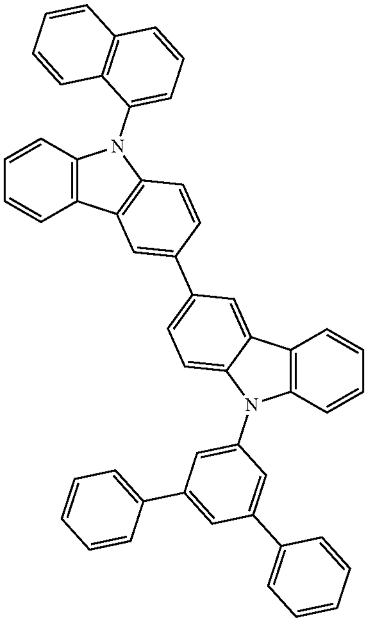
1-6
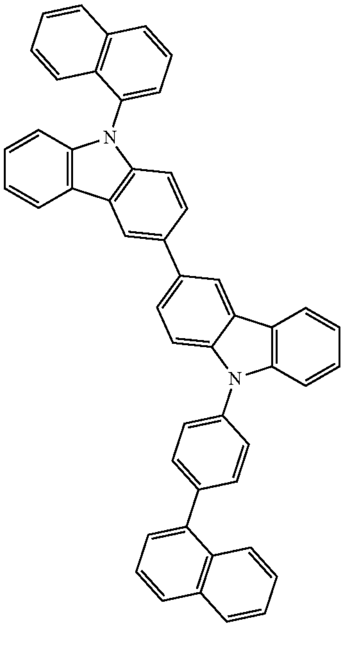

-continued
1-7
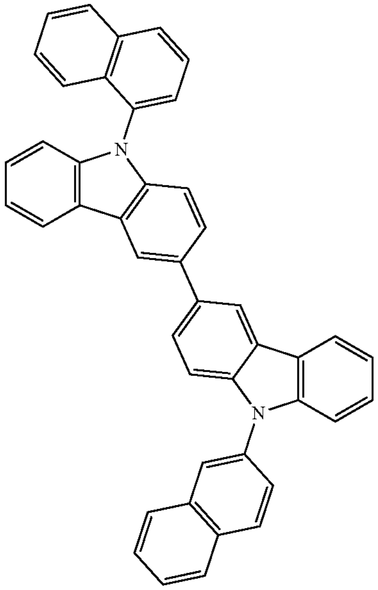
1-8
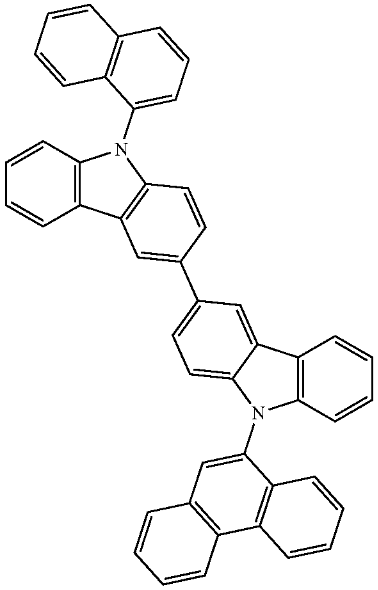
-continued
1-9
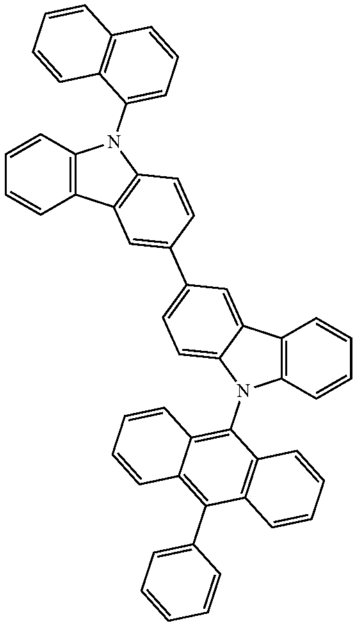
[Formula 8]
1-10
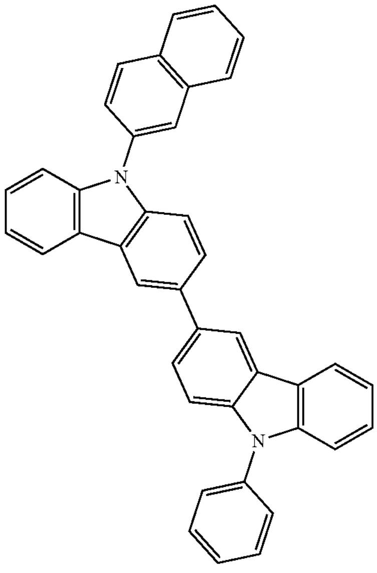

-continued
1-11
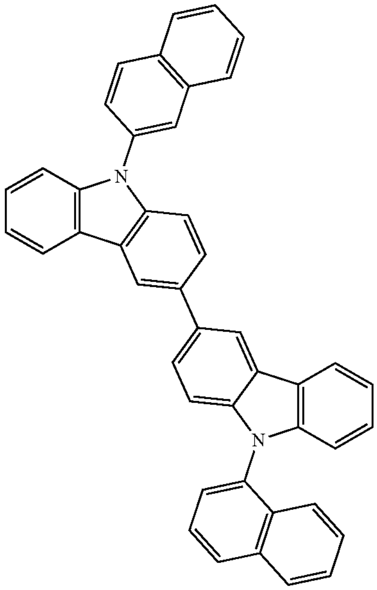
1-12
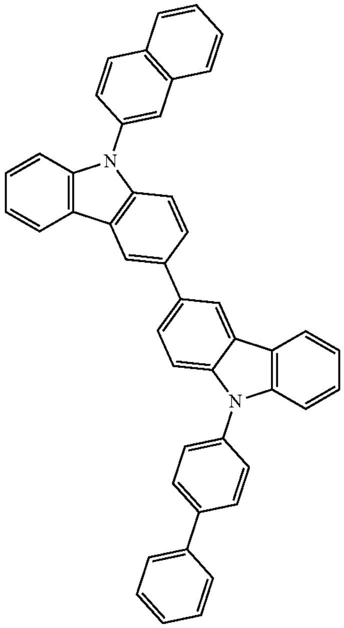
-continued
1-13
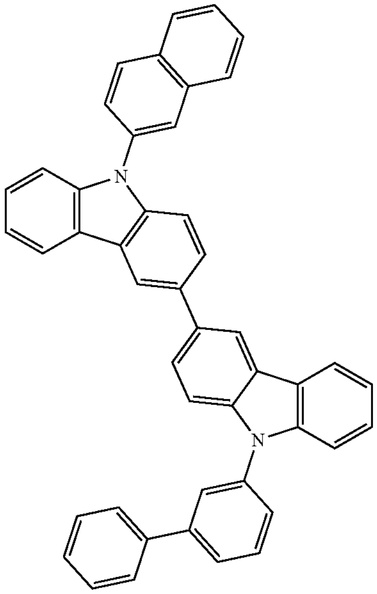
1-14
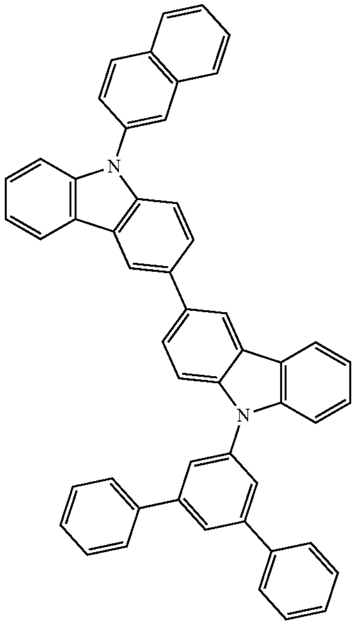

-continued
1-15
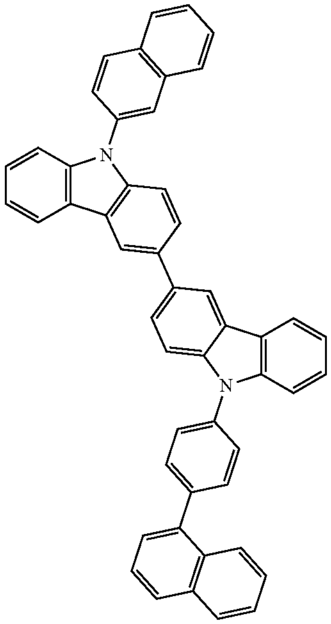
1-16
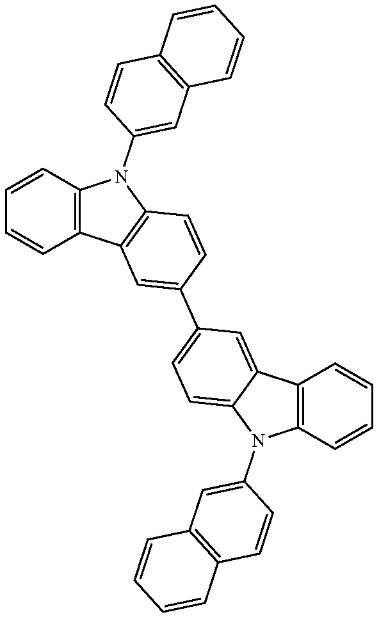
-continued
1-17
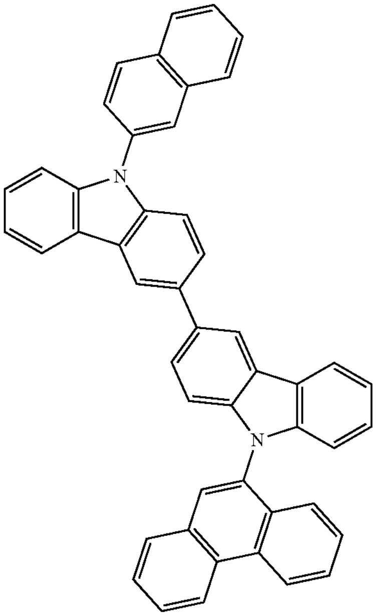
1-18
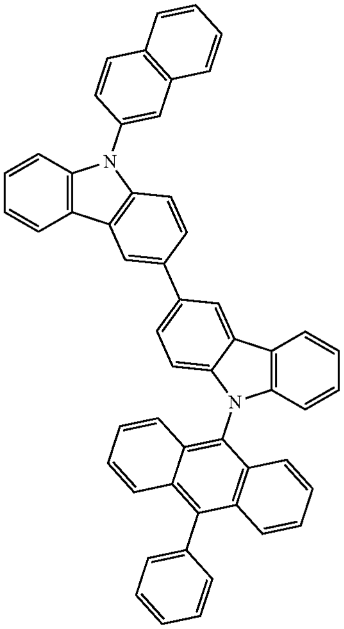

-continued
[Formula 9]
1-19
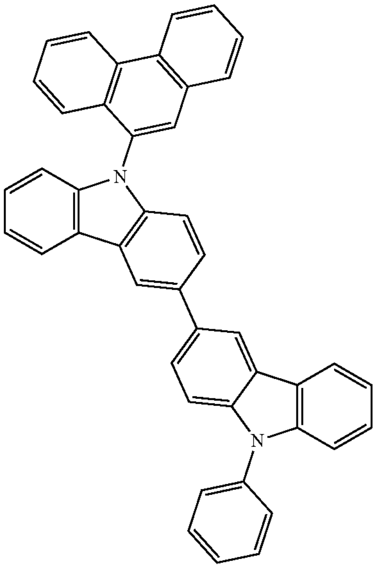
1-20
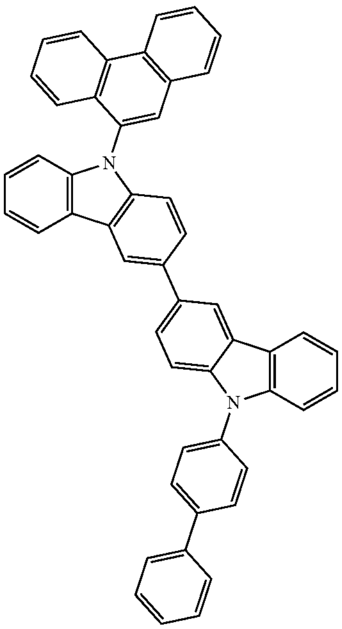
-continued
1-21
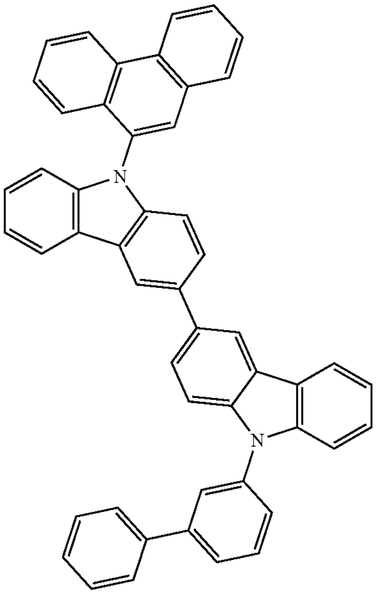
1-22
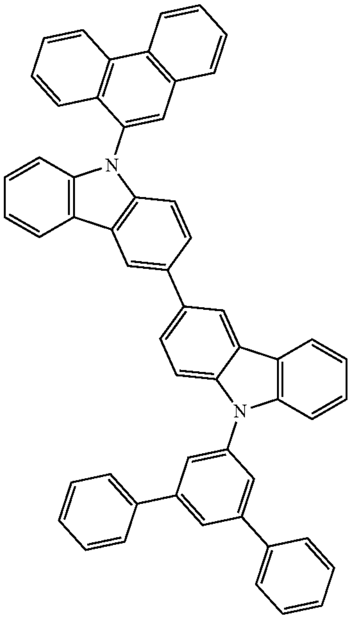

-continued
1-23
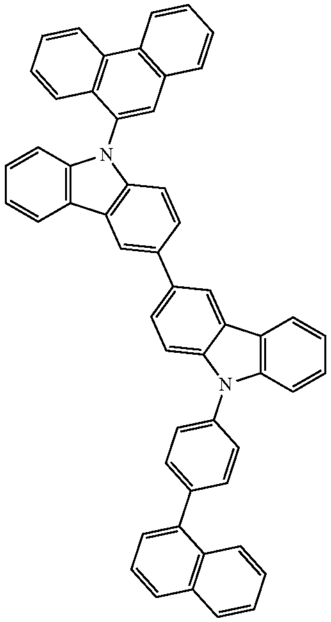
1-24
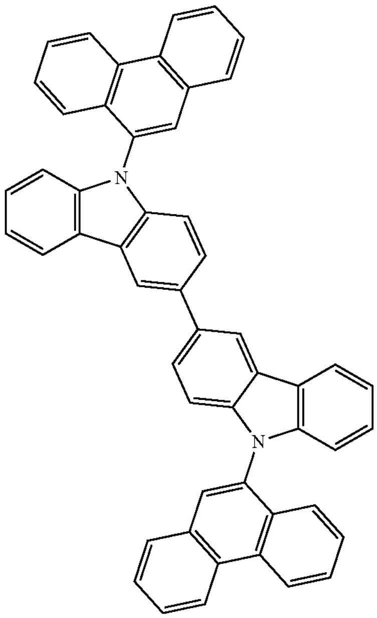
-continued
1-25
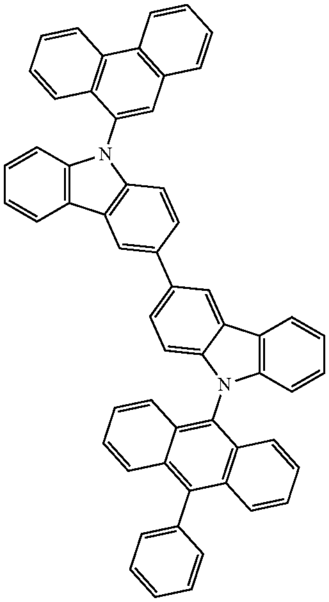
1-26
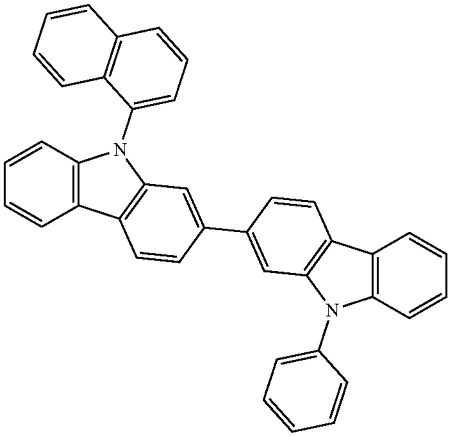
1-27
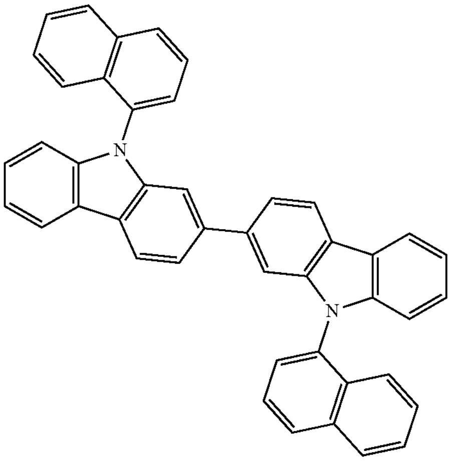

-continued
[Formula 10]
1-28
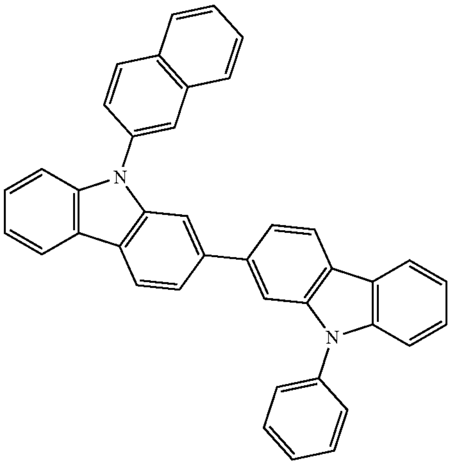
1-29
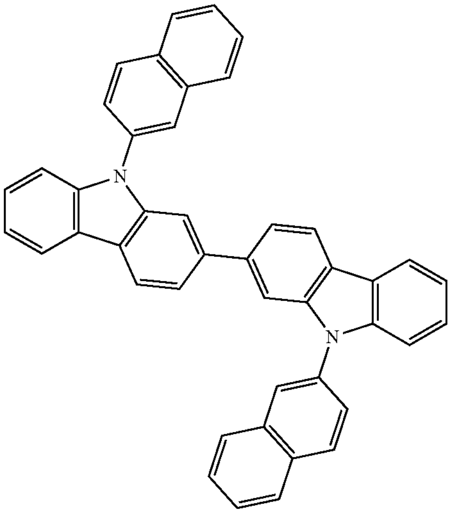
1-30
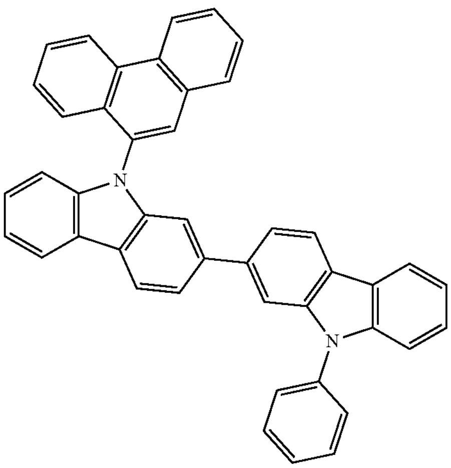
-continued
1-31
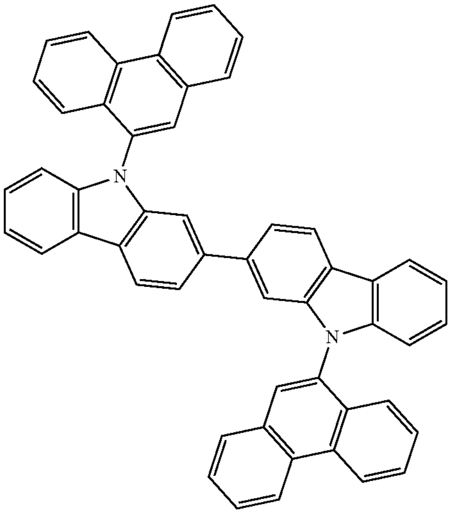
1-32
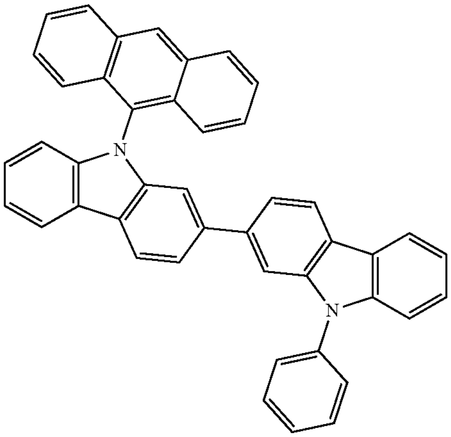
1-33
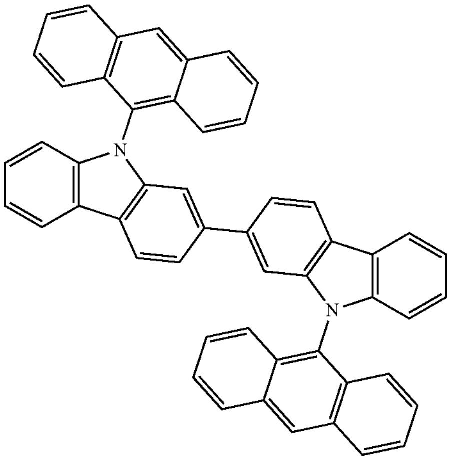

-continued
1-34
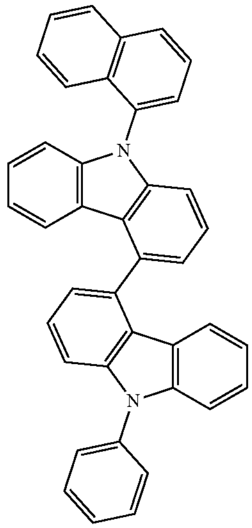
1-35
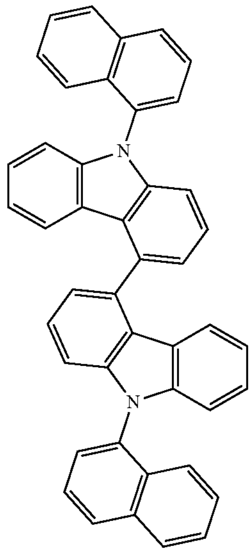
1-36
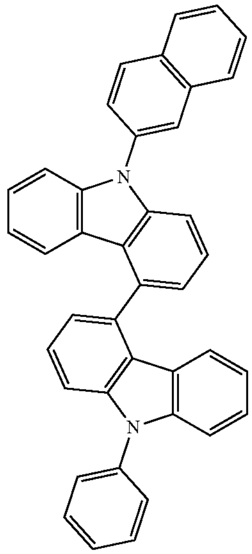
-continued
1-37
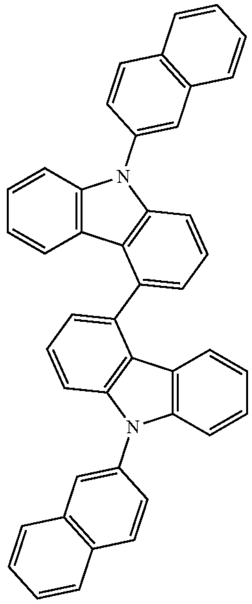
1-38
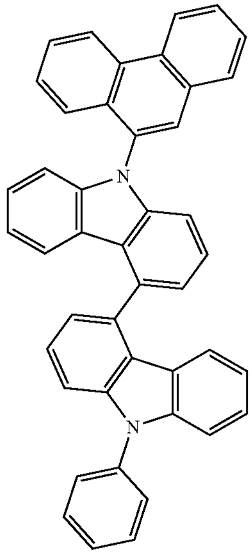

-continued
1-39
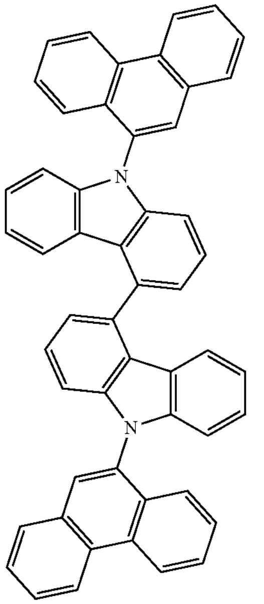
1-40
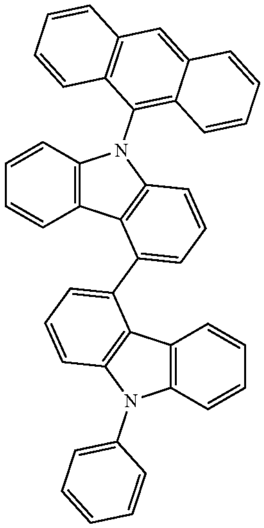
-continued
1-41
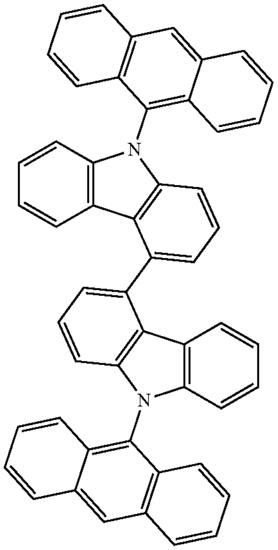
[Formula 11]
1-42
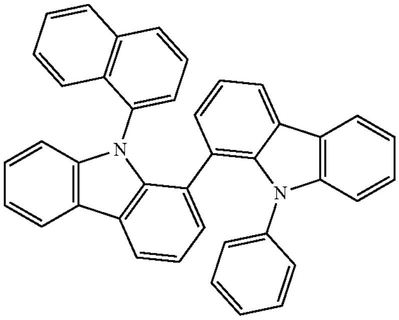
1-43
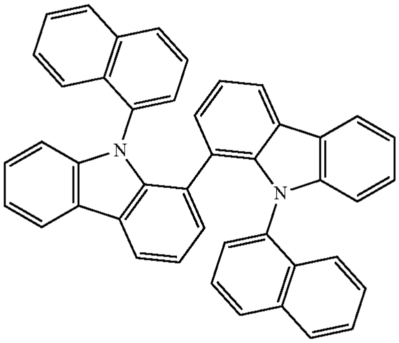
1-44
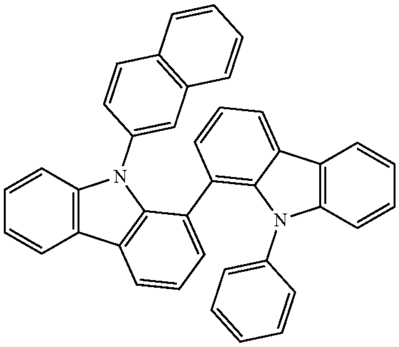

-continued
1-45
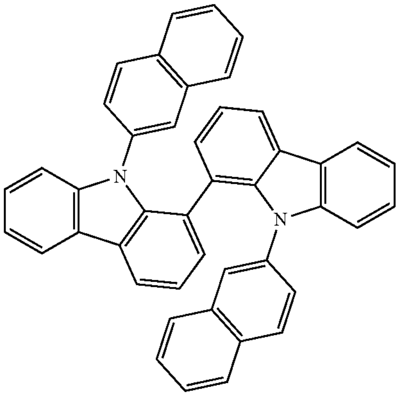
1-46
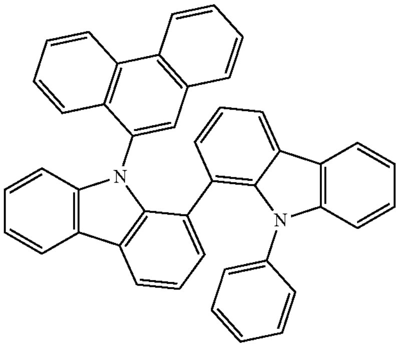
1-47
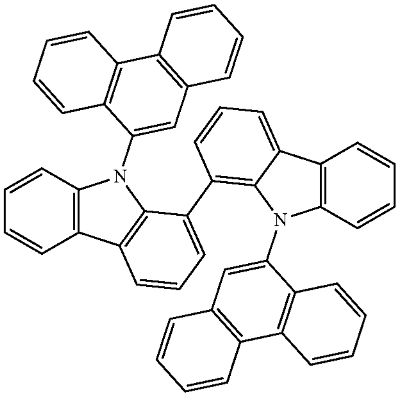
1-48
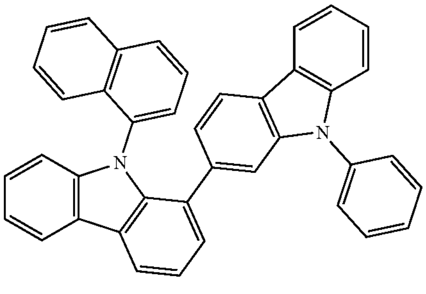
-continued
1-49
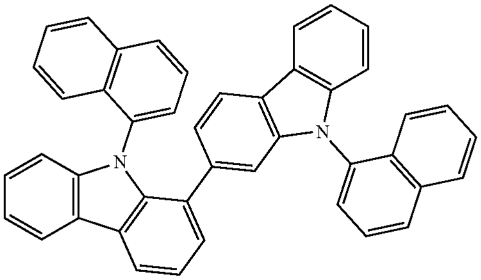
1-50
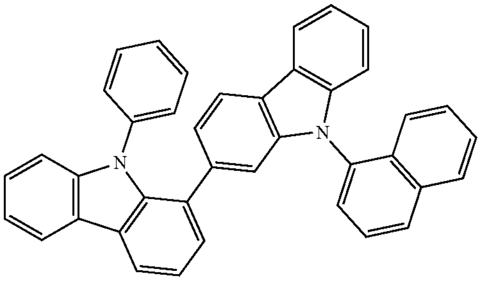
1-51
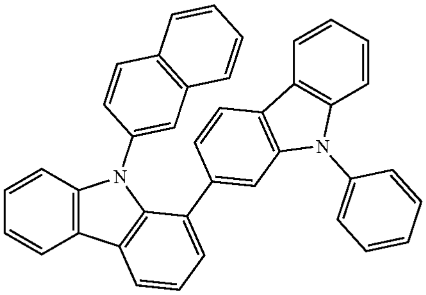
1-52
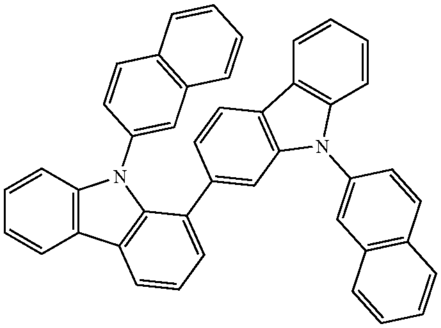
1-53
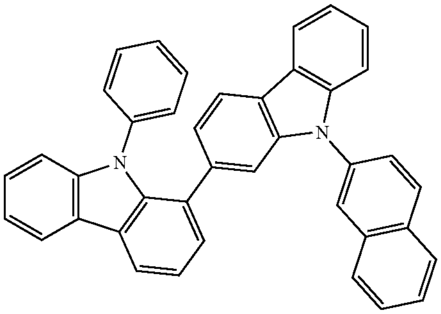

-continued
1-54
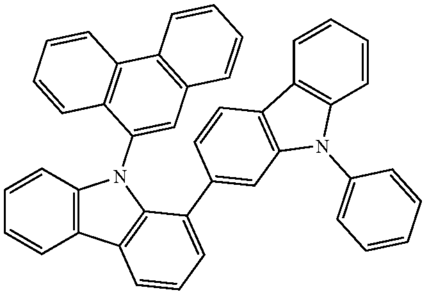
1-55
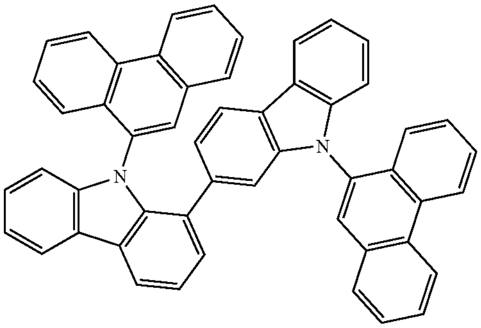
[Formula 12]
1-56
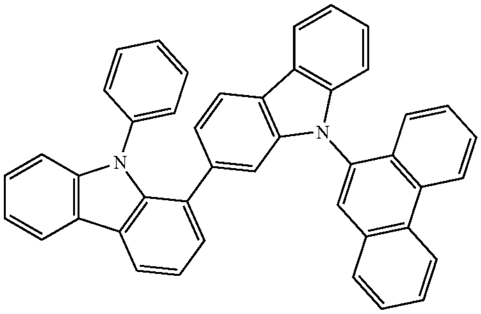
1-57
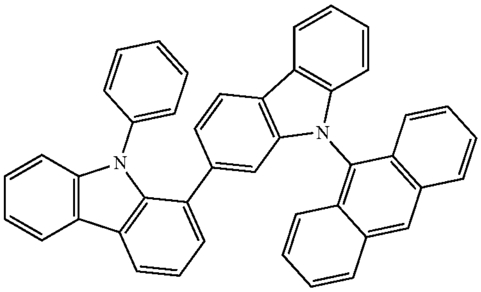
1-58
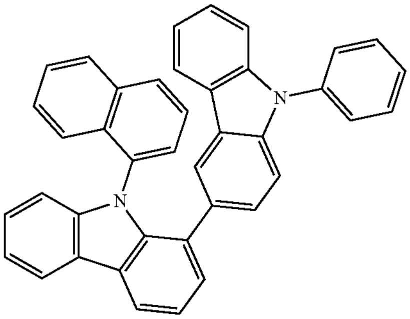
-continued
1-59
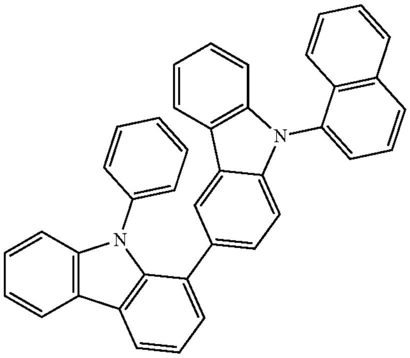
1-60
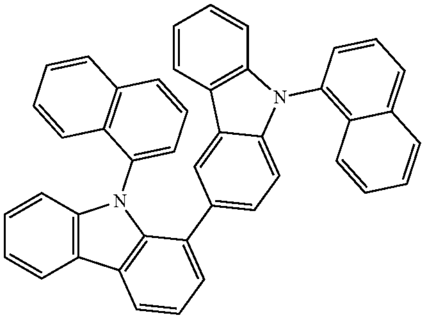
1-61
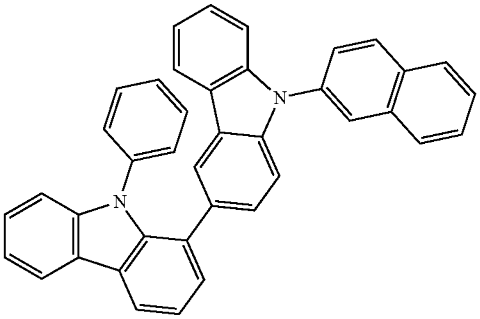
1-62
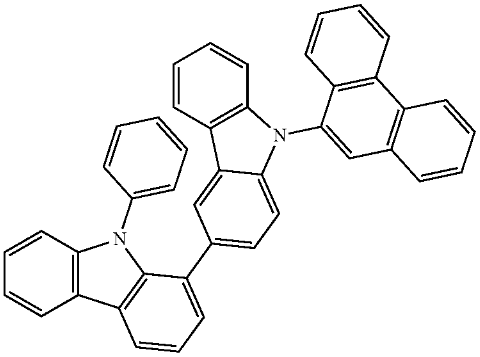

-continued
1-63
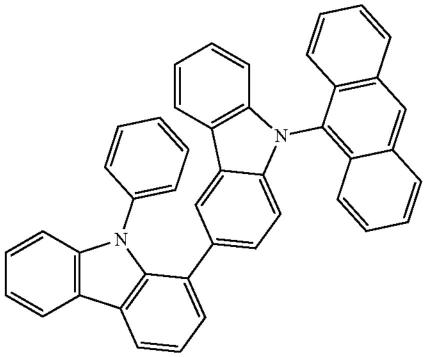
1-64
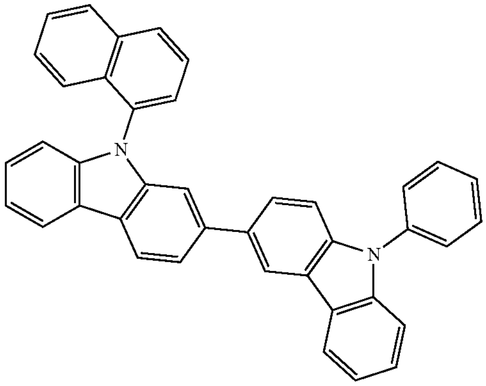
1-65
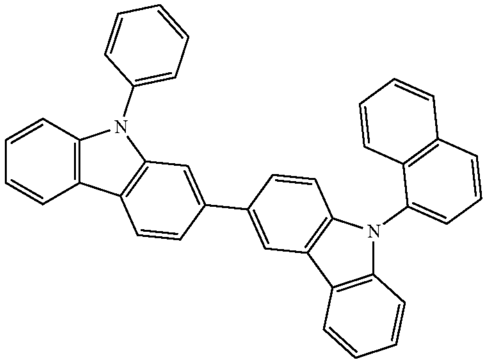
1-66
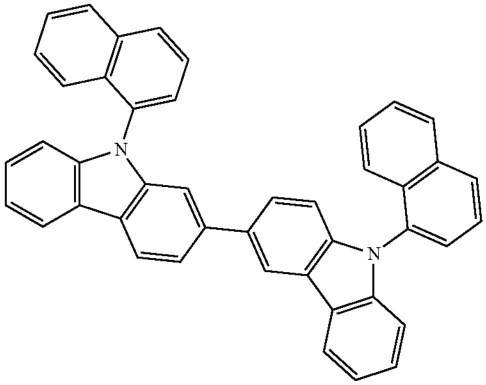
-continued
[Formula 13]
1-67
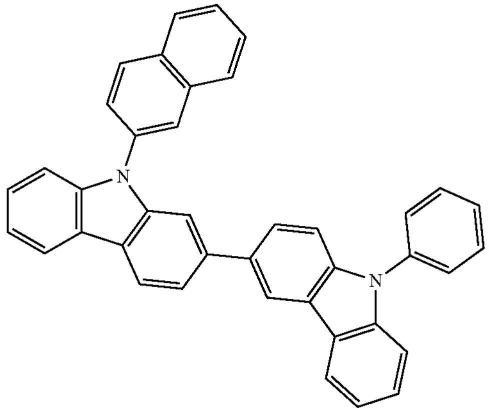
1-68
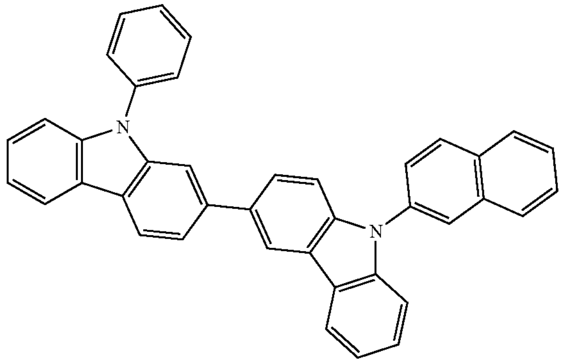
1-69
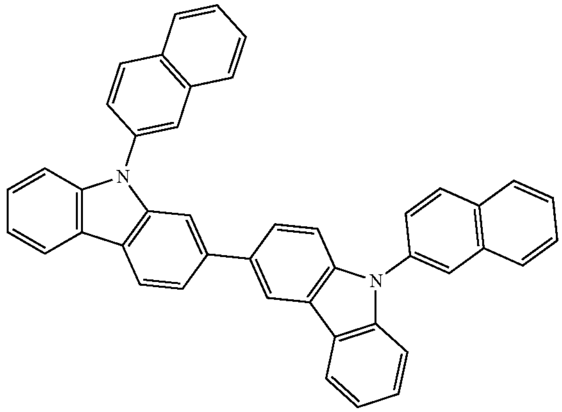

-continued
1-70
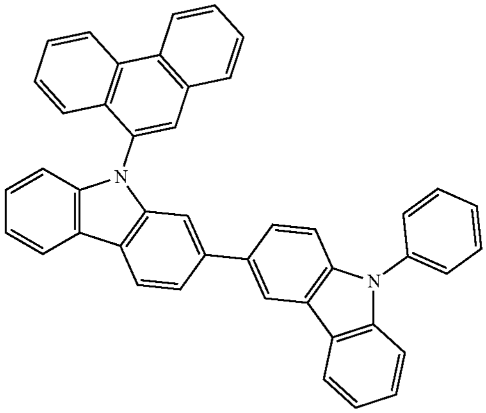
1-71
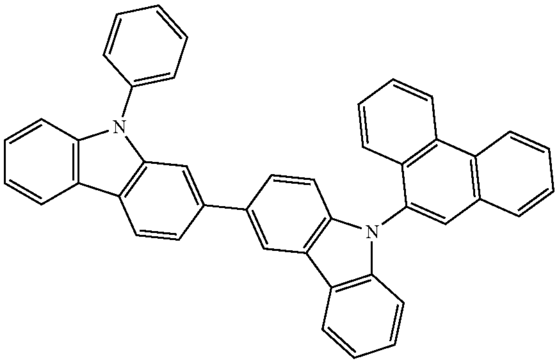
1-72
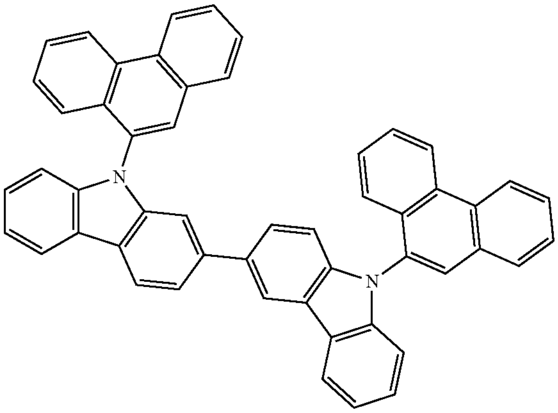
-continued
1-73
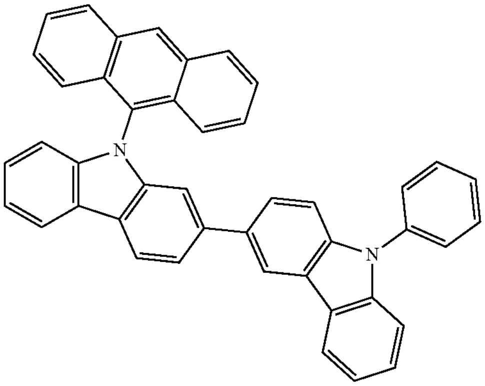
1-74
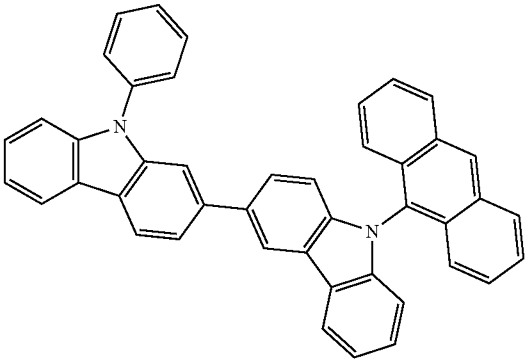
[Formula 14]
1-75
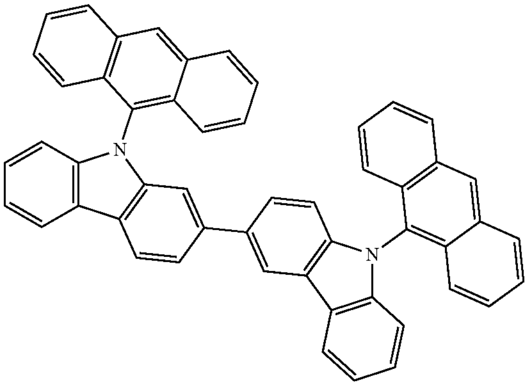

-continued
1-76
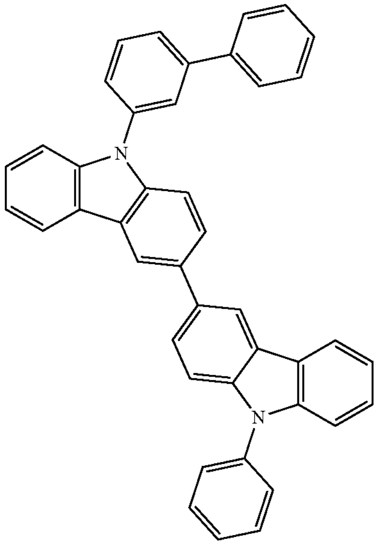
1-77
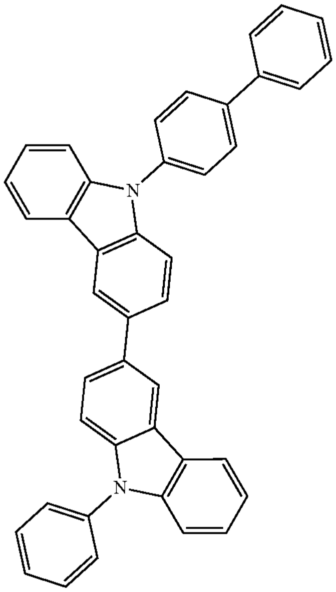
-continued
1-78
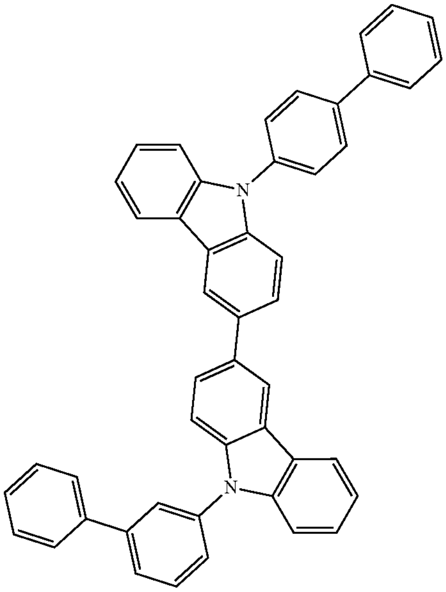
1-79
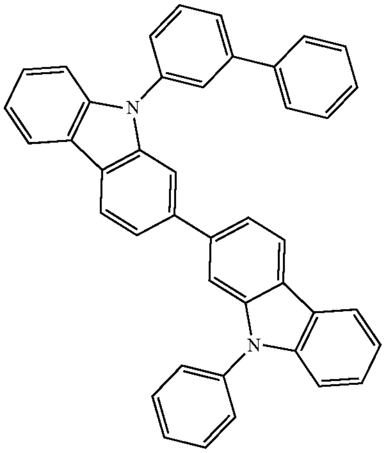
1-80
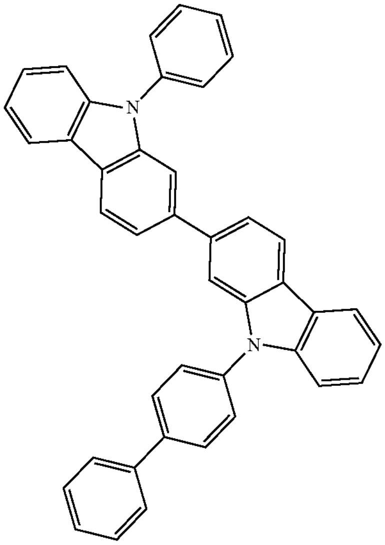

-continued
[Formula 15]
1-81
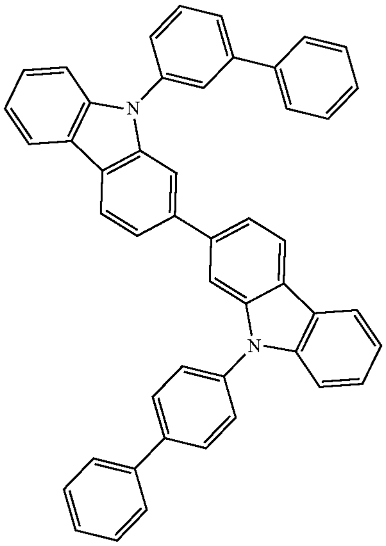
1-82
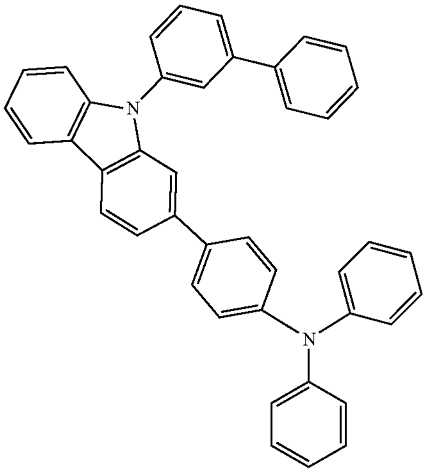
1-83
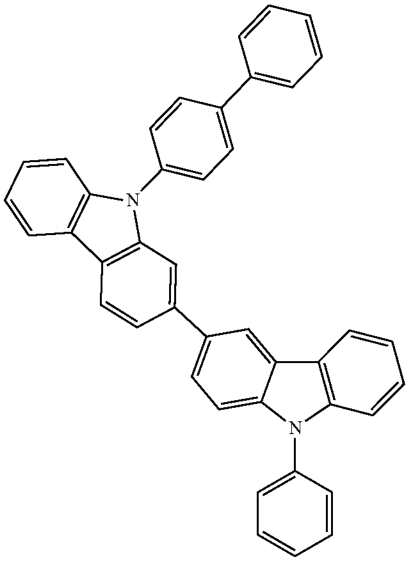
-continued
1-84
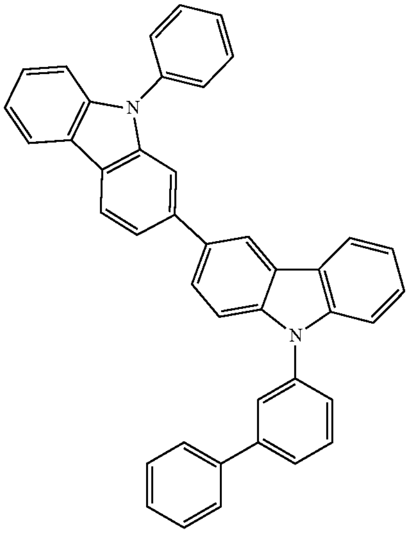
1-85
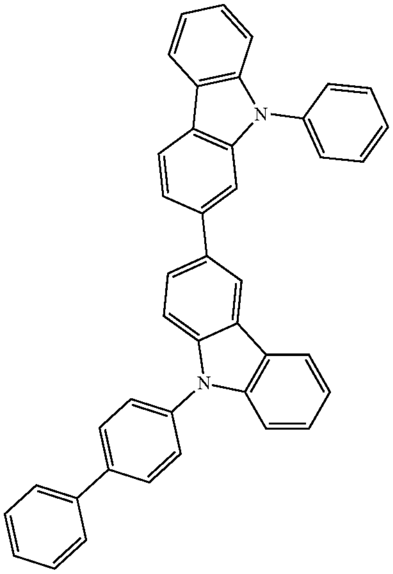

-continued
[Formula 16]
1-86
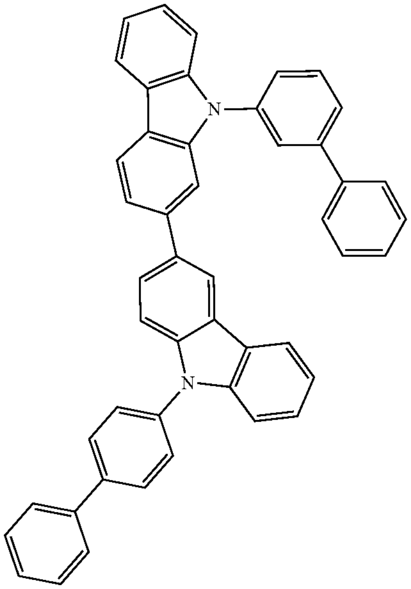
1-87
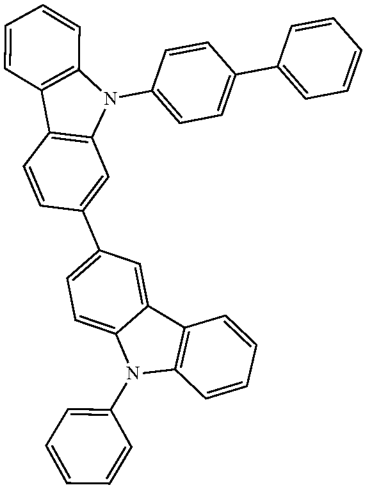
1-88
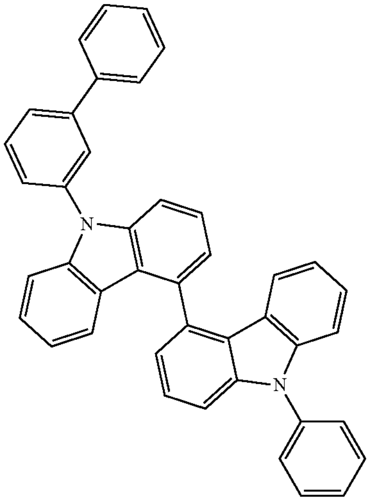
-continued
1-89
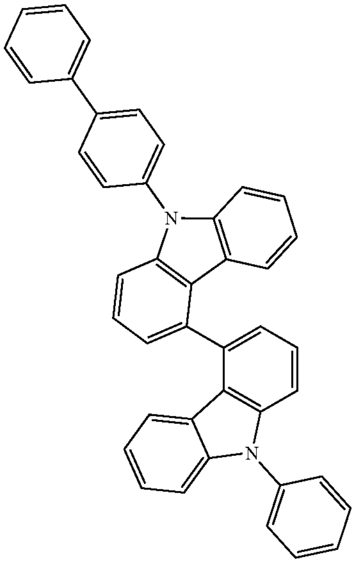
1-90
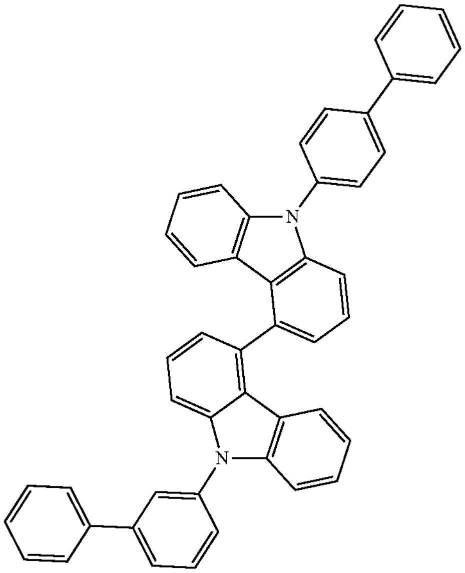
[Formula 17]
1-91
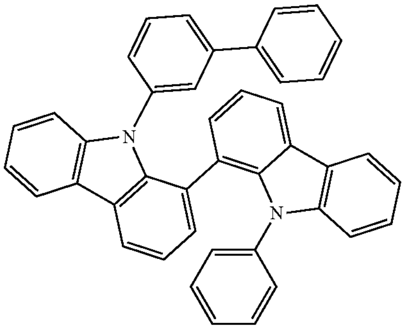

-continued
1-92
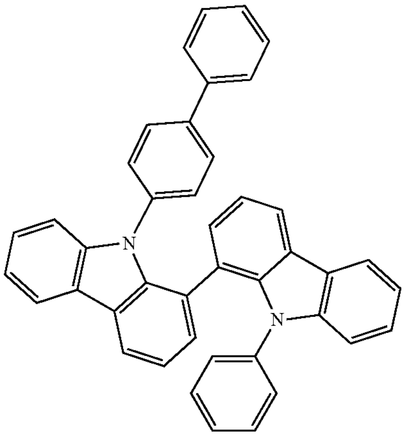
1-93
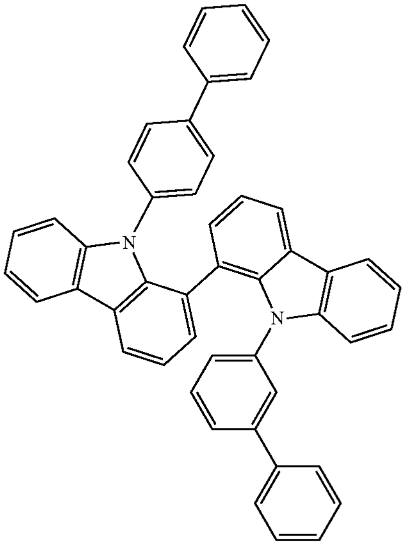
1-94
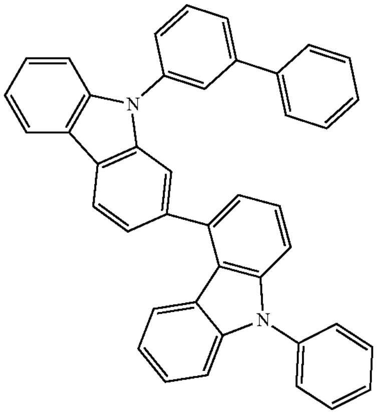
-continued
1-95
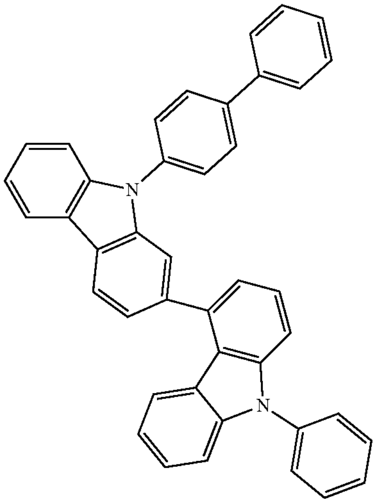
1-96
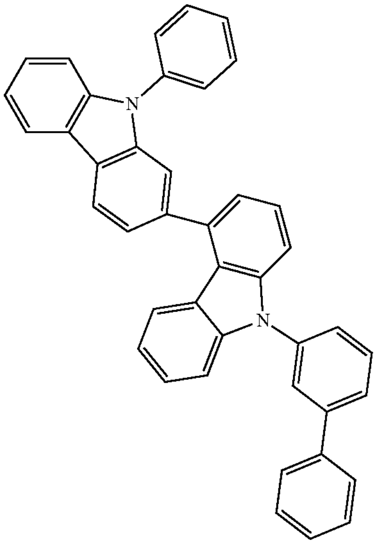
1-97
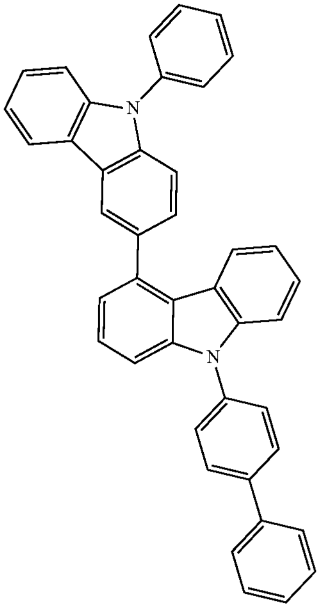

-continued
[Formula 18]
1-98
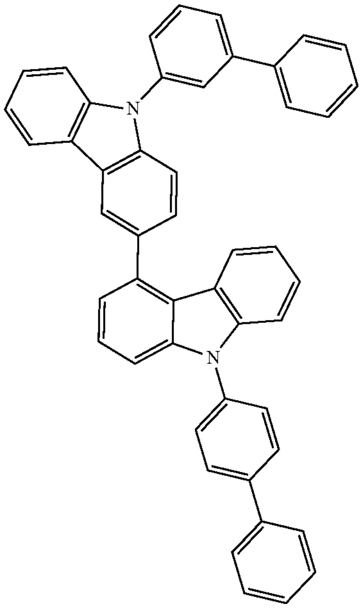
1-99
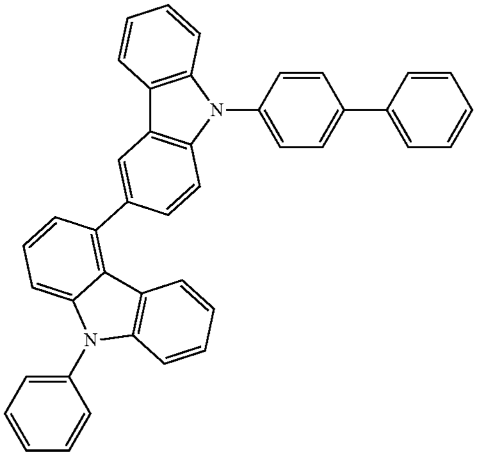
1-100
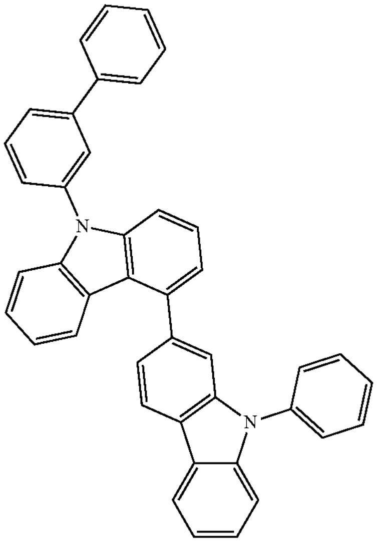
-continued
1-101
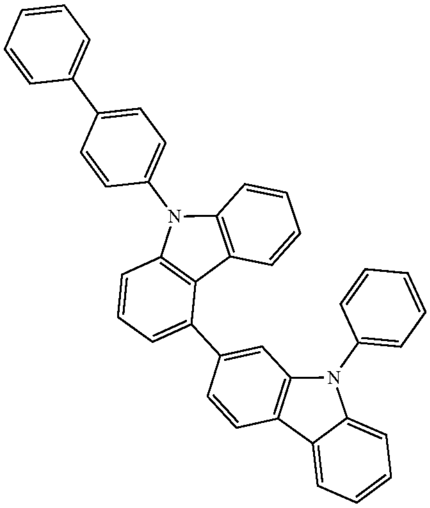
1-102
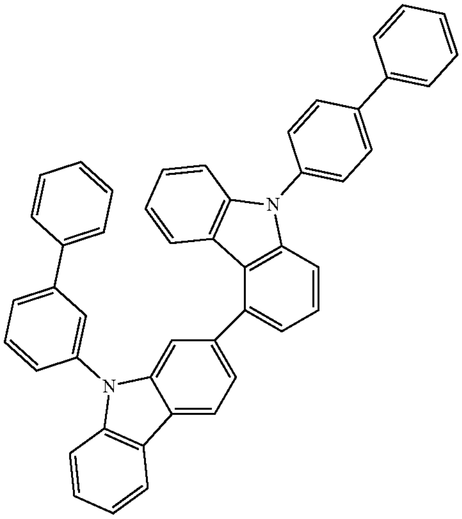
[Formula 19]
1-103
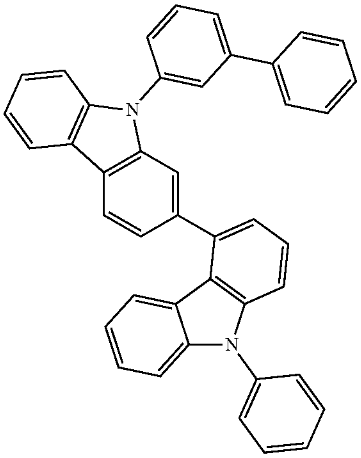

-continued
1-104
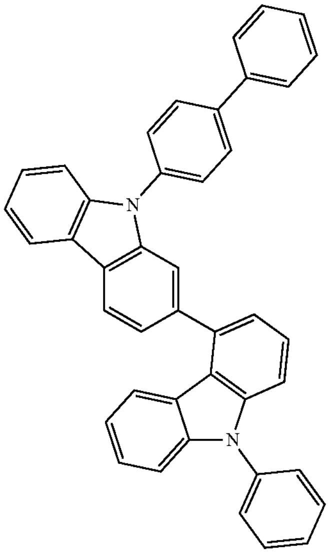
1-105
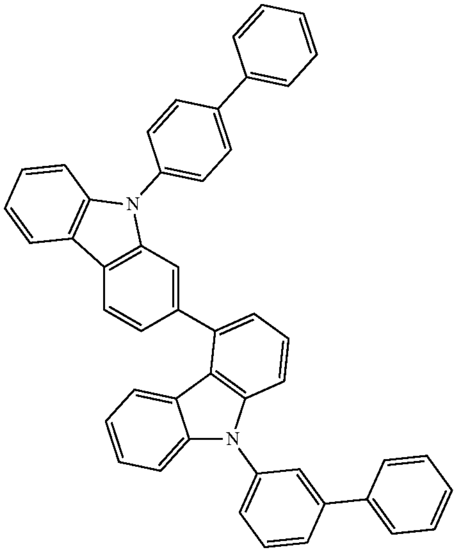
1-106
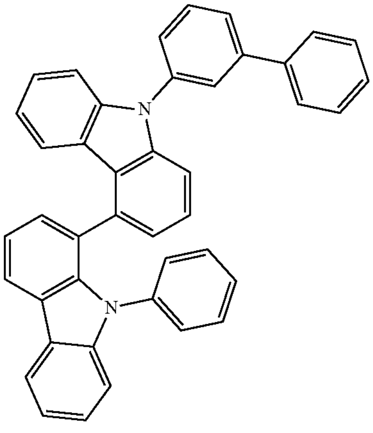
-continued
1-107
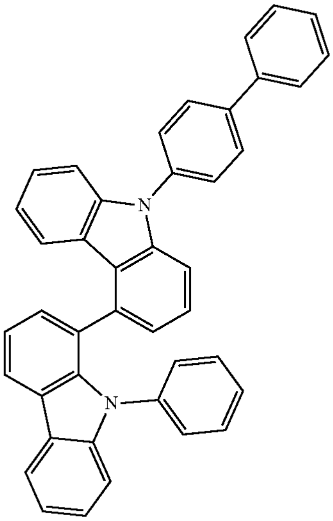
1-108
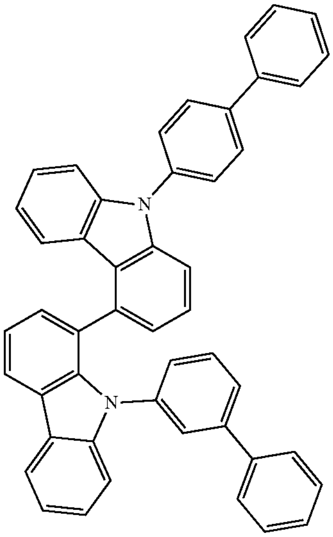
[Formula 20]
1-109
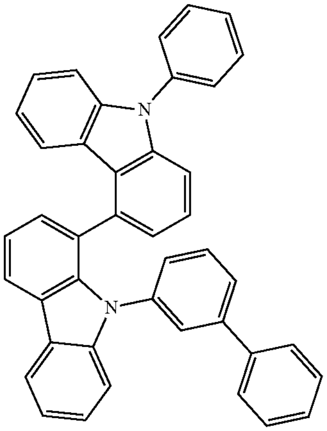

-continued
1-110
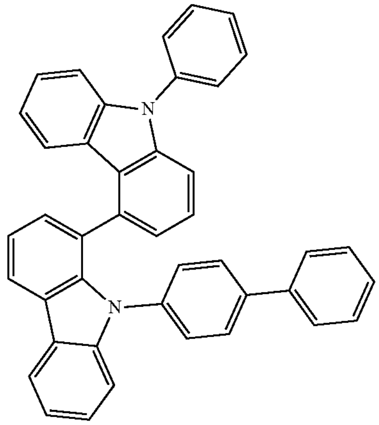
1-111
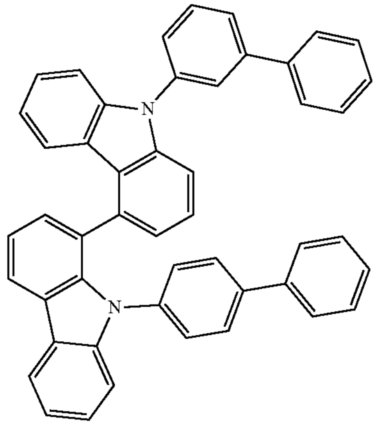
1-112
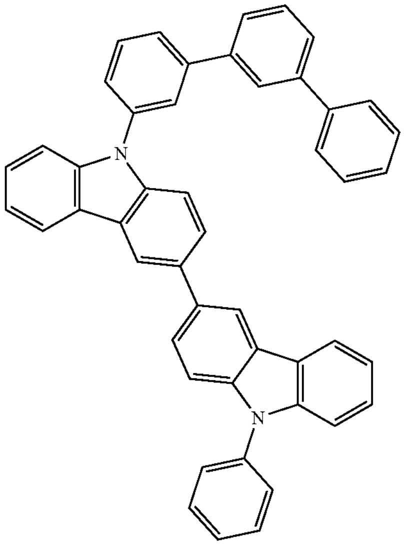
-continued
1-113
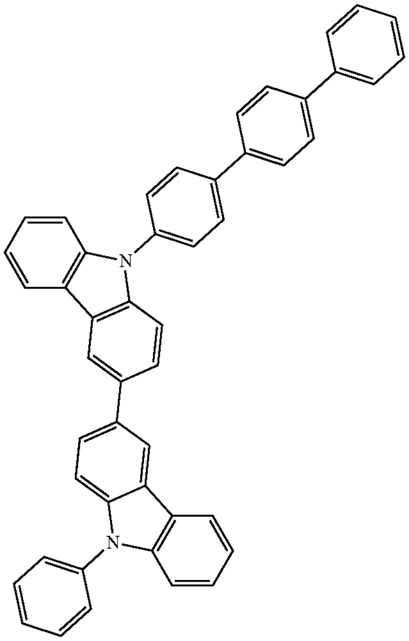
[Formula 21]
1-114
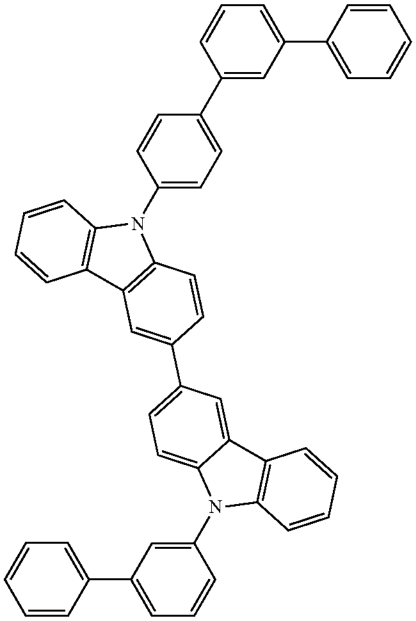

-continued
1-115
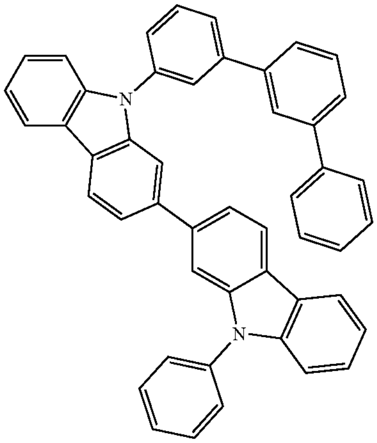
1-116
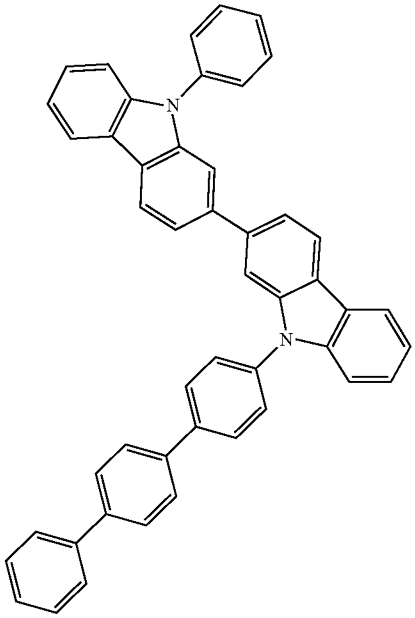
1-117
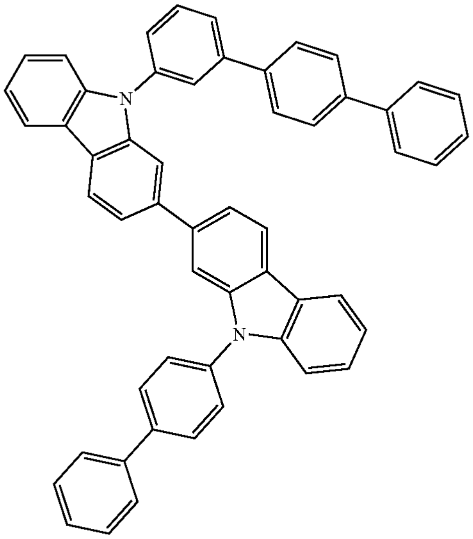
-continued
1-118
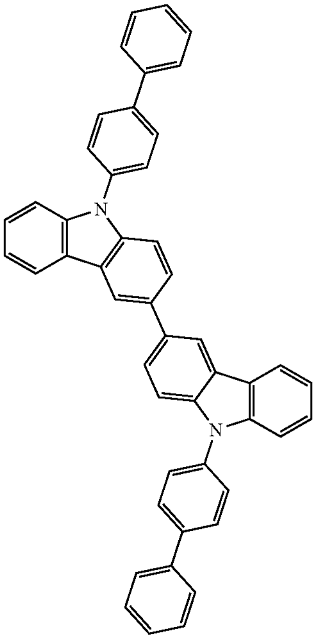
1-119
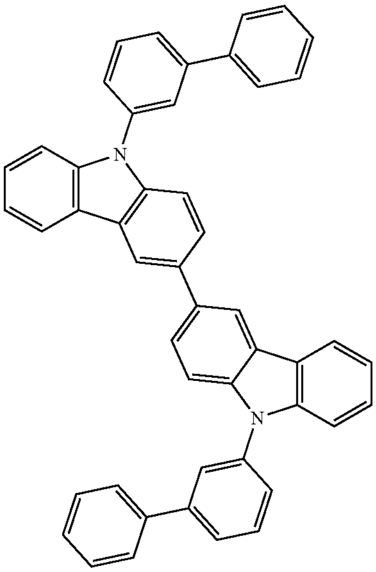

-continued
[Formula 22]
1-120
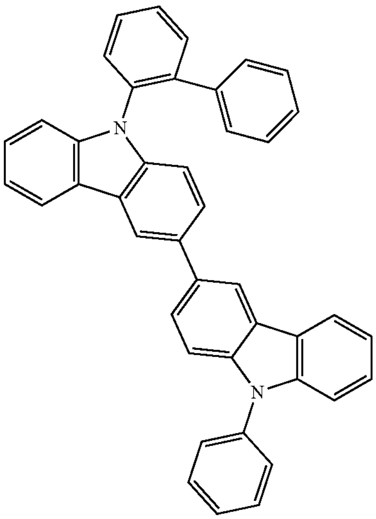
1-121
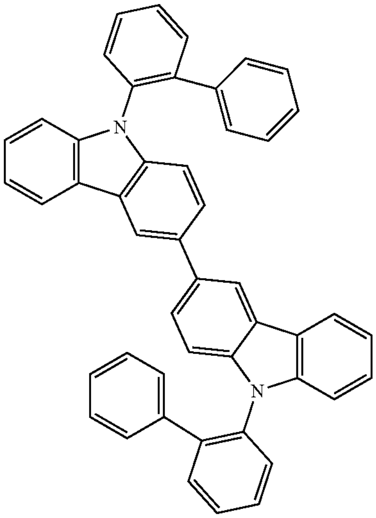
1-122
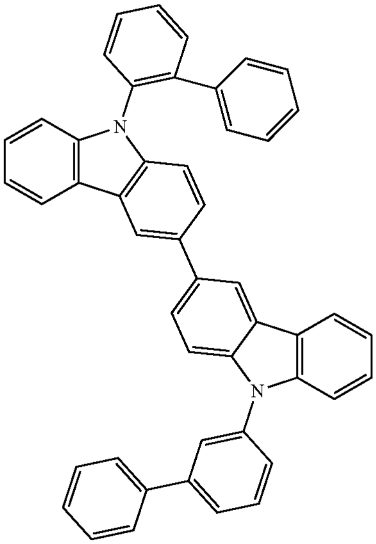
-continued
1-123
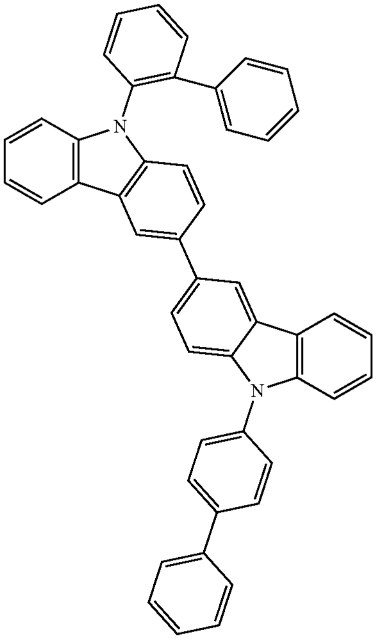
1-124
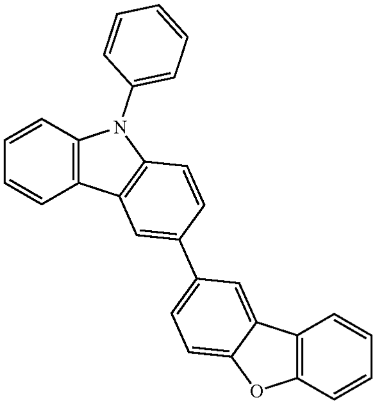
1-125
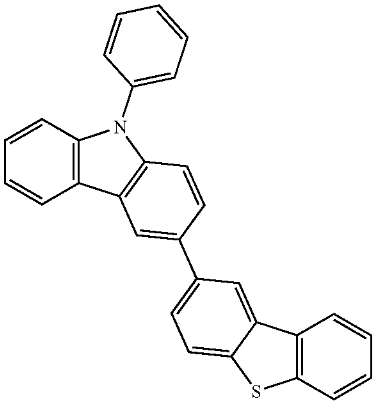

-continued
[Formula 23]
1-126
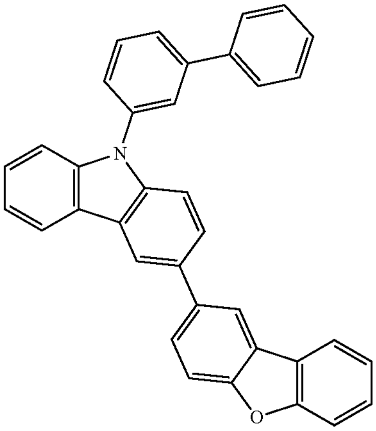
1-127
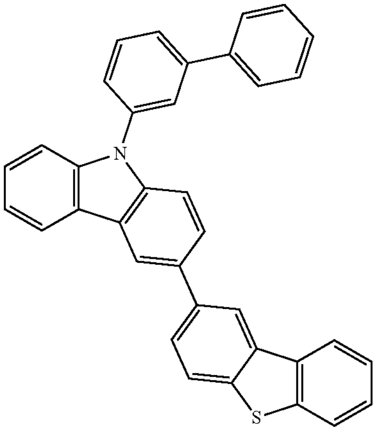
1-128
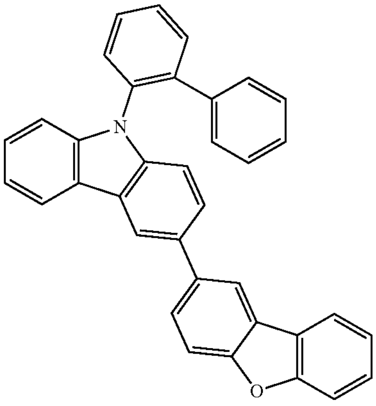
-continued
1-129
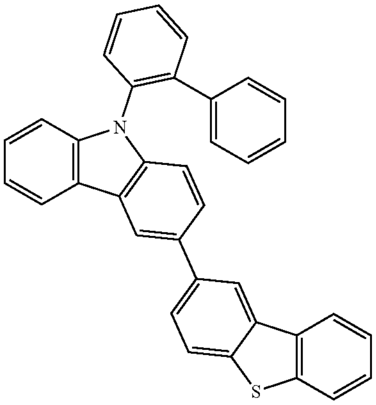
1-130
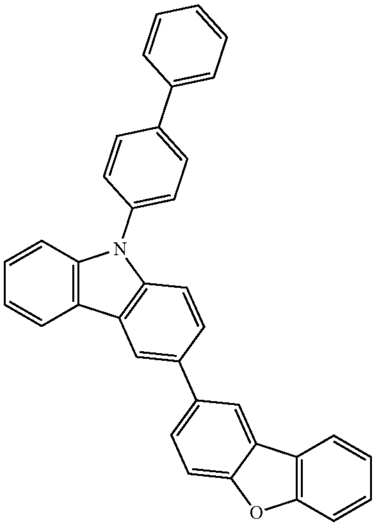
[Formula 24]
1-131
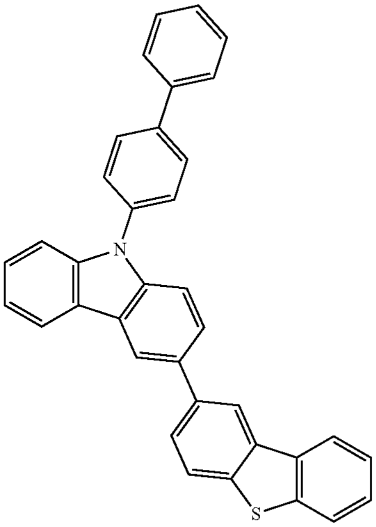

-continued
1-132
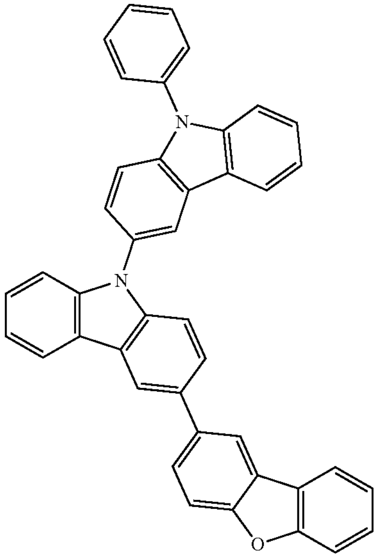
1-133
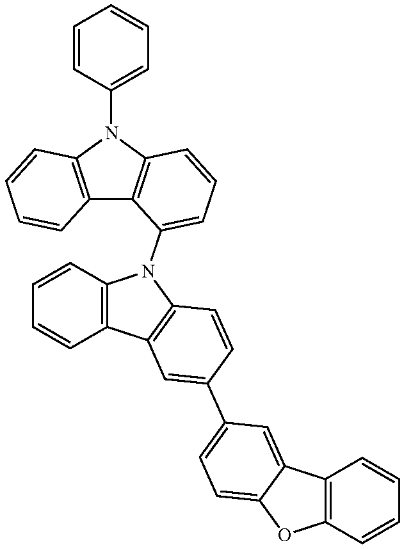
1-134
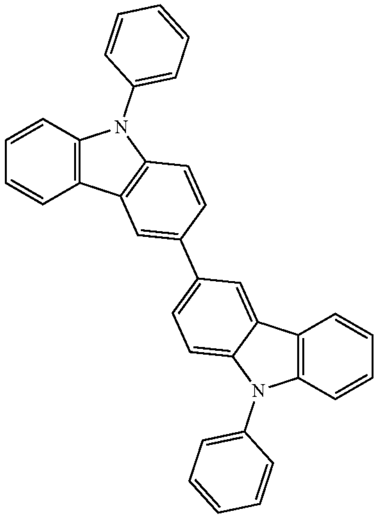
-continued
1-135
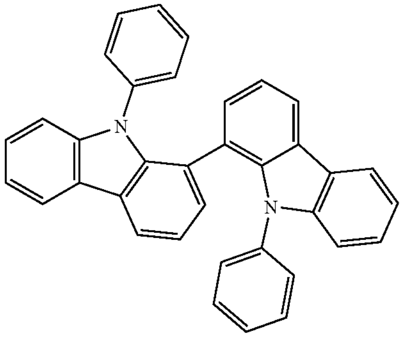
1-136
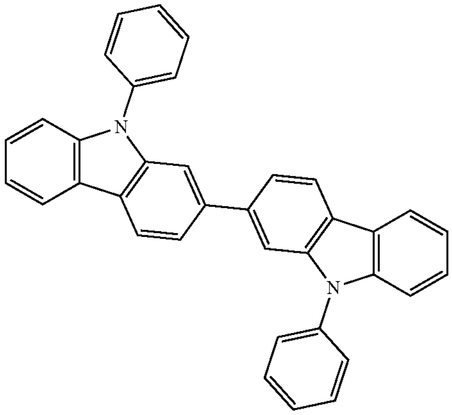
[Formula 25]
1-137
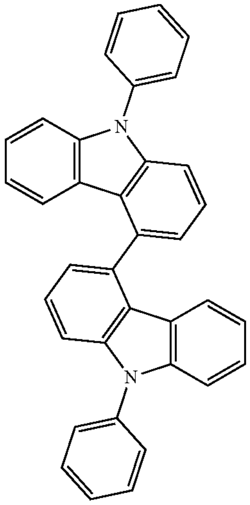
1-138
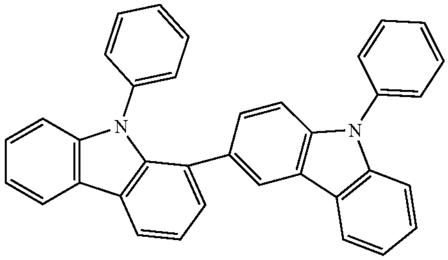

-continued 1-139

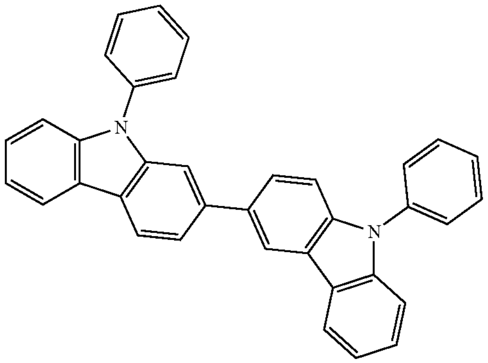

1-140

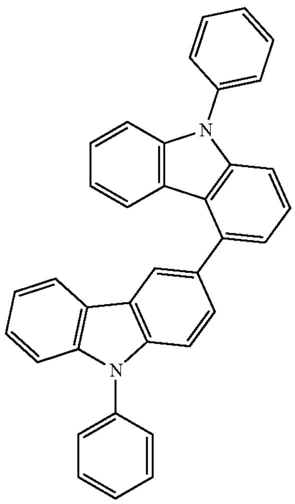

The compound represented by the general formula (2) used in the present invention as the second host will be described.

$X^2$ independently represents N or C—H, and at least two $X^2$ represent N. Preferably three $X^2$ represent N.

Are represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof.

Preferably, $Ar^2$ represents a substituted or unsubstituted aromatic hydrocarbon group having 6 to 12 carbon atoms, a substituted or unsubstituted aromatic heterocyclic group having 3 to 12 carbon atoms, or a substituted or unsubstituted linked aromatic group formed by linking 2 to 6 aromatic rings thereof.

More preferably, $Ar^2$ represents a substituted or unsubstituted aromatic hydrocarbon group having 6 to 10 carbon atoms, a substituted or unsubstituted aromatic heterocyclic group having 3 to 10 carbon atoms, or a substituted or unsubstituted linked aromatic group formed by linking 2 to 4 aromatic rings thereof.

Specific examples of the unsubstituted $Ar^2$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracenepyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 8 of these compounds.

Preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 6 of these compounds.

More preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, and a compound formed by linking 2 to 4 of these compounds.

Each of these aromatic hydrocarbon groups, aromatic heterocyclic groups, and linked aromatic groups may have a substituent. When these groups have a substituent, the substituent is a cyano group, an aliphatic hydrocarbon group having 1 to 10 carbon atoms, a diarylamino group having 12 to 44 carbon atoms, or a triphenylsilyl group. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino. Preferred examples thereof include cyano, methyl, ethyl, propyl, butyl, pentyl, hexyl, heptyl, octyl, diphenylamino, naphthylphenylamino, and dinaphthylamino.

$R^2$ independently represents deuterium, an aliphatic hydrocarbon group having 1 to 10 carbon atoms, a substituted or unsubstituted aromatic hydrocarbon group having 6 to 18 carbon atoms, a substituted or unsubstituted aromatic heterocyclic group having 3 to 17 carbon atoms, or a triphenylsilyl group. Preferably, $R^2$ is a substituted or unsubstituted aromatic hydrocarbon group having 6 to 12 carbon atoms, or a substituted or unsubstituted aromatic heterocyclic group having 3 to 15 carbon atoms. More preferably, $R^2$ is an aromatic hydrocarbon group having 6 to 10 carbon atoms. e, f, g, and h represent an integer of 0 to 4.

When $R^2$ represents an aliphatic hydrocarbon group having 1 to 10 carbon atoms, specific examples of $R^2$ include, methyl, ethyl, propyl, butyl, pentyl, hexyl, heptyl, octyl, and nonyl.

When $R^2$ represents an unsubstituted aromatic hydrocarbon group having 6 to 18 carbon atoms or an unsubstituted aromatic heterocyclic group having 3 to 17 carbon atoms, specific examples of $R^2$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

Preferred examples thereof include a group produced by removing one hydrogen atom from benzene, naphthalene, acenaphthene, acenaphthylene, azulene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

More preferred examples thereof include a group produced by removing one hydrogen atom from benzene or naphthalene.

Each of these aromatic hydrocarbon groups and aromatic heterocyclic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino. Preferred examples thereof include cyano, methyl, ethyl, propyl, butyl, pentyl, hexyl, heptyl, octyl, diphenylamino, naphthylphenylamino, and dinaphthylamino.

Specific examples of the compounds represented by the general formula (2) are shown below, but the compounds are not limited to these exemplified compounds.

[Formula 26]

2-1

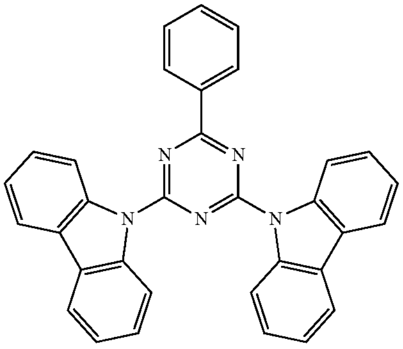

2-2

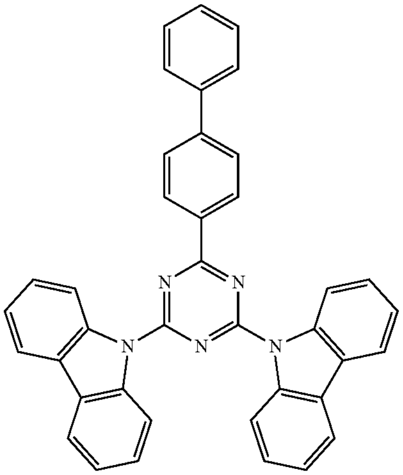

2-3

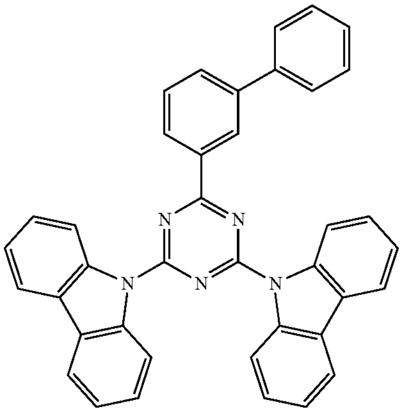

2-4

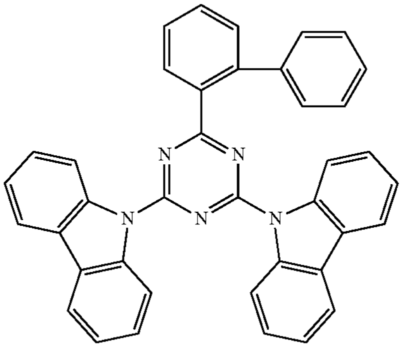

-continued
2-5
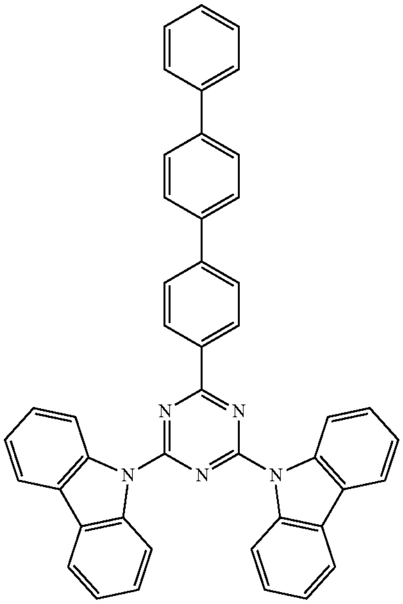
2-6
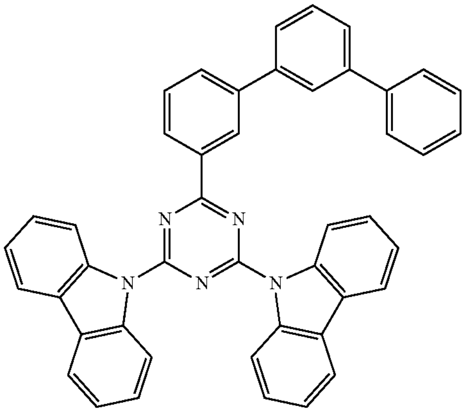
[Formula 27]
2-7
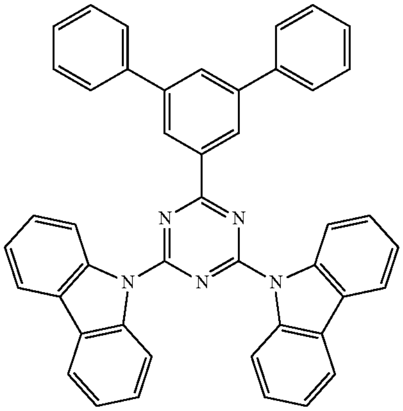
-continued
2-8
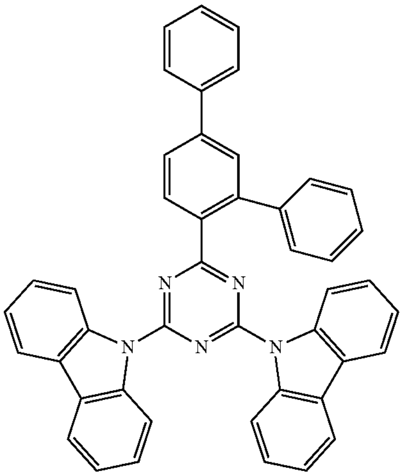
2-9
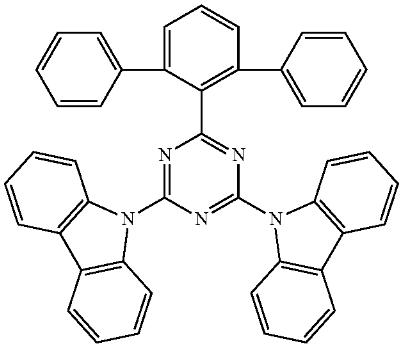
2-10
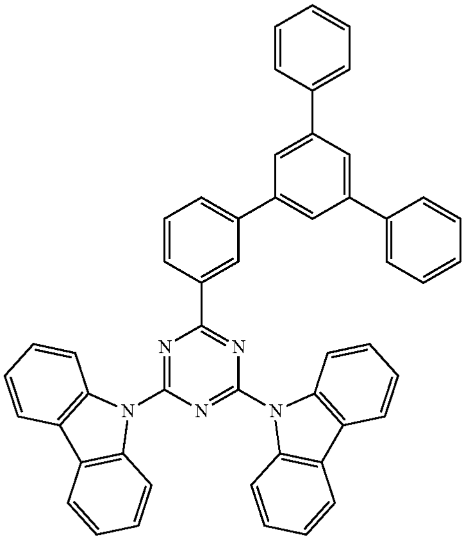

-continued
2-11
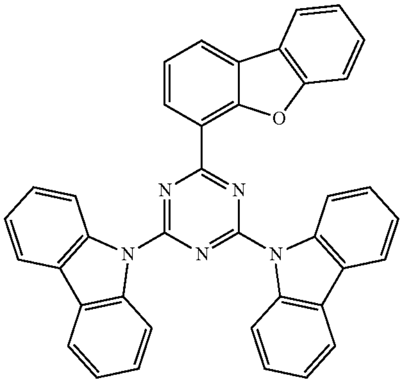
2-12
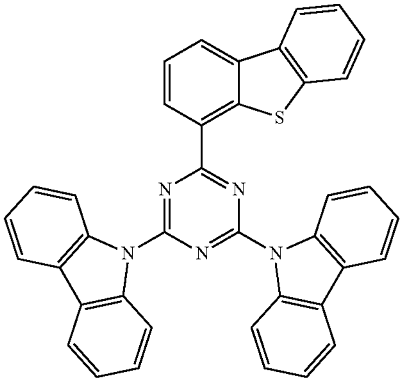
[Formula 28]
2-13
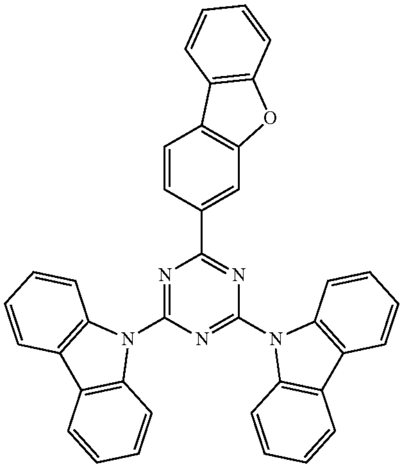
-continued
2-14
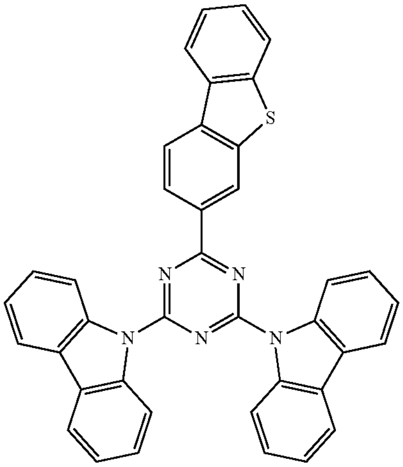
2-15
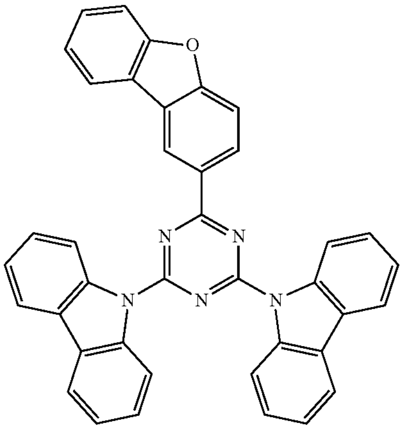
2-16
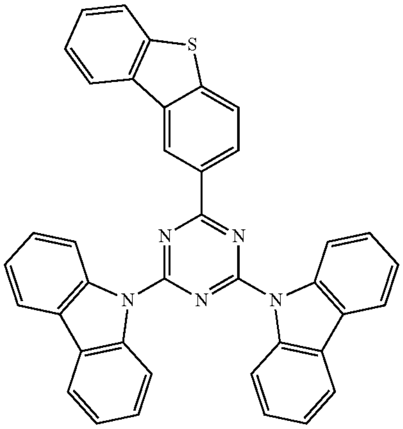

-continued
2-17
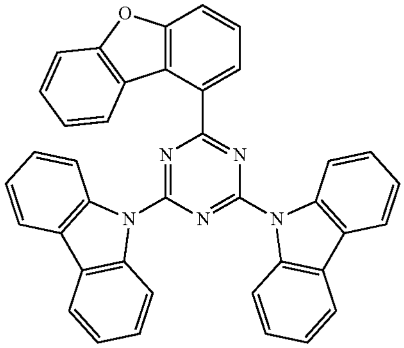
2-18
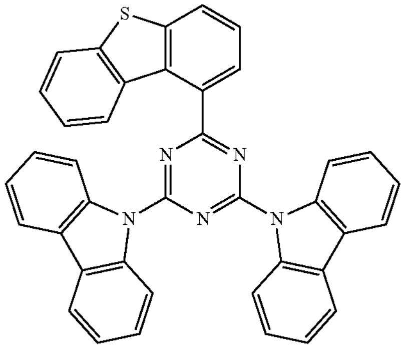
[Formula 29]
2-19
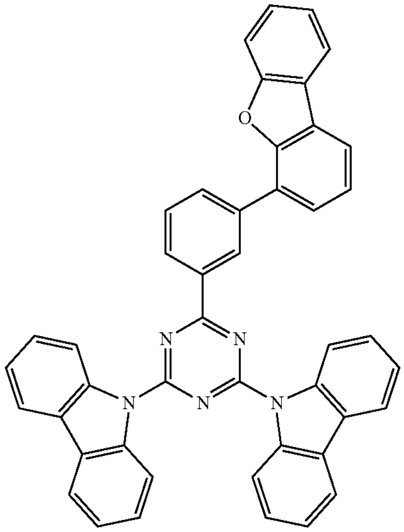
-continued
2-20
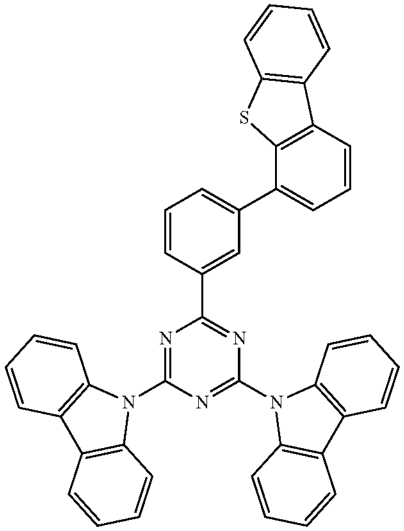
2-21
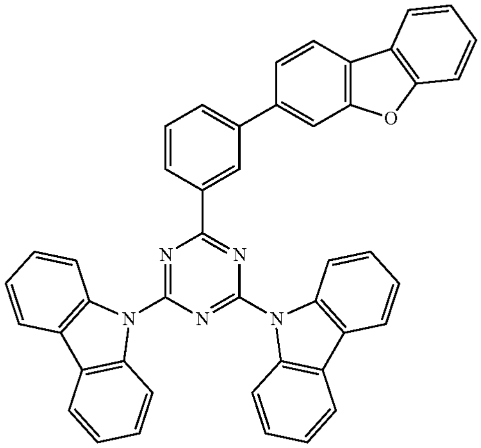
2-22
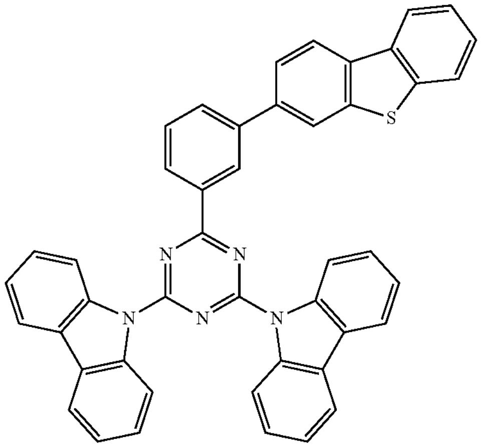

-continued
2-23
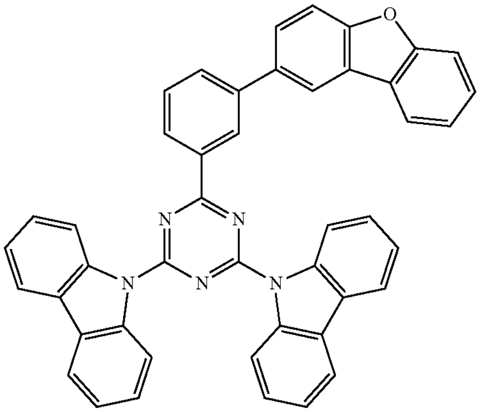
2-24
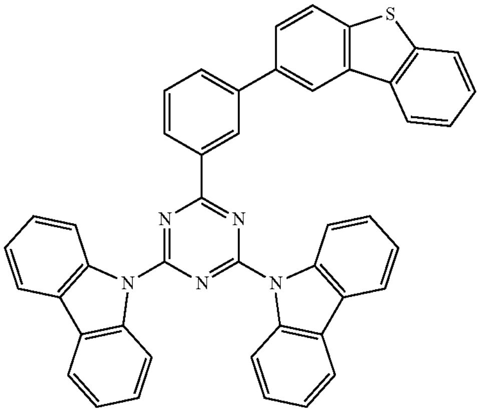
[Formula 30]
2-25
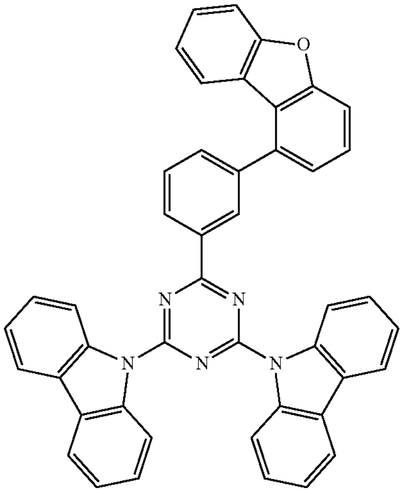
-continued
2-26
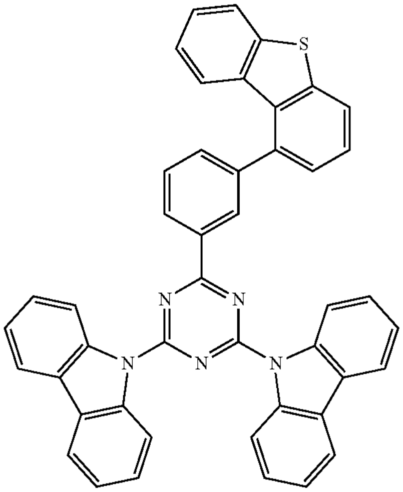
2-27
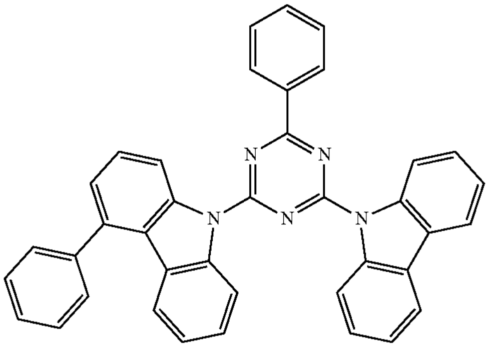
2-28
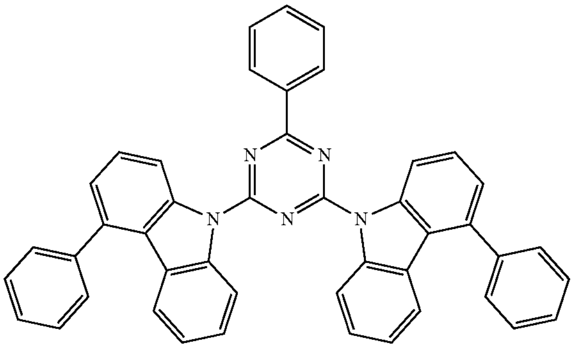

-continued
2-29
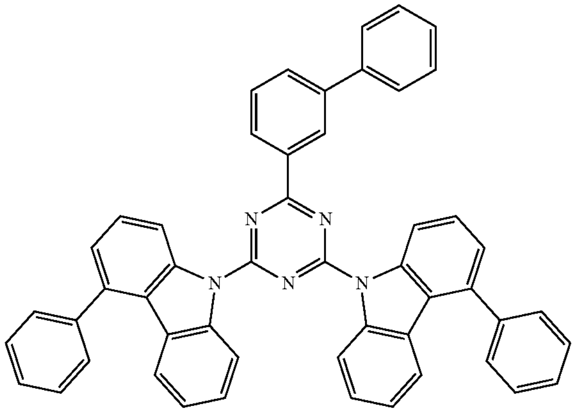
2-30
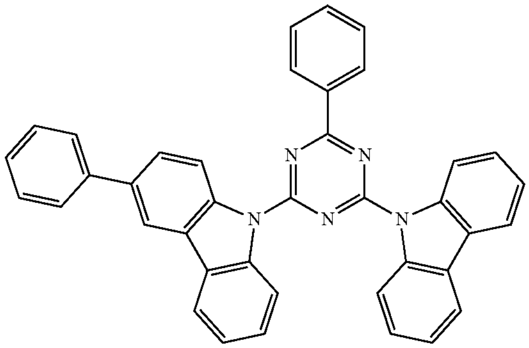
[Formula 31]
2-31
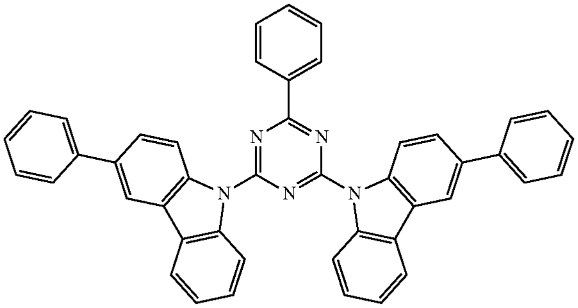
2-32
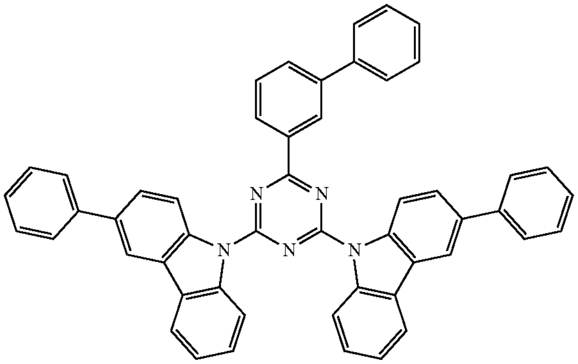
-continued
2-33
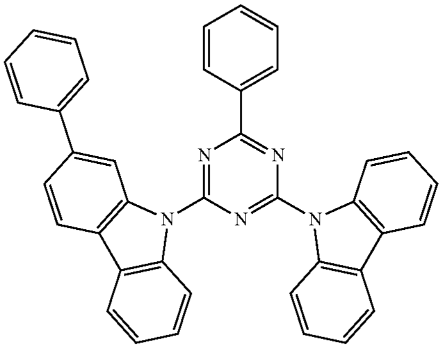
2-34
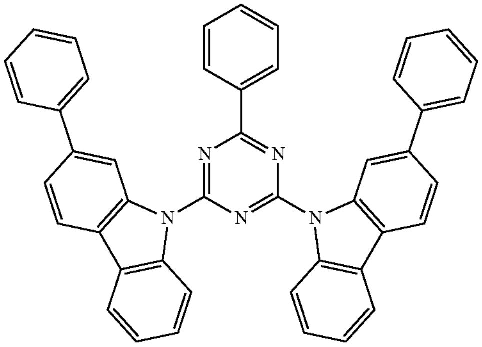
2-35
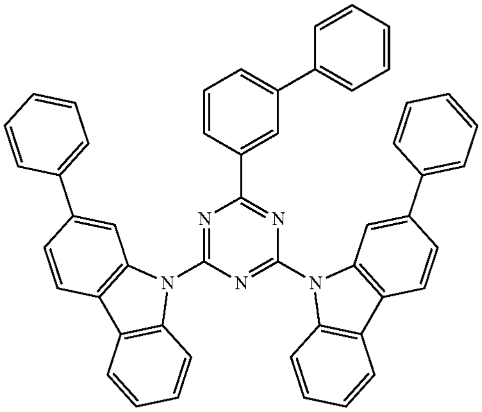
2-36
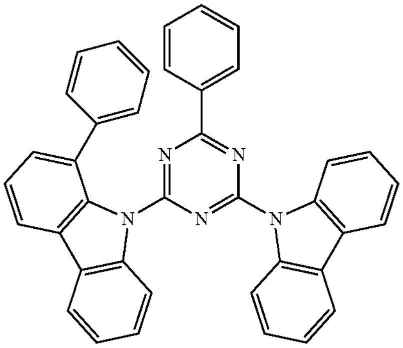

-continued
[Formula 32]
2-37
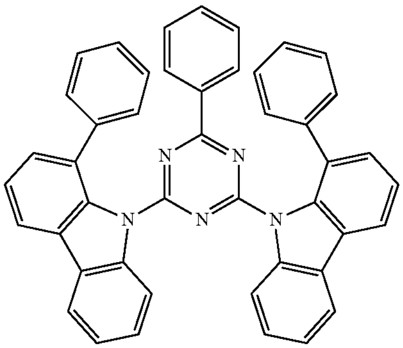
2-38
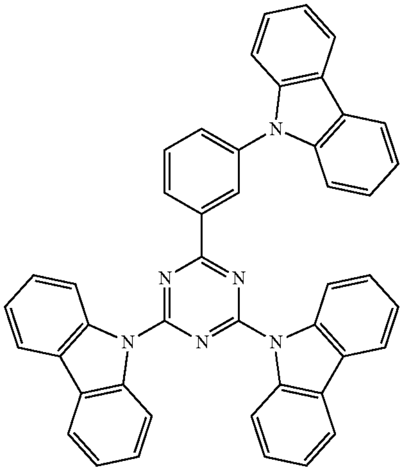
2-39
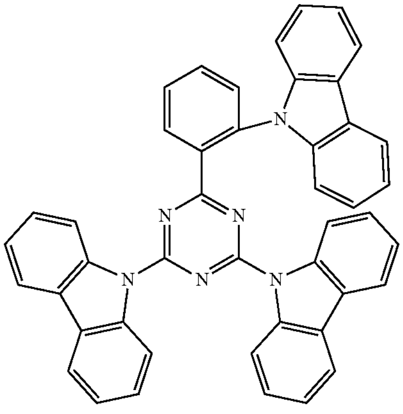
2-40
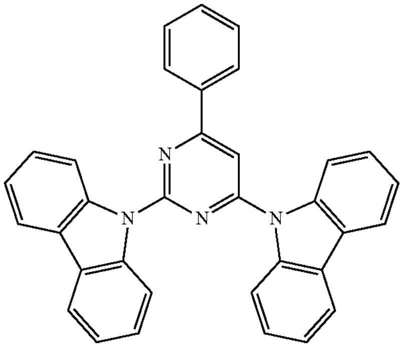
-continued
2-41
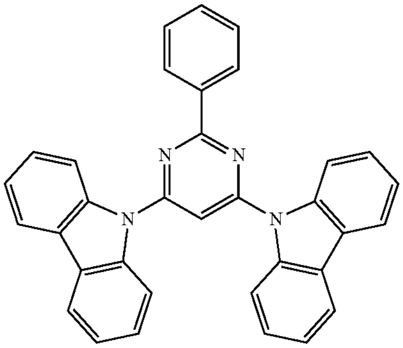
2-42
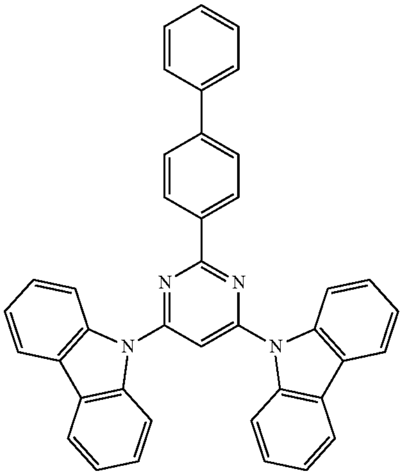
[Formula 33]
2-43
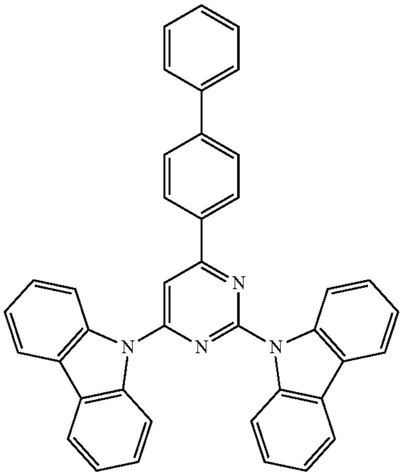

-continued
2-44
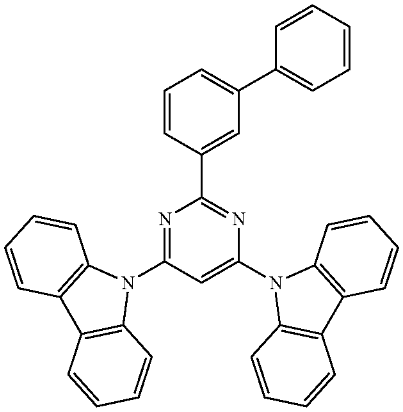
2-45
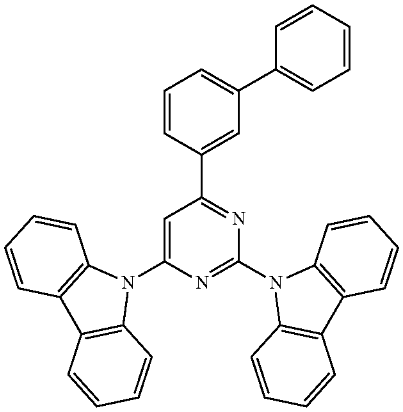
2-46
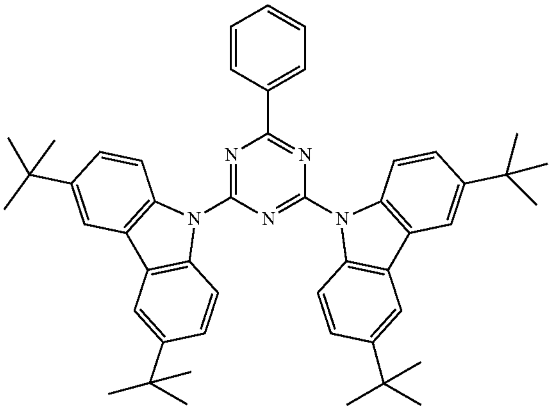
-continued
2-47
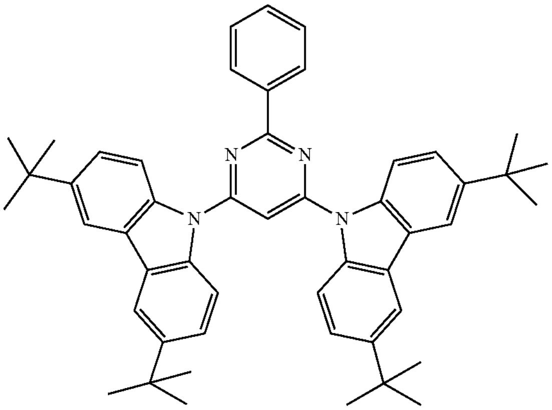
[Formula 34]
2-48
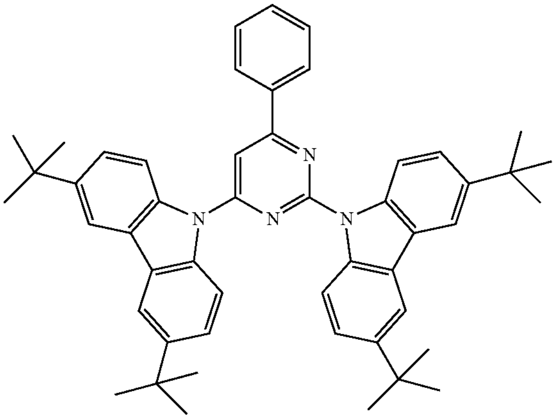
2-49
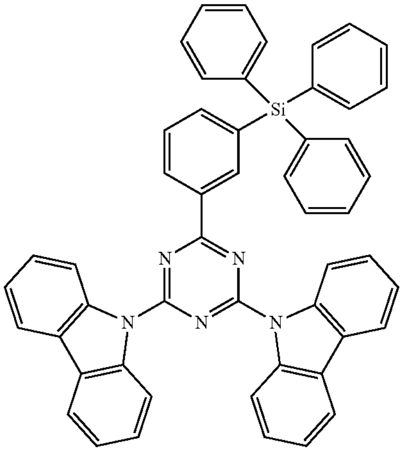

-continued 2-50

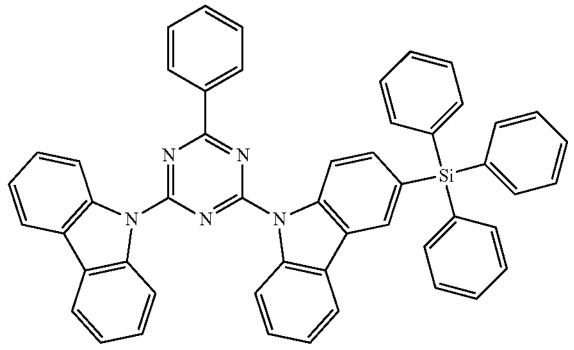

A preferred mode of the organic emission material used in the organic EL device of the present invention is a boron-containing polycyclic aromatic compound represented by the following general formula (3) or (4), and a boron-containing polycyclic aromatic compound represented by the general formula (4) is more preferred.

The boron-containing polycyclic aromatic compound represented by the general formula (3) will be described.

$X^3$ represents O, S, or N-$Ar^3$, and at least one $X^3$ represents N-$Ar^3$. $X^3$ preferably represents O or N-$Ar^3$, and more preferably N-$Ar^3$.

$Ar^3$ represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof.

Preferably, $Ar^3$ represents a substituted or unsubstituted aromatic hydrocarbon group having 6 to 12 carbon atoms, a substituted or unsubstituted aromatic heterocyclic group having 3 to 12 carbon atoms, or a substituted or unsubstituted linked aromatic group formed by linking 2 to 6 aromatic rings thereof.

More preferably, $Ar^3$ represents a substituted or unsubstituted aromatic hydrocarbon group having 6 to 10 carbon atoms, a substituted or unsubstituted aromatic heterocyclic group having 3 to 10 carbon atoms, or a substituted or unsubstituted linked aromatic group formed by linking 2 to 4 aromatic rings thereof.

Specific examples of the unsubstituted $Ar^3$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracenepyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 8 of these compounds.

Preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 6 of these compounds.

More preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, and a compound formed by linking 2 to 4 of these compounds.

Each of these aromatic hydrocarbon groups, aromatic heterocyclic groups, and linked aromatic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino. Preferred examples thereof include cyano, methyl, ethyl, propyl, butyl, pentyl, hexyl, heptyl, octyl, diphenylamino, naphthylphenylamino, and dinaphthylamino.

$R^3$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms. Preferably, $R^3$ is a diarylamino group having 12 to 36 carbon atoms, a substituted or unsubstituted aromatic hydrocarbon group having 6 to 12 carbon atoms, or a substituted or unsubstituted aromatic heterocyclic ring having 3 to 15 carbon atoms. More preferably, $R^3$ is a diarylamino group having 12 to 24 carbon atoms, a substituted or unsubstituted aromatic hydrocarbon group having 6 to 10 carbon atoms, or a substituted or unsubstituted aromatic heterocyclic group having 3 to 12 carbon atoms. i and j represent an integer of 0 to 4, and k represents an integer of 0 to 3.

When $R^3$ represents a diarylamino group having 12 to 44 carbon atoms or an aliphatic hydrocarbon group having 1 to 10 carbon atoms, specific examples of $R^3$ include diphenylamino, dibiphenylamino, phenylbiphenylamino, naphthylphenylamino, dinaphthylamino, dianthranilamino, diphenanthrenylamino, dipyrenylamino, (9-phenylcarbazolyl)phenylamino, dibenzofuranylphenyl, methyl, ethyl, propyl, butyl, pentyl, hexyl, heptyl, octyl, and nonyl. Preferred examples thereof include diphenylamino, dibiphenylamino, phenylbiphenylamino, naphthylphenylamino, dinaphthylamino, dianthranilamino, diphenanthrenylamino, and dipyrenylamino. More preferred examples thereof include diphenylamino, dibiphenylamino, phenylbiphenylamino, naphthylphenylamino, and dinaphthylamino.

When $R^3$ represents an unsubstituted aromatic hydrocarbon group having 6 to 18 carbon atoms or an unsubstituted aromatic heterocyclic group having 3 to 17 carbon atoms, specific examples of $R^3$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

Preferable examples thereof include a group produced by removing one hydrogen atom from benzene, naphthalene, acenaphthene, acenaphthylene, azulene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

More preferred examples thereof include a group produced by removing one hydrogen atom from benzene or naphthalene.

Each of these aromatic hydrocarbon groups and aromatic heterocyclic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino. Preferred examples thereof include cyano, methyl, ethyl, propyl, butyl, pentyl, hexyl, heptyl, octyl, diphenylamino, naphthylphenylamino, and dinaphthylamino.

Specific examples of the compounds represented by the general formula (3) are shown below, but the compounds are not limited to these exemplified compounds.

[Formula 35]

3-1

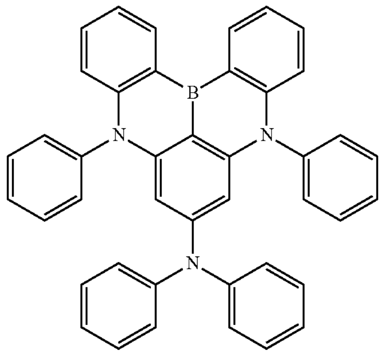

3-2

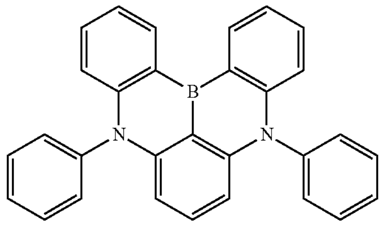

3-3

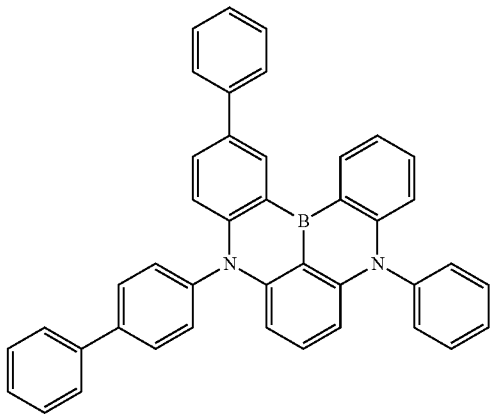

3-4

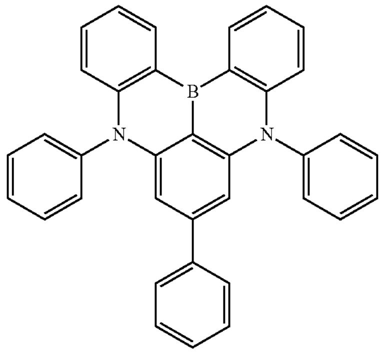

-continued
3-5
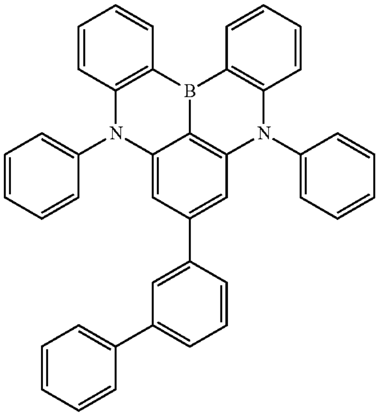
3-6
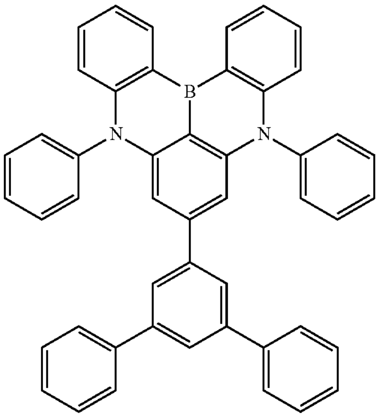
[Formula 36]
3-7
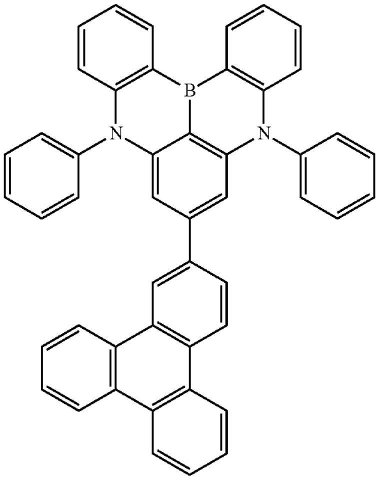
-continued
3-8
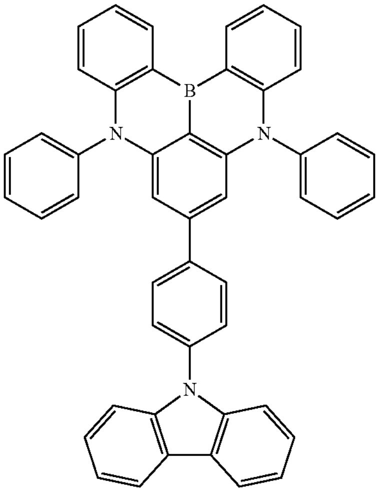
3-9
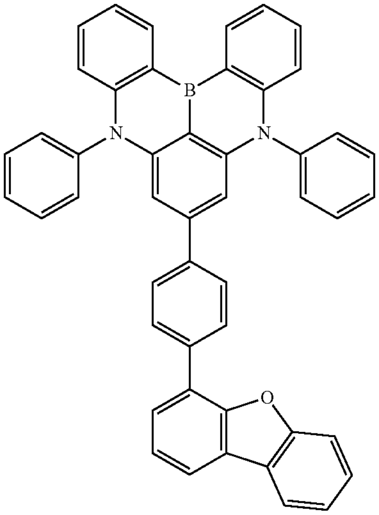
3-10
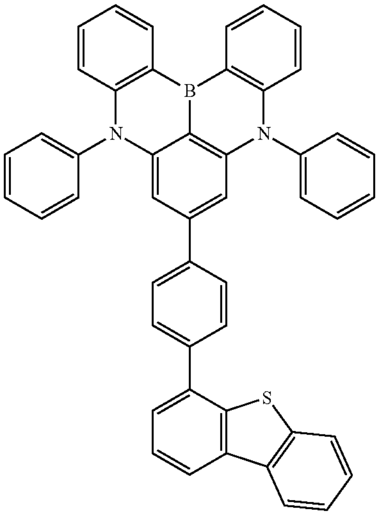

-continued
3-11
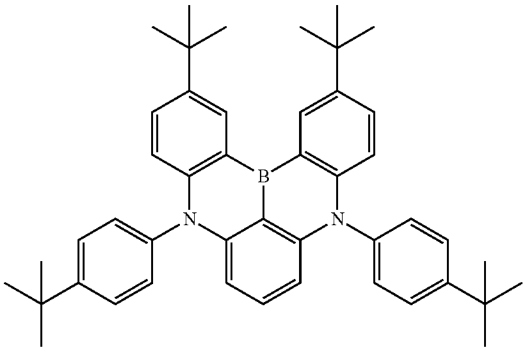
3-12
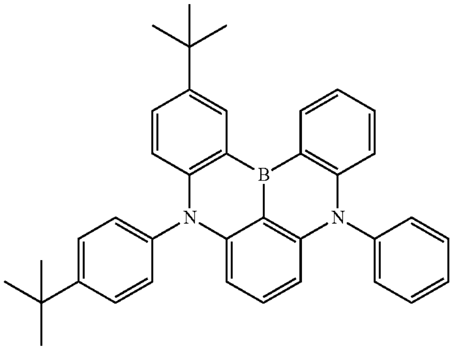
3-13
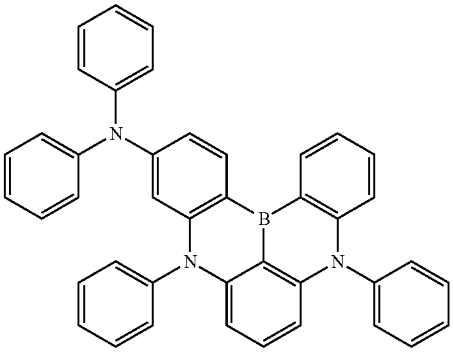
3-14
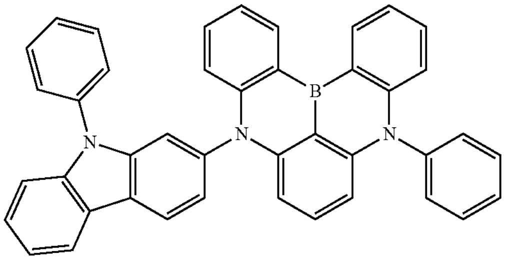
-continued
[Formula 37]
3-15
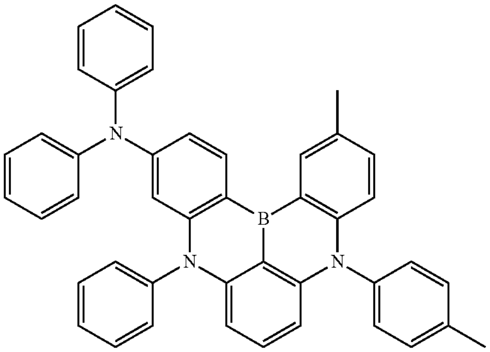
3-16
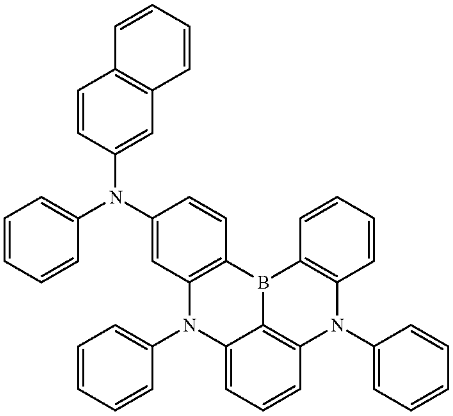
3-17
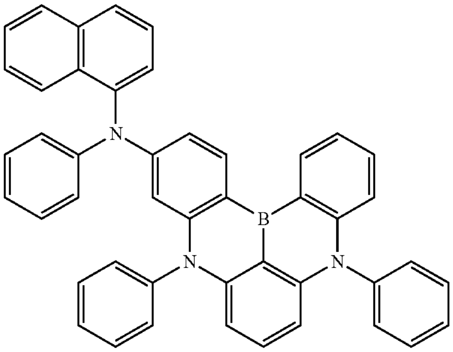
3-18
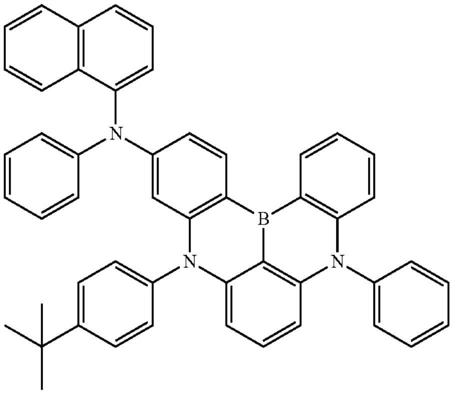

-continued
3-19
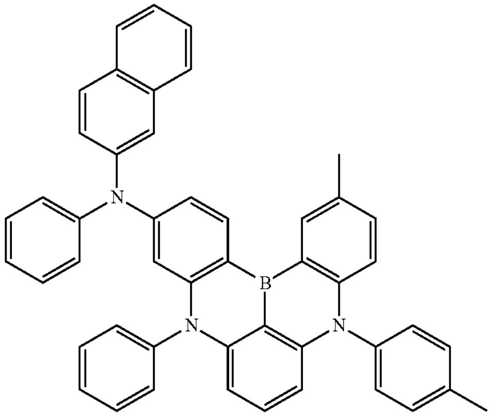
3-20
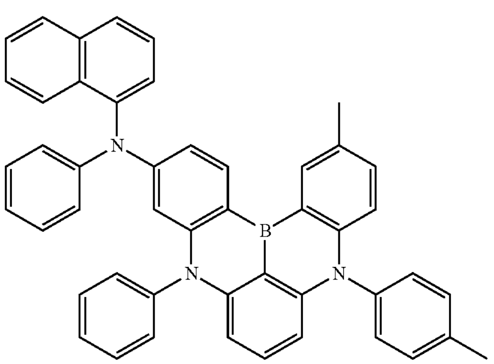
[Formula 38]
3-21
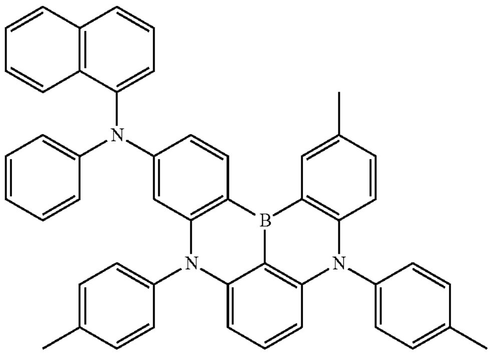
-continued
3-22
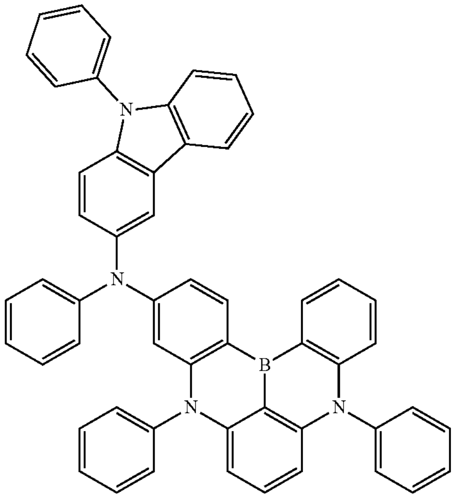
3-23
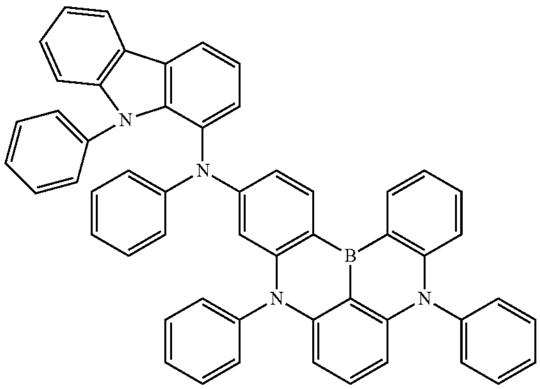
3-24
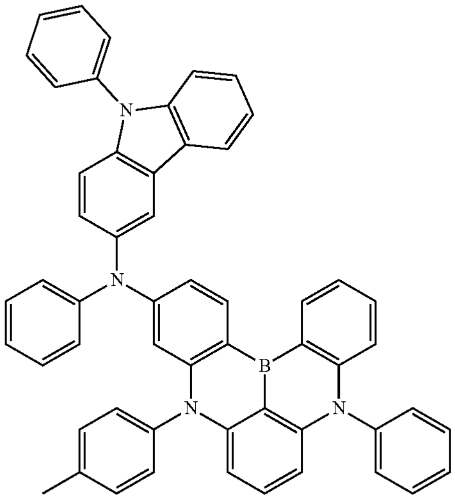

-continued
3-25
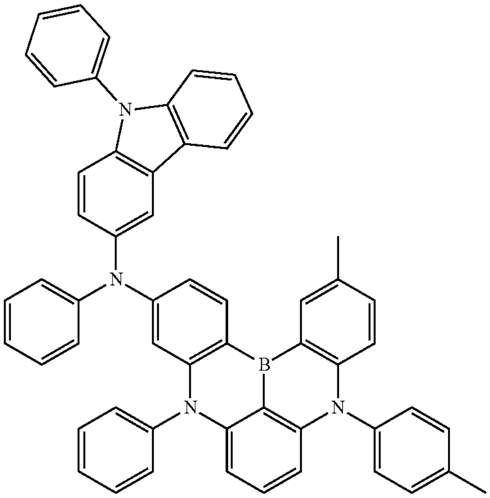
3-26
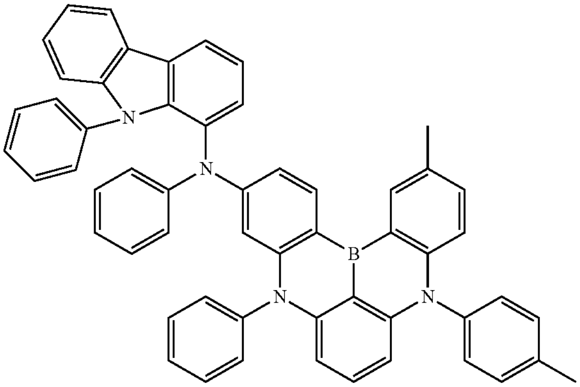
[Formula 39]
3-27
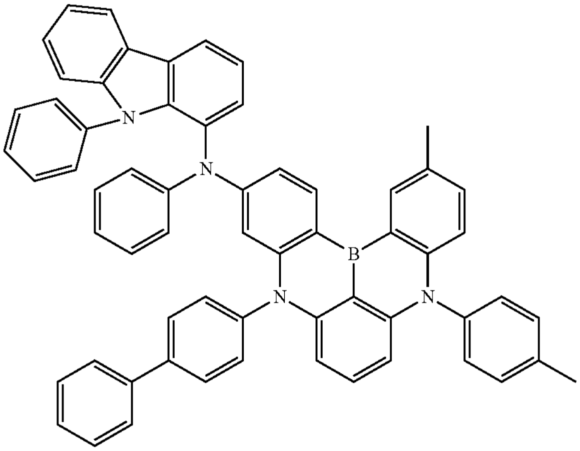
-continued
3-28
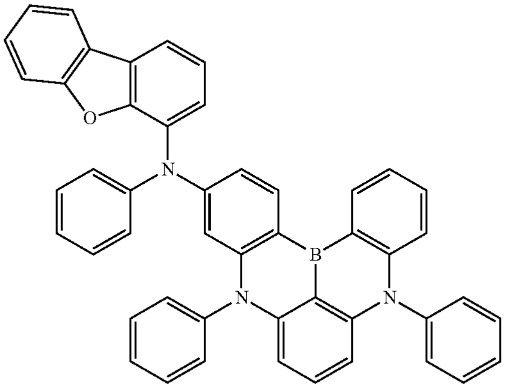
3-29
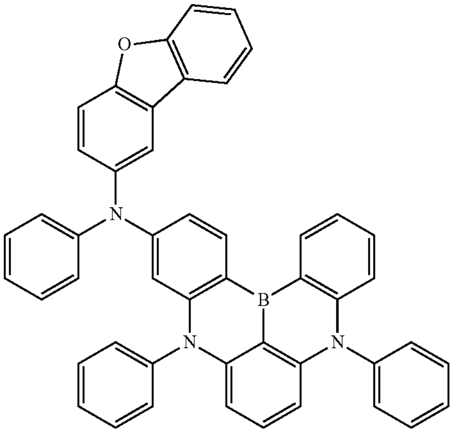
3-30
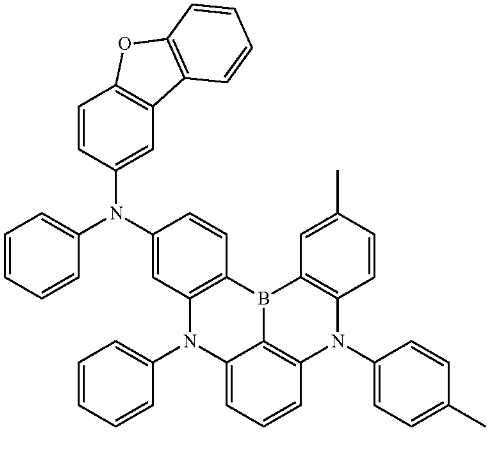

-continued
3-31
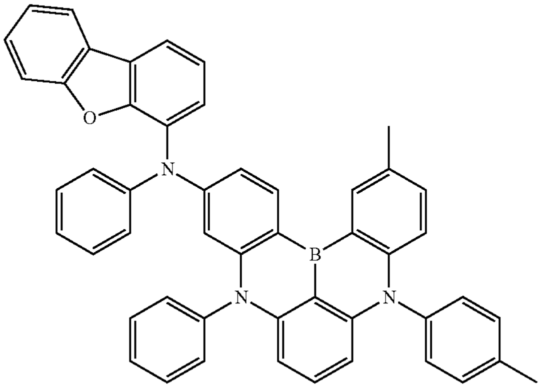
3-32
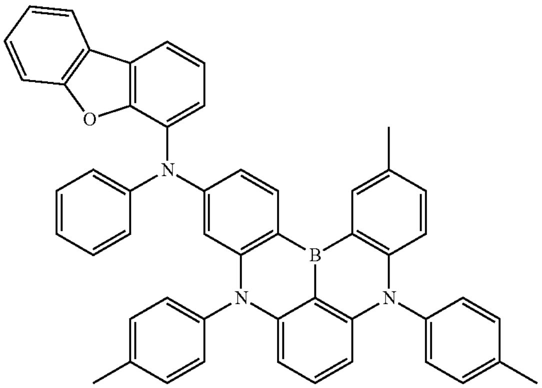
[Formula 40]
3-33
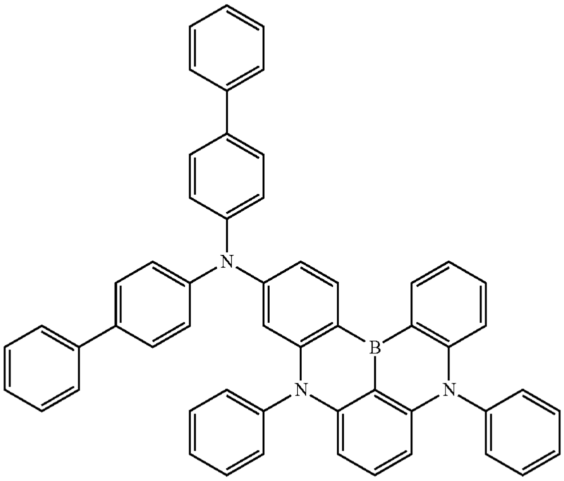
-continued
3-34
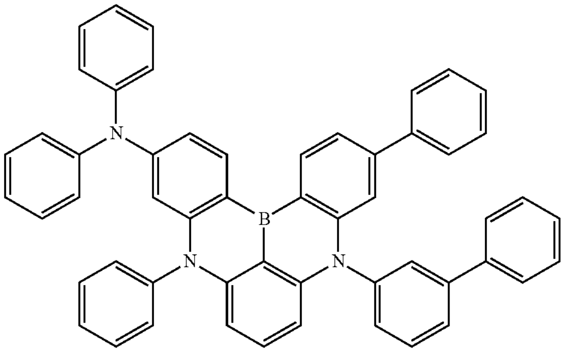
3-35
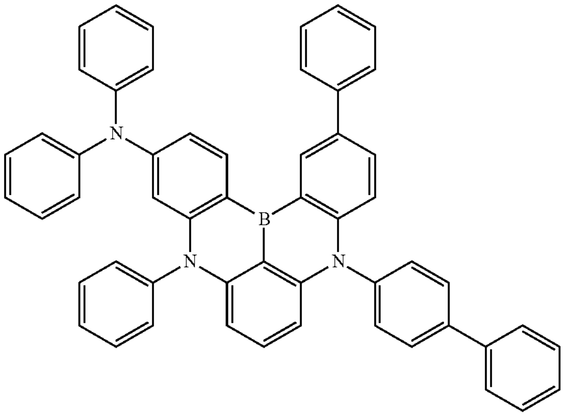
[Formula 41]
3-36
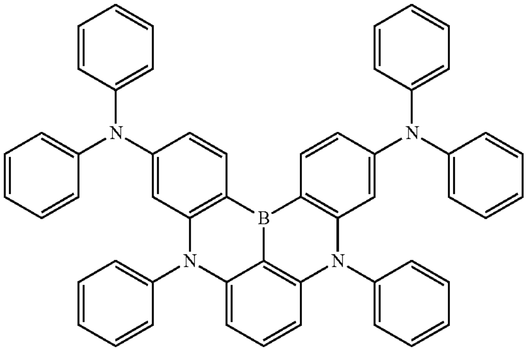

-continued
3-37
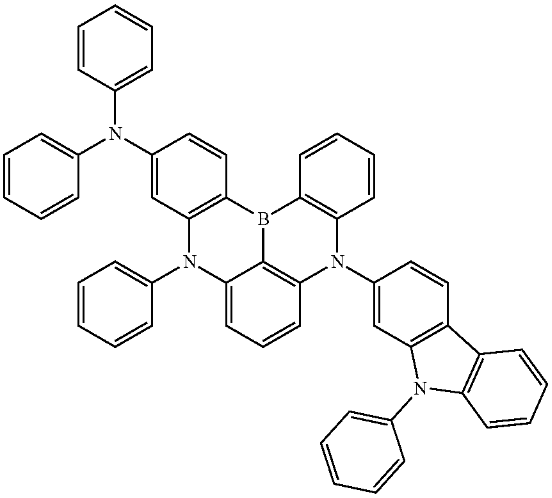
3-38
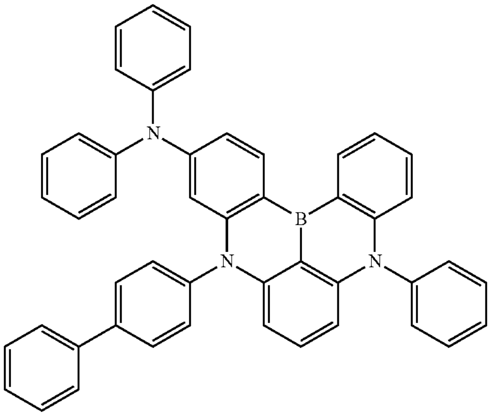
3-39
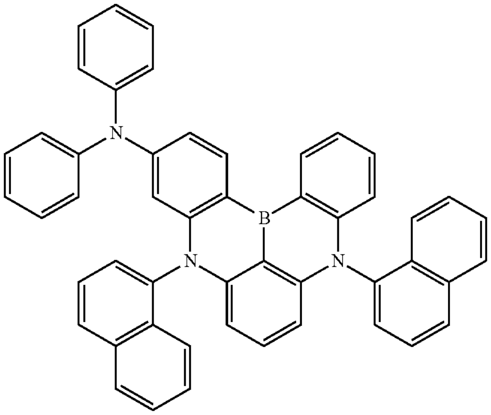
-continued
3-40
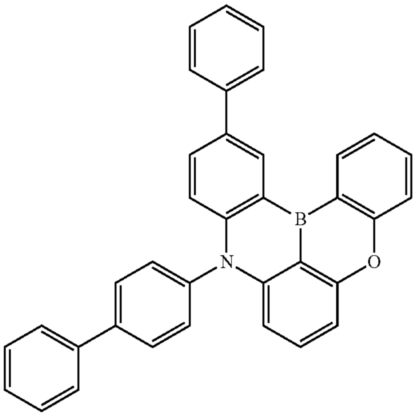
3-41
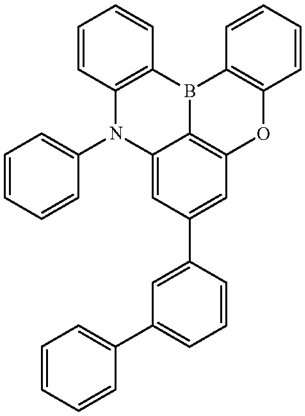
3-42
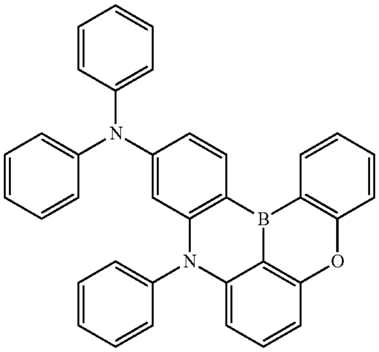
3-43
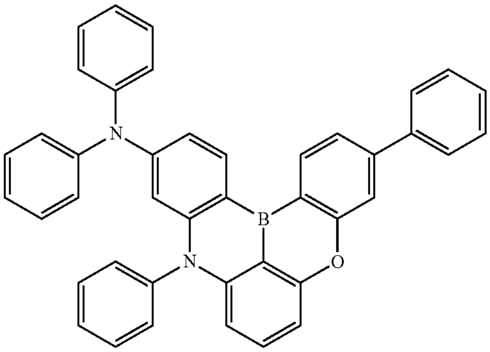

-continued

[Formula 42]

3-44

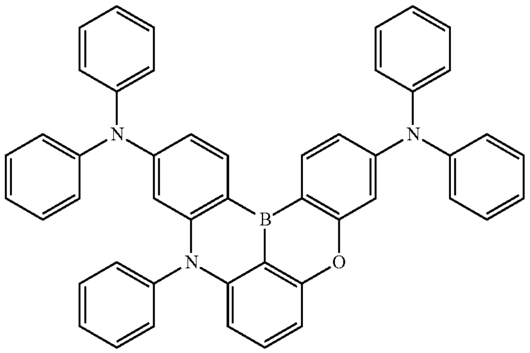

3-45

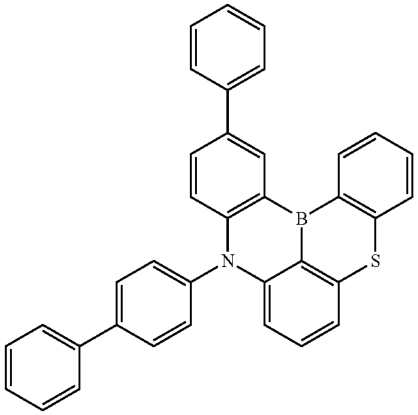

3-46

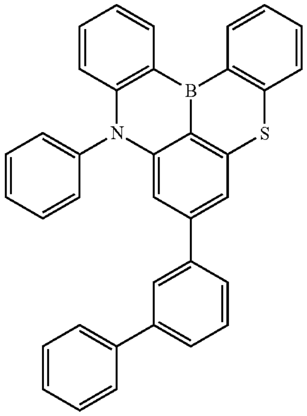

3-47

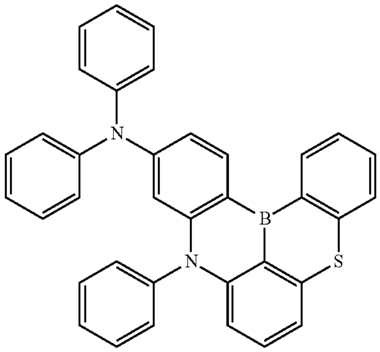

-continued 3-48

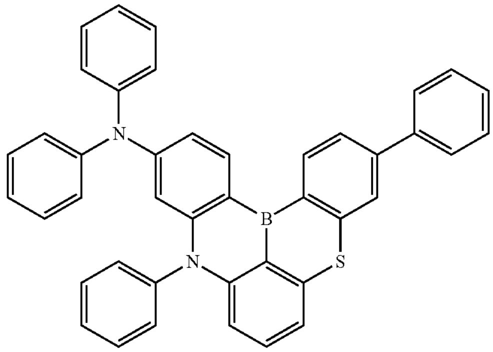

3-49

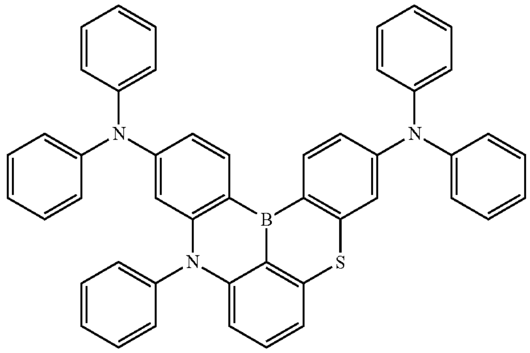

The boron-containing polycyclic aromatic compound represented by the general formula (4) will be described.

$X^4$ represents O, S, or N-$Ar^4$, and at least one $X^4$ represents N-$Ar^4$. $X^4$ preferably represents O or N-$Ar^3$, and more preferably N-$Ar^3$.

$Ar^4$ represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof.

Preferably, $Ar^4$ represents a substituted or unsubstituted aromatic hydrocarbon group having 6 to 12 carbon atoms, a substituted or unsubstituted aromatic heterocyclic group having 3 to 12 carbon atoms, or a substituted or unsubstituted linked aromatic group formed by linking 2 to 6 aromatic rings thereof.

More preferably, $Ar^4$ represents a substituted or unsubstituted aromatic hydrocarbon group having 6 to 10 carbon atoms, a substituted or unsubstituted aromatic heterocyclic group having 3 to 10 carbon atoms, or a substituted or unsubstituted linked aromatic group formed by linking 2 to 4 aromatic rings thereof.

Specific examples of the unsubstituted $Ar^4$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracenepyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 8 of these compounds.

Preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, carbazole, and a compound formed by linking 2 to 6 of these compounds.

More preferred examples thereof include a group produced by removing one hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, and a compound formed by linking 2 to 4 of these compounds.

Each of these aromatic hydrocarbon groups, aromatic heterocyclic groups, and linked aromatic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino.

Preferred examples thereof include cyano, methyl, ethyl, propyl, butyl, pentyl, hexyl, heptyl, octyl, diphenylamino, naphthylphenylamino, and dinaphthylamino.

$R^4$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms.

Preferably, $R^4$ is a diarylamino group having 12 to 36 carbon atoms, a substituted or unsubstituted aromatic hydrocarbon group having 6 to 12 carbon atoms, or a substituted or unsubstituted aromatic heterocyclic ring having 3 to 15 carbon atoms.

More preferably, $R^4$ is a diarylamino group having 12 to 24 carbon atoms, a substituted or unsubstituted aromatic hydrocarbon group having 6 to 10 carbon atoms, or a substituted or unsubstituted aromatic heterocyclic group having 3 to 12 carbon atoms. m and n represent an integer of 0 to 4, o and p represent an integer of 0 to 3, and q represents an integer of 0 to 2.

When $R^4$ represents a diarylamino group having 12 to 44 carbon atoms or an aliphatic hydrocarbon group having 1 to 10 carbon atoms, specific examples of $R^4$ include diphenylamino, dibiphenylamino, phenylbiphenylamino, naphthylphenylamino, dinaphthylamino, dianthranilamino, diphenanthrenylamino, dipyrenylamino, methyl, ethyl, propyl, butyl, pentyl, hexyl, heptyl, octyl, and nonyl.

Preferred examples of $R^4$ include diphenylamino, dibiphenylamino, phenylbiphenylamino, naphthylphenylamino, dinaphthylamino, dianthranilamino, diphenanthrenylamino, and dipyrenylamino.

More preferred examples of $R^4$ include diphenylamino, dibiphenylamino, phenylbiphenylamino, naphthylphenylamino, and dinaphthylamino.

When $R^4$ represents an unsubstituted aromatic hydrocarbon group having 6 to 18 carbon atoms or an unsubstituted aromatic heterocyclic group having 3 to 17 carbon atoms, specific examples of $R^4$ include a group produced by removing one hydrogen atom from benzene, naphthalene, acenaphthene, acenaphthylene, azulene, anthracene, chrysene, pyrene, phenanthrene, triphenylene, fluorene, benzo[a]anthracene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

Preferred examples thereof include a group produced by removing one hydrogen atom from benzene, naphthalene, acenaphthene, acenaphthylene, azulene, pyridine, pyrimidine, triazine, thiophene, isothiazole, thiazole, pyridazine, pyrrole, pyrazole, imidazole, triazole, thiadiazole, pyrazine, furan, isoxazole, quinoline, isoquinoline, quinoxaline, quinazoline, thiadiazole, phthalazine, tetrazole, indole, benzofuran, benzothiophene, benzoxazole, benzothiazole, indazole, benzimidazole, benzotriazole, benzisothiazole, benzothiadiazole, purine, pyranone, coumarin, isocoumarin, chromone, dibenzofuran, dibenzothiophene, dibenzoselenophene, and carbazole.

More preferred examples thereof include a group produced by removing one hydrogen atom from benzene or naphthalene.

Each of these aromatic hydrocarbon groups and aromatic heterocyclic groups may have a substituent. When these groups have a substituent, the substituent is a cyano group, an aliphatic hydrocarbon group having 1 to 10 carbon atoms, or a diarylamino group having 12 to 44 carbon atoms. The number of substituents is 0 to 5, and preferably 0 to 2. When each of the aromatic hydrocarbon groups and aromatic heterocyclic groups has a substituent, the number of carbon atoms of the substituent is not included in the calculation of the number of carbon atoms. However, it is preferred that the total number of carbon atoms including the number of carbon atoms of the substituent satisfy the above range.

Specific examples of the above substituent include cyano, methyl, ethyl, propyl, butyl, pentyl, hexyl, heptyl, octyl, nonyl, decyl, diphenylamino, naphthylphenylamino, dinaphthylamino, dianthranilamino, diphenanthrenylamino, and dipyrenylamino.

Preferred examples thereof include cyano, methyl, ethyl, propyl, butyl, pentyl, hexyl, heptyl, octyl, diphenylamino, naphthylphenylamino, and dinaphthylamino.

Specific examples of the compounds represented by the general formula (4) are shown below, but the compounds are not limited to these exemplified compounds.
[Formula 43]
4-1
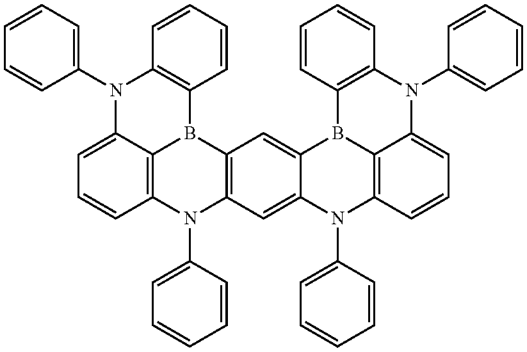
4-2
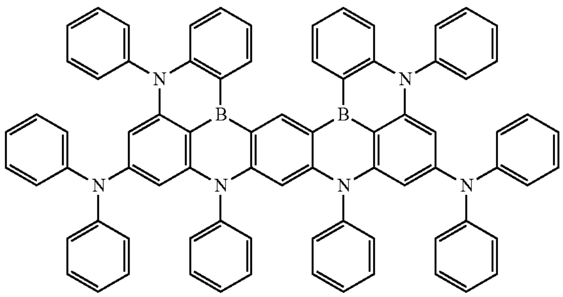
4-3
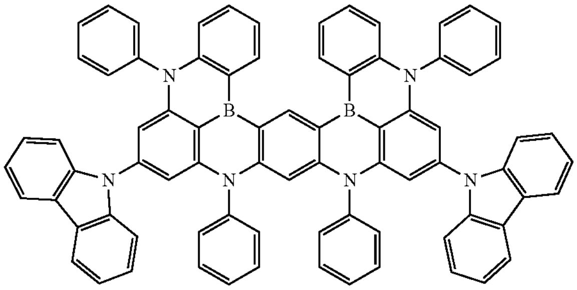
4-4
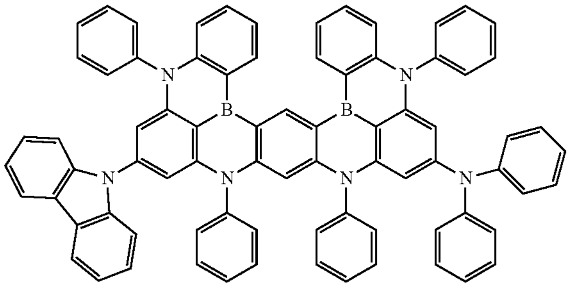
-continued
[Formula 44]
4-5
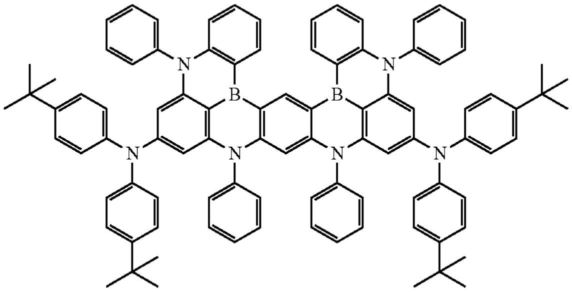
4-6
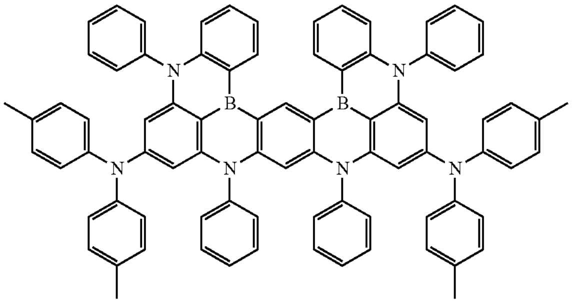
4-7
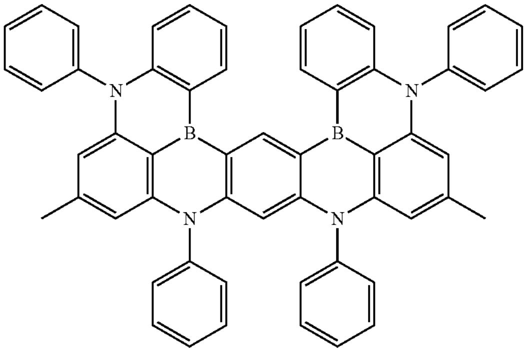
4-8
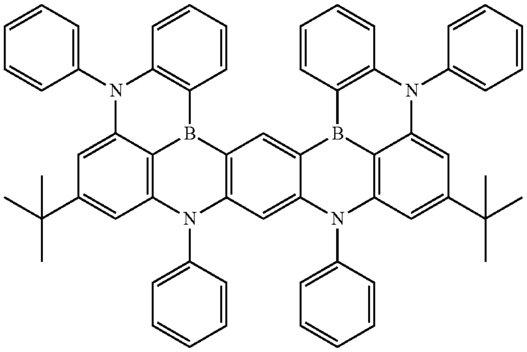

-continued
4-9
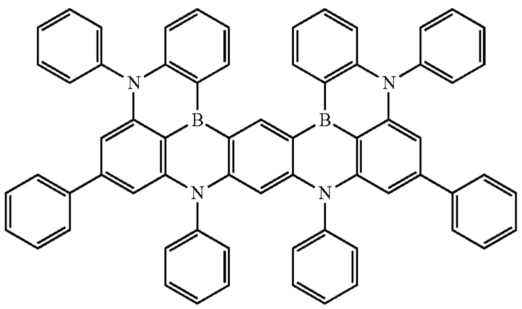
[Formula 45]
4-10
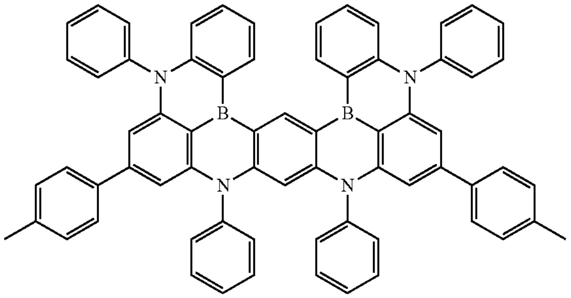
4-11
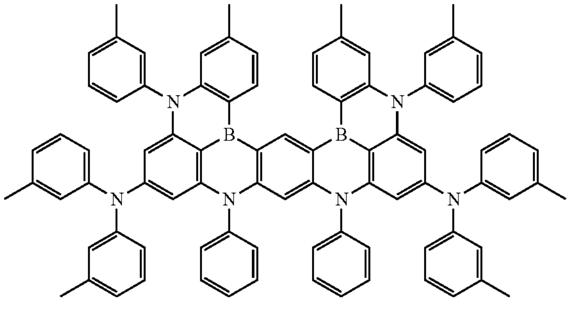
4-12
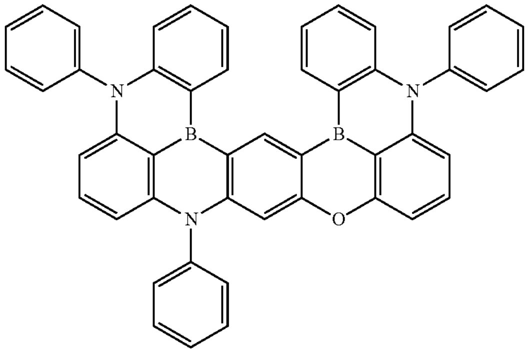
-continued
4-13
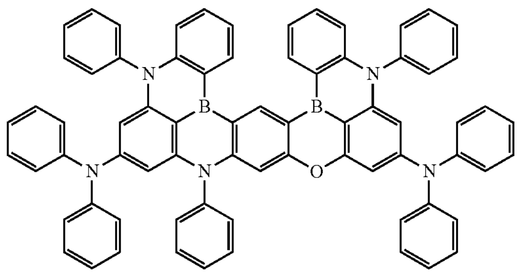
[Formula 46]
4-14
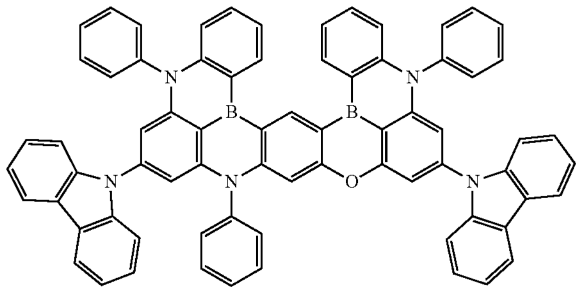
4-15
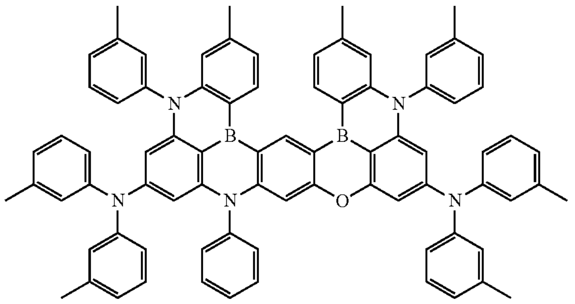
4-16
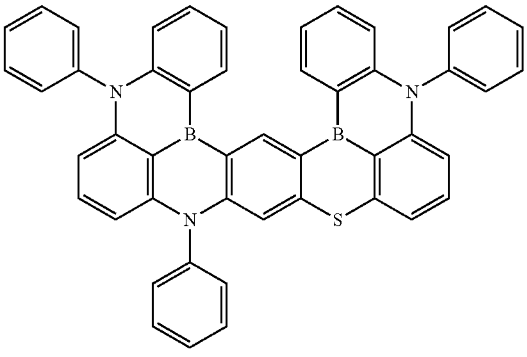
4-17
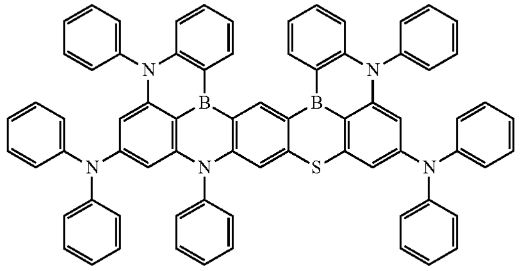

-continued

[Formula 47]

4-18

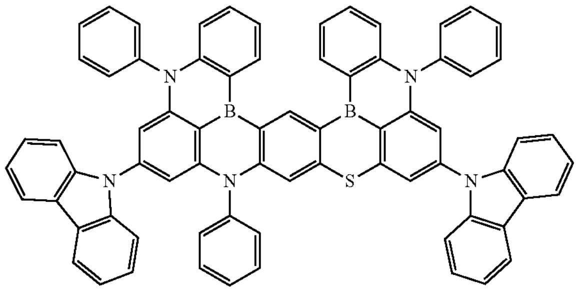

4-19

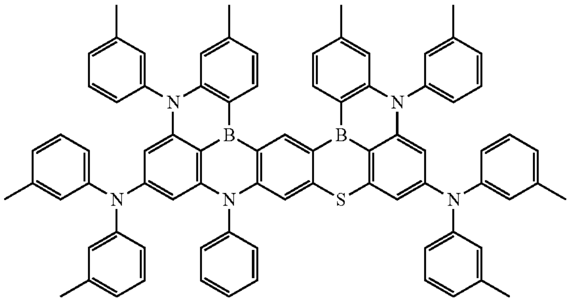

4-20

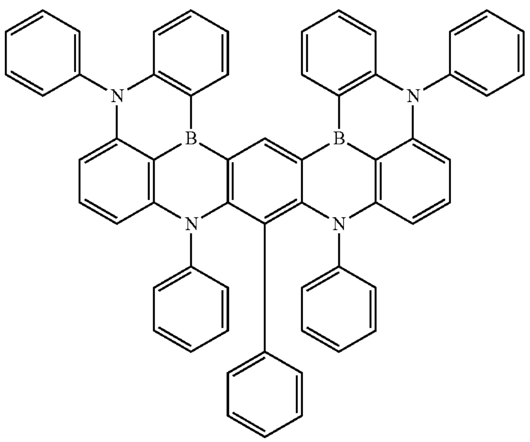

-continued 4-21

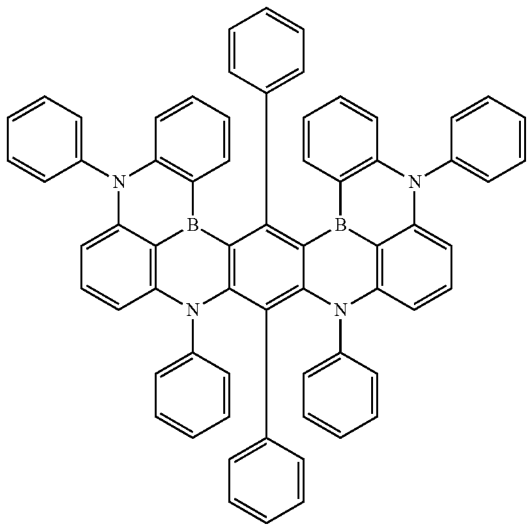

An excellent organic EL device can be provided by using a material selected from the compounds represented by the general formula (3) or (4) as the light emitting dopant, a material selected from the compounds represented by the general formula (1) as the first host, and a material selected from the compounds represented by the general formula (2) as the second host.

Next, the structure of the organic EL device of the present invention will be described with reference to the drawing, but the structure of the organic EL device of the present invention is not limited thereto.

FIG. 1 shows a cross-sectional view of a structure example of a typical organic EL device used in the present invention. Reference numeral 1 denotes a substrate, reference numeral 2 denotes an anode, reference numeral 3 denotes a hole injection layer, reference numeral 4 denotes a hole transport layer, reference numeral 5 denotes a light emitting layer, reference numeral 6 denotes an electron transport layer, and reference numeral 7 denotes a cathode. The organic EL device of the present invention may have an exciton blocking layer adjacent to the light emitting layer, or may have an electron blocking layer between the light emitting layer and the hole injection layer. The exciton blocking layer may be inserted on either the anode side or the cathode side of the light emitting layer or may be inserted on both sides at the same time. The organic EL device of the present invention has the anode, the light emitting layer, and the cathode as essential layers, but preferably has a hole injection/transport layer and an electron injection/transport layer in addition to the essential layers, and further preferably has a hole blocking layer between the light emitting layer and the electron injection/transport layer. The hole injection/transport layer means either or both of the hole injection layer and the hole transport layer, and the electron injection/transport layer means either or both of the electron injection layer and electron transport layer.

It is also possible to have a structure that is the reverse of the structure shown in FIG. 1, that is, the cathode 7, the electron transport layer 6, the light emitting layer 5, the hole transport layer 4, and the anode 2 can be laminated on the substrate 1, in the order presented. Also, in this case, layers can be added or omitted, as necessary.

—Substrate—

The organic EL device of the present invention is preferably supported on a substrate. The substrate is not particularly limited and may be a substrate conventionally used for organic EL devices, and for example, a substrate made of glass, transparent plastic, or quartz can be used.

—Anode—

As the anode material in the organic EL device, a material made of a metal, alloy, or conductive compound having a high work function (4 eV or more), or a mixture thereof is preferably used. Specific examples of such an electrode material include metals such as Au, and conductive transparent materials such as CuI, indium tin oxide (ITO), $SnO_2$, and ZnO. An amorphous material capable of producing a transparent conductive film such as IDIXO ($In_2O_3$—ZnO) may also be used. As the anode, these electrode materials may be formed into a thin film by a method such as vapor deposition or sputtering, and then a pattern of a desired form may be formed by photolithography. Alternatively, when a highly precise pattern is not required (about 100 μm or more), a pattern may be formed through a mask of a desired form at the time of vapor deposition or sputtering of the above electrode materials. Alternatively, when a coatable material such as an organic conductive compound is used, a wet film forming method such as a printing method and a coating method can also be used. When light is extracted from the anode, the transmittance is desirably more than 10%, and the sheet resistance as the anode is preferably several hundred Ω/square or less. The film thickness is selected within a range of usually 10 to 1,000 nm, and preferably 10 to 200 nm, although it depends on the material.

—Cathode—

On the other hand, a material made of a metal (referred to as an electron injection metal), alloy, or conductive compound having a low work function (4 eV or less) or a mixture thereof is used as the cathode material. Specific examples of such an electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among them, in terms of electron injection properties and durability against oxidation and the like, a mixture of an electron injection metal with a second metal that has a higher work function value than the electron injection metal and is stable, for example, a magnesium/silver mixture, a magnesium/aluminum mixture, a magnesium/indium mixture, an aluminum/aluminum oxide ($Al_2O_3$) mixture, a lithium/aluminum mixture, or aluminum is suitable. The cathode can be produced by forming a thin film from these cathode materials by a method such as vapor deposition and sputtering. The sheet resistance as the cathode is preferably several hundred Ω/square or less, and the film thickness is selected within a range of usually 10 nm to 5 μm, and preferably 50 to 200 nm. To transmit the light emitted, either one of the anode and the cathode of the organic EL device is favorably transparent or translucent because light emission brightness is improved.

The above metal is formed to have a film thickness of 1 to 20 nm on the cathode, and then a conductive transparent material mentioned in the description of the anode is formed on the metal, so that a transparent or translucent cathode can be produced. By applying this process, an device in which both anode and cathode have transmittance can be produced.

—Light Emitting Layer—

The light emitting layer is a layer that emits light after holes and electrons respectively injected from the anode and the cathode are recombined to form excitons, and the light emitting layer includes the light emitting dopant and the hosts.

For the light emitting dopant and the hosts, 99.9 to 90 wt % of the hosts and 0.1 to 10 wt % of the light emitting dopant can be used, for example. Preferably, the amount of the light emitting dopant is 1 to 5 wt % and the amount of the hosts is 99 to 95 wt %. More preferably, the amount of the light emitting dopant is 1 to 3 wt % and the amount of the hosts is 99 to 97 wt %.

As the hosts in the light emitting layer, the first host represented by the general formula (1) and the second host represented by the general formula (2) are used. For the first host and the second host, for example, the first host can be used in an amount of 10 to 90 wt % and the second host can be used in an amount of 90 to 10 wt %. Preferably, the amount of the first host is 30 to 70 wt % and the amount of the second host is 70 to 30 wt %. More preferably, the amount of the first host is 40 to 60 wt % and the amount of the second host is 60 to 40 wt %.

Further, one or more known hosts may be used in combination, but the amount used thereof may be 50 wt % or less, and preferably 25 wt % or less based on the total amount of the host material.

A usable known host is a compound having the ability to transport hole, the ability to transport electron, and a high glass transition temperature, and preferably has a higher T1 than the T1 of the light emitting dopant.

Such other hosts are known in a large number of patent literatures and the like, and hence may be selected from them. Specific examples of the host include, but are not particularly limited to, various metal complexes typified by metal complexes of indole derivatives, carbazole derivatives, indolocarbazole derivatives, triazole derivatives, oxazole derivatives, oxadiazole derivatives, imidazole derivatives, phenylenediamine derivatives, arylamine derivatives, styrylanthracene derivatives, fluorenone derivatives, stilbene derivatives, triphenylene derivatives, carborane derivatives, porphyrin derivatives, phthalocyanine derivatives, and 8-quinolinol derivatives, and metal phthalocyanine, and metal complexes of benzoxazole and benzothiazole derivatives; and polymer compounds such as poly(N-vinyl carbazole) derivatives, aniline-based copolymers, thiophene oligomers, polythiophene derivatives, polyphenylene derivatives, polyphenylene vinylene derivatives, and polyfluorene derivatives.

When a plurality of hosts is used, each host is deposited from different deposition sources, or a plurality of hosts is premixed before vapor deposition to form a premix, whereby a plurality of hosts can be simultaneously deposited from one deposition source.

As the method of premixing, a method by which hosts can be mixed as uniformly as possible is desirable, and examples thereof include, but are not limited to, milling, a method of heating and melting hosts under reduced pressure or under an inert gas atmosphere such as nitrogen, and sublimation.

As the light emitting dopant in the light emitting layer, an organic emission material having a difference between excited singlet energy (S1) and excited triplet energy (T1) (ΔEST) of 0.20 eV or less is used. As the organic emission material, a compound represented by the general formula (3) or (4) is preferred.

Only one organic light emitting dopant may be contained or two or more organic light emitting dopants may be contained in the light emitting layer. The content of the organic light emitting dopant is preferably 0.1 to 50 wt %, and more preferably 1 to 40 wt % based on the host material.

The organic light emitting dopant and the first host or the organic light emitting dopant and the second host may be deposited from different deposition sources, or may be premixed before vapor deposition to form a premix, whereby the light emitting dopant and the first host or the light emitting dopant and the second host can be simultaneously deposited from one deposition source.

—Injection Layer—

The injection layer refers to a layer provided between the electrode and the organic layer to reduce the driving voltage and improve the light emission brightness, and includes the hole injection layer and the electron injection layer. The injection layer may be present between the anode and the light emitting layer or the hole transport layer, as well as between the cathode and the light emitting layer or the electron transport layer. The injection layer may be provided as necessary.

—Hole Blocking Layer—

The hole blocking layer has the function of the electron transport layer in a broad sense, is made of a hole blocking material having a very small ability to transport holes while having the function of transporting electrons, and can improve the recombination probability between the electrons and the holes in the light emitting layer by blocking the holes while transporting the electrons. For the hole blocking layer, a known hole blocking material can be used. To exhibit the characteristics of the light emitting dopant, the material used as the second host can also be used as the material for the hole blocking layer. A plurality of hole blocking materials may be used in combination.

—Electron Blocking Layer—

The electron blocking layer has the function of the hole transport layer in a broad sense, and can improve the recombination probability between the electrons and the holes in the light emitting layer by blocking the electrons while transporting the holes. As the material for the electron blocking layer, a known material for the electron blocking layer can be used. To exhibit the characteristics of the light emitting dopant, the material used as the first host can also be used as the material for the electron blocking layer.

The film thickness of the electron blocking layer is preferably 3 to 100 nm, and more preferably 5 to 30 nm.

—Exciton Blocking Layer—

The exciton blocking layer is a layer to block the diffusion of the excitons generated by recombination of the holes and the electrons in the light emitting layer into a charge transport layer, and insertion of this layer makes it possible to efficiently keep the excitons in the light emitting layer, so that the emission efficiency of the device can be improved. The exciton blocking layer can be inserted between two light emitting layers adjacent to each other in the device in which two or more light emitting layers are adjacent to each other.

As the material for the exciton blocking layer, a known material for the exciton blocking layer can be used.

The layer adjacent to the light emitting layer includes the hole blocking layer, the electron blocking layer, and the exciton blocking layer, and when these layers are not provided, the adjacent layer is the hole transport layer, the electron transport layer, and the like.

—Hole Transport Layer—

The hole transport layer is made of a hole transport material having the function of transporting holes, and the hole transport layer may be provided as a single layer or a plurality of layers.

The hole transport material has any of hole injection properties, hole transport properties, or electron barrier properties, and may be either an organic material or an inorganic material. As the hole transport layer, any of conventionally known compounds may be selected and used. Examples of such a hole transport material include porphyrin derivatives, arylamine derivatives, triazole derivatives, oxadiazole derivatives, imidazole derivatives, polyarylalkane derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and conductive polymer oligomers, particularly, thiophene oligomers. Porphyrin derivatives, arylamine derivatives, and styrylamine derivatives are preferably used, and arylamine compounds are more preferably used.

—Electron Transport Layer—

The electron transport layer is made of a material having the function of transporting electrons, and the electron transport layer may be provided as a single layer or a plurality of layers.

The electron transport material (may also serve as the hole blocking material) has the function of transmitting electrons injected from the cathode to the light emitting layer. As the electron transport layer, any of conventionally known compounds may be selected and used, and examples thereof include polycyclic aromatic derivatives such as naphthalene, anthracene, and phenanthroline, tris(8-quinolinolato)aluminum (III) derivatives, phosphine oxide derivatives, nitro-substituted fluorene derivatives, diphenylquinone derivatives, thiopyran dioxide derivatives, carbodiimides, fluorenylidene methane derivatives, anthraquinodimethane and anthrone derivatives, bipyridine derivatives, quinoline derivatives, oxadiazole derivatives, benzimidazole derivatives, benzothiazole derivatives, and indolocarbazole derivatives. Further, polymer materials in which these materials are introduced in the polymer chain or these materials constitute the main chain of the polymer can also be used.

When the organic EL device of the present invention is produced, the film formation method of each layer is not particularly limited, and the layers may be produced by either a dry process or a wet process.

EXAMPLES

Hereinafter, the present invention will be described in further detail with reference to Examples, but the present invention is not limited to these Examples.

The compounds used in Examples and Comparative Examples are shown below.

[Formula 48]

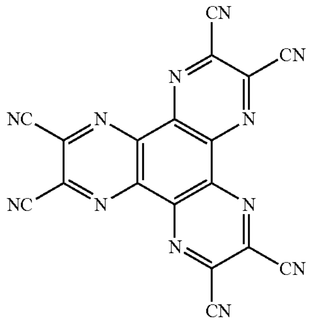

HAT-CN

-continued

HT-1

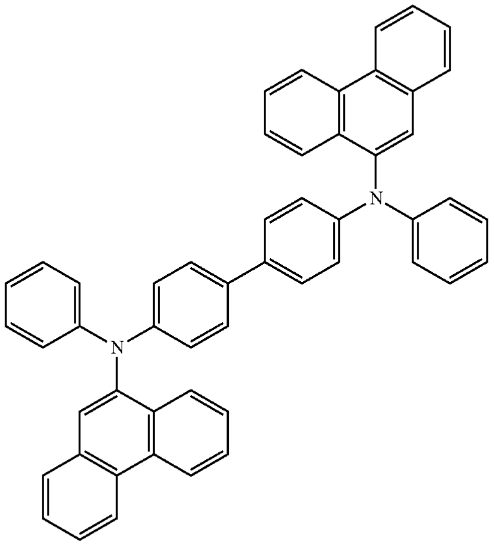

ET-1

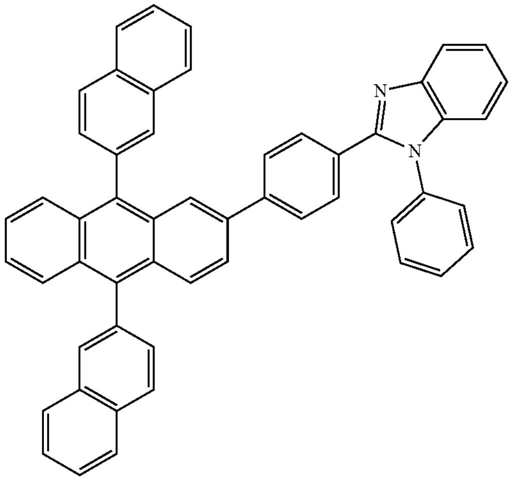

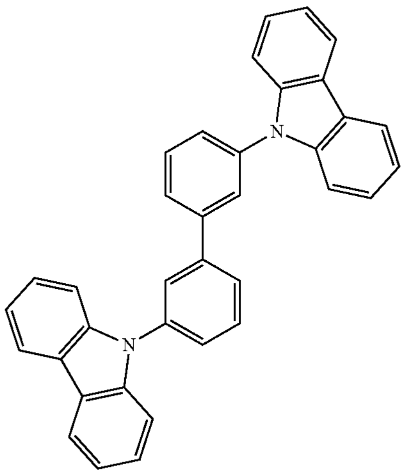

mCBP

-continued

BH1

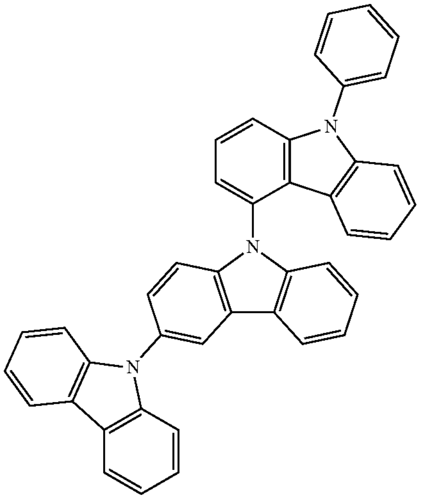

S1 and T1 of the compounds (3-2) and (4-2) were measured.

S1 and T1 were measured as follows.

BH1 as a host and the compound (3-2) or (4-2) as a light emitting dopant were co-deposited on a quartz substrate from different deposition sources by a vacuum deposition method under conditions of a degree of vacuum of $10^{-4}$ Pa or less to form a deposition film having a thickness of 100 nm. At this time, they were co-deposited under deposition conditions such that the concentration of the compound (3-2) or (4-2) was 3 wt %. For S1, the emission spectrum of this deposition film was measured, a tangent was drawn to the rise of the emission spectrum on the short-wavelength side, and the wavelength value λedge [nm] of the point of intersection of the tangent and the horizontal axis was substituted into the following equation (i) to calculate S1.

$$S1\ [\text{eV}]=1239.85/\lambda\text{edge} \quad \text{(i)}$$

For T1, the phosphorescence spectrum of the above deposition film was measured, a tangent was drawn to the rise of the phosphorescence spectrum on the short-wavelength side, and the wavelength value λedge [nm] of the point of intersection of the tangent and the horizontal axis was substituted into the following equation (ii) to calculate T1.

$$T1\ [\text{eV}]=1239.85/\lambda\text{edge} \quad \text{(ii)}$$

TABLE 1

| Compound | S1(eV) | T1(eV) | S1 − T1(eV) |
|---|---|---|---|
| 3-2 | 2.79 | 2.61 | 0.18 |
| 4-2 | 2.71 | 2.67 | 0.04 |

Example 1

Each thin film was laminated on the glass substrate on which an anode made of ITO having a film thickness of 70 nm was formed by a vacuum deposition method at a degree of vacuum of $4.0\times10^{-5}$ Pa. First, HAT-CN was formed on ITO to a thickness of 10 nm as a hole injection layer, and then HT-1 was formed to a thickness of 25 nm as a hole transport layer. Then, a compound (1-77) was formed to a thickness of 5 nm as an electron blocking layer. Then, the compound (1-77) as the first host, a compound (2-1) as the second host, and the compound (4-2) as the light emitting dopant were co-deposited from different deposition sources to form a light emitting layer having a thickness of 30 nm. At this time, they were co-deposited under deposition conditions such that the concentration of the compound (4-2) was 2 wt % and the weight ratio of the first host to the second host was 50:50. Then, compound (2-1) was formed to a thickness of 5 nm as a hole blocking layer. Then, ET-1 was formed to a thickness of 40 nm as an electron transport layer. Further, lithium fluoride (LiF) was formed on the electron transport layer to a thickness of 1 nm as an electron injection layer. Finally, aluminum (Al) was formed on the electron injection layer to a thickness of 70 nm as a cathode, whereby an organic EL device was produced.

Examples 2 to 10

Each organic EL device was produced in the same manner as in Example 1, except that the light emitting dopant, the first host, and the second host, as well as the weight ratio of the first host to the second host were changed to the compounds shown in Table 2.

Comparative Example 1

Each thin film was laminated on the glass substrate on which an anode made of ITO having a film thickness of 70 nm was formed, by a vacuum deposition method at a degree of vacuum of $4.0\times10^{-5}$ Pa. First, HAT-CN was formed on ITO to a thickness of 10 nm as a hole injection layer, and then HT-1 was formed to a thickness of 25 nm as a hole transport layer. Then, the compound (1-77) was formed to a thickness of 5 nm as an electron blocking layer. Then, the compound (1-77) as the first host and the compound (4-2) as the light emitting dopant were co-deposited from different deposition sources to form a light emitting layer having a thickness of 30 nm. At this time, they were co-deposited under deposition conditions such that the concentration of the compound (4-2) was 2 wt %. Then, the compound (2-1) was formed to a thickness of 5 nm as a hole blocking layer. Then, ET-1 was formed to a thickness of 40 nm as an electron transport layer. Further, lithium fluoride (LiF) was formed on the electron transport layer to a thickness of 1 nm as an electron injection layer. Finally, aluminum (Al) was formed on the electron injection layer to a thickness of 70 nm as a cathode, whereby an organic EL device was produced.

Comparative Examples 2, 3, 5, 6, and 7

Each organic EL device was produced in the same manner as in Comparative Example 1, except that the light emitting dopant and the first host (no second host) were changed to the compounds shown in Table 2.

Comparative Examples 4 and 8

Each organic EL device was produced in the same manner as in Example 1, except that the light emitting dopant, the first host, and the second host were changed to the compounds shown in Table 2.

TABLE 2

| | Light emitting dopant | First host | Second host |
|---|---|---|---|
| Example 1 | 4-2 | 1-77 (50%) | 2-1 (50%) |
| Example 2 | 4-2 | 1-77 (30%) | 2-1 (70%) |
| Example 3 | 4-2 | 1-77 (70%) | 2-1 (30%) |
| Example 4 | 4-2 | 1-120 (50%) | 2-1 (50%) |
| Example 5 | 4-2 | 1-132 (50%) | 2-1 (50%) |
| Example 6 | 4-2 | 1-89 (50%) | 2-1 (50%) |
| Example 7 | 4-2 | 1-77 (50%) | 2-3 (50%) |
| Example 8 | 4-2 | 1-77 (50%) | 2-15 (50%) |
| Example 9 | 4-2 | 1-77 (50%) | 2-37 (50%) |
| Example 10 | 3-2 | 1-134 (50%) | 2-1 (50%) |
| Comp. Example 1 | 4-2 | 1-77 | — |
| Comp. Example 2 | 4-2 | 2-1 | — |
| Comp. Example 3 | 4-2 | mCBP | — |
| Comp. Example 4 | 4-2 | mCBP (50%) | 2-1 (50%) |
| Comp. Example 5 | 3-2 | 1-134 | |
| Comp. Example 6 | 3-2 | 2-1 | |
| Comp. Example 7 | 3-2 | mCBP | |
| Comp. Example 8 | 3-2 | mCBP (50%) | 2-1 (50%) |

The voltage, maximum emission wavelength of the emission spectrum, external quantum efficiency, and lifetime of each organic EL device produced in Examples and Comparative Examples are shown in Table 3. The voltage, the maximum emission wavelength, and the external quantum efficiency were values at luminance of 500 cd/$m^2$ and were initial characteristics. The time taken for the luminance to reduce to 50% of the initial luminance when the initial luminance was 500 cd/$m^2$ was measured as the lifetime.

TABLE 3

| | Voltage (V) | Maximum emission wavelength (nm) | External quantum efficiency (%) | Lifetime (h) |
|---|---|---|---|---|
| Example 1 | 3.8 | 472 | 24.1 | 211 |
| Example 2 | 3.8 | 472 | 24.6 | 205 |
| Example 3 | 3.8 | 473 | 21.1 | 199 |
| Example 4 | 3.8 | 471 | 24.4 | 132 |
| Example 5 | 3.9 | 472 | 23.6 | 104 |
| Example 6 | 3.8 | 470 | 22.1 | 88 |
| Example 7 | 3.7 | 472 | 23.9 | 240 |
| Example 8 | 3.7 | 473 | 21.9 | 228 |
| Example 9 | 3.8 | 470 | 22.5 | 222 |
| Example 10 | 3.9 | 460 | 14.1 | 61 |
| Comp. Example 1 | 4.5 | 473 | 23.0 | 50 |
| Comp. Example 2 | 3.9 | 471 | 18.9 | 26 |
| Comp. Example 3 | 4.7 | 471 | 13.6 | 18 |
| Comp. Example 4 | 4.1 | 472 | 19.2 | 31 |
| Comp. Example 5 | 4.1 | 459 | 6.7 | 10 |
| Comp. Example 6 | 4.2 | 460 | 8.8 | 18 |
| Comp. Example 7 | 4.8 | 459 | 8.5 | 8 |
| Comp. Example 8 | 4.4 | 461 | 10.2 | 32 |

It is found from Table 3 that the organic EL device that uses the compound represented by the general formula (1) as the first host, the compound represented by the general formula (2) as the second host, and the compound represented by the general formula (3) or (4) as the light emitting dopant exhibits blue light emission from the maximum emission wavelength and has a low voltage, high efficiency, and long lifetime characteristics.

INDUSTRIAL APPLICABILITY

Since the organic EL device of the present invention has a low driving voltage, high emission efficiency, and long lifetime characteristics, the organic EL device of the present invention can be practically suitably utilized for a display device such as a flat panel display and a light source.

REFERENCE SIGNS LIST

1 substrate, 2 the anode, 3 hole injection layer, 4 hole transport layer, 5 light emitting layer, 6 electron transport layer, 7 cathode

The invention claimed is:

1. An organic electroluminescent device comprising one or more light emitting layers between an anode and a cathode opposite to each other, wherein at least one of the light emitting layers contains an organic emission material having a difference between excited singlet energy (S1) and excited triplet energy (T1) (ΔEST) of 0.20 eV or less as a light emitting dopant, a first host selected from the compounds represented by the following general formula (1), and a second host selected from the compounds represented by the following general formula (2); and the organic emission material is a boron-containing polycyclic aromatic compound represented by the following general formula (3) or (4):

(1)

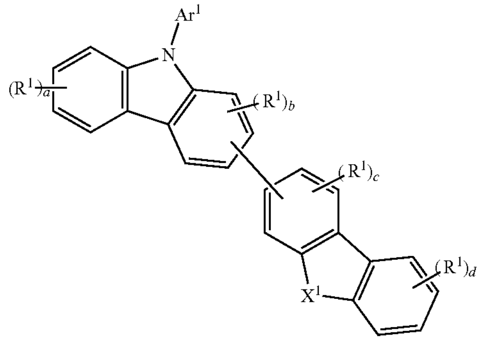

wherein $X^1$ represents O, S, or N-$Ar^1$; $Ar^1$ independently represents a substituted or unsubstituted monocyclic aromatic hydrocarbon group having 6 carbon atoms, a substituted or unsubstituted aromatic heterocyclic group having 3 to 17 carbon atoms, or a substituted or unsubstituted linked aromatic group formed by linking 2 to 3 aromatic rings thereof; $R^1$ independently represents deuterium, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms; a and d represent an integer of 0 to 4; and b and c represent an integer of 0 to 3, (2)

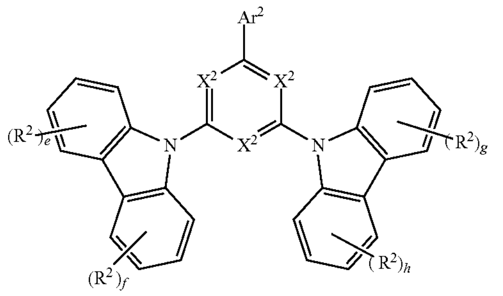

wherein $X^2$ independently represents N or C—H, and at least two $X^2$ represent N; $Ar^2$ represents a substituted or unsubstituted monocyclic aromatic hydrocarbon group having 6 carbon atoms, a substituted or unsubstituted aromatic heterocyclic group having 3 to 17 carbon atoms, or a substituted or unsubstituted linked aromatic group formed by linking 2 to 4 aromatic rings thereof; $R^2$ independently represents deuterium, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms; and e, f, g, and h represent an integer of 0 to 4, (3)

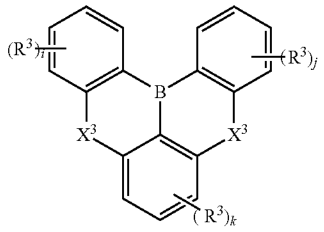

wherein $X^3$ represents N-$Ar^3$, O, or S, and at least one $X^3$ represents N-$Ar^3$; $Ar^3$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof; $R^3$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms; i and j represent an integer of 0 to 4; and k represents an integer of 0 to 3, (4)

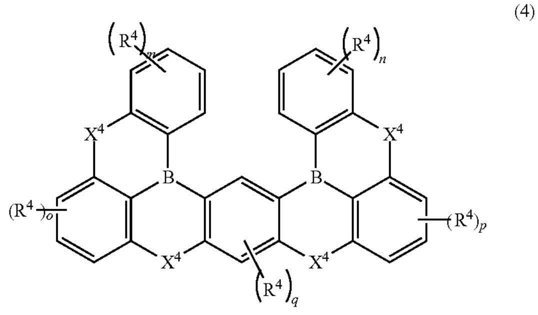

wherein $X^4$ represents N-$Ar^4$, O, or S, and at least one $X^4$ represents N-$Ar^4$; $Ar^4$ independently represents a substituted or unsubstituted aromatic hydrocarbon group having 6 to 18 carbon atoms, a substituted or unsubstituted aromatic heterocyclic group having 3 to 17 carbon atoms, or a substituted or unsubstituted linked aromatic group formed by linking 2 to 8 aromatic rings thereof; $R^4$ independently represents a cyano group, deuterium, a diarylamino group having 12 to 44 carbon atoms, an aliphatic hydrocarbon group having 1 to 10 carbon atoms, a substituted or unsubstituted aromatic hydrocarbon group having 6 to 18 carbon atoms, or a substituted or unsubstituted aromatic heterocyclic group having 3 to 17 carbon atoms; m and n represent an integer of 0 to 4; o and p represent an integer of 0 to 3; and q represents an integer of 0 to 2, and wherein, when the aromatic hydrocarbon group, aromatic heterocyclic group, or linking aromatic group in $Ar^1$, $Ar^2$, $Ar^3$, $Ar^4$, $R^1$, $R^2$, $R^3$, and $R^4$ is substituted, the substituent is an aliphatic hydrocarbon group having 1 to 10 carbon atoms.

2. The organic electroluminescent device according to claim 1, wherein the organic emission material is represented by the general formula (4).

3. The organic electroluminescent device according to claim 1, wherein $X^4$ in the general formula (4) is N-$Ar^4$.

4. The organic electroluminescent device according to claim 1, wherein $X^1$ in the general formula (1) is N-$Ar^1$.

5. The organic electroluminescent device according to claim 1, wherein the compound represented by the general formula (1) is represented by the following general formula (5):

(5)

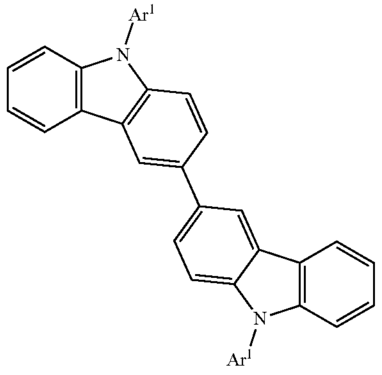

wherein $Ar^1$ has the same meaning as $Ar^1$ in the general formula (1).

6. The organic electroluminescent device according to claim 1, wherein ΔEST of the organic emission material is 0.10 eV or less.

7. The organic electroluminescent device according to claim 1, wherein 99.9 to 90 wt % of the hosts and 0.1 to 10 wt % of the light emitting dopant are contained, and the first host is contained in an amount of 10 to 90 wt % and the second host is contained in an amount of 90 to 10 wt %, based on the hosts.

8. The organic electroluminescent device according to claim 1, wherein $Ar^1$ in the general formula (1) independently represents an unsubstituted monocyclic aromatic hydrocarbon group having 6 carbon atoms, an unsubstituted aromatic heterocyclic group having 3 to 17 carbon atoms, or an unsubstituted linked aromatic group formed by linking 2 to 3 aromatic rings thereof, and wherein $Ar^2$ in the general formula (2) independently represents an unsubstituted monocyclic aromatic hydrocarbon group having 6 carbon atoms, an unsubstituted aromatic heterocyclic group having 3 to 17 carbon atoms, or an unsubstituted linked aromatic group formed by linking 2 to 4 aromatic rings thereof.

9. The organic electroluminescent device according to claim 1, wherein the monocyclic aromatic hydrocarbon group having 6 carbon atoms for $Ar^1$ in the general formula (1) is a benzene, wherein the aromatic heterocyclic group having 3 to 17 carbon atoms for $Ar^1$ in the general formula (1) is a carbazole, wherein the monocyclic aromatic hydrocarbon group having 6 carbon atoms for $Ar^2$ in the general formula (2) is a benzene, and wherein the aromatic heterocyclic group having 3 to 17 carbon atoms for $Ar^2$ in the general formula (2) is a carbazole or dibenzofuran.

10. The organic electroluminescent device according to claim 1, wherein the organic electroluminescent device emits blue light.

* * * * *